United States Patent
Dong et al.

(10) Patent No.: US 9,603,942 B2
(45) Date of Patent: *Mar. 28, 2017

(54) SOMATOSTATIN-DOPAMINE CHIMERIC ANALOGS

(71) Applicant: Ipsen Pharma S.A.S., Boulogne Billancourt (FR)

(72) Inventors: Zheng Xin Dong, Holliston, MA (US); Yeelana Shen, McKinney, TX (US)

(73) Assignee: Ipsen Pharma S.A.S., Boulogne (FR)

( * ) Notice: Subject to any disclaimer, the term of this patent is extended or adjusted under 35 U.S.C. 154(b) by 3 days.

This patent is subject to a terminal disclaimer.

(21) Appl. No.: 14/614,458

(22) Filed: Feb. 5, 2015

(65) Prior Publication Data

US 2015/0148522 A1 May 28, 2015

Related U.S. Application Data

(63) Continuation of application No. 14/068,286, filed on Oct. 31, 2013, now Pat. No. 8,952,128.

(60) Provisional application No. 61/721,372, filed on Nov. 1, 2012.

(51) Int. Cl.
| | |
|---|---|
| A61K 38/00 | (2006.01) |
| A61P 35/00 | (2006.01) |
| A61K 38/12 | (2006.01) |
| A61K 38/08 | (2006.01) |
| A61K 38/31 | (2006.01) |
| C07K 5/00 | (2006.01) |
| C07K 7/00 | (2006.01) |
| C07K 16/00 | (2006.01) |
| C07K 17/00 | (2006.01) |
| A61K 38/04 | (2006.01) |
| A61K 47/48 | (2006.01) |
| C07K 14/655 | (2006.01) |
| C07K 19/00 | (2006.01) |
| C07C 215/52 | (2006.01) |

(52) U.S. Cl.
CPC ............ *A61K 47/481* (2013.01); *A61K 38/00* (2013.01); *A61K 38/31* (2013.01); *C07C 215/52* (2013.01); *C07K 14/655* (2013.01); *C07K 19/00* (2013.01)

(58) Field of Classification Search
None
See application file for complete search history.

(56) References Cited

U.S. PATENT DOCUMENTS

| 2,589,978 A | 3/1952 | Stoll et al. |
|---|---|---|
| 2,619,488 A | 11/1952 | Stoll et al. |
| 3,901,894 A | 8/1975 | Kornfeld et al. |
| 3,966,941 A | 6/1976 | Semonsky et al. |
| 4,108,855 A | 8/1978 | Mago nee Karacsony et al. |
| 4,166,182 A | 8/1979 | Kornfeld et al. |
| 4,526,892 A | 7/1985 | Salvati et al. |
| 4,871,717 A | 10/1989 | Coy et al. |
| 4,904,642 A | 2/1990 | Coy et al. |
| 5,043,341 A | 8/1991 | Cohen et al. |
| 5,145,837 A | 9/1992 | Feyen et al. |
| 5,411,966 A | 5/1995 | Sauer et al. |
| 5,621,133 A | 4/1997 | Deninno et al. |
| 5,707,648 A | 1/1998 | Yiv |
| 5,753,618 A | 5/1998 | Cavanak et al. |
| 5,925,618 A | 7/1999 | Baumbach et al. |
| 6,025,193 A | 2/2000 | Weiss |
| 6,066,616 A | 5/2000 | Cavanak et al. |
| 6,117,427 A | 9/2000 | Hill et al. |
| 6,221,870 B1 | 4/2001 | Pfaeffli et al. |
| 6,358,967 B1 | 3/2002 | Wyrwa et al. |
| 6,465,613 B1 | 10/2002 | Coy et al. |
| 6,468,767 B1 | 10/2002 | Weinshank et al. |
| 7,101,843 B2 | 9/2006 | Glaesner et al. |
| 7,517,853 B2 | 4/2009 | Dong et al. |
| 7,572,883 B2 | 8/2009 | Culler et al. |
| 7,579,435 B2 | 8/2009 | Culler et al. |
| 7,897,578 B2 | 3/2011 | Ferrandis et al. |
| 8,178,651 B2 | 5/2012 | Culler et al. |
| 8,324,386 B2 | 12/2012 | Culler et al. |
| 8,952,128 B2 * | 2/2015 | Dong ................... C07C 215/52 530/311 |
| 2004/0209798 A1 | 10/2004 | Culler et al. |
| 2005/0042753 A1 | 2/2005 | Yang et al. |
| 2005/0118099 A1 | 6/2005 | Braslawsky et al. |
| 2005/0159356 A1 | 7/2005 | Dong et al. |
| 2005/0222025 A1 | 10/2005 | Culler et al. |
| 2006/0034937 A1 | 2/2006 | Patel |

(Continued)

FOREIGN PATENT DOCUMENTS

| BE | 618187 | 9/1962 |
|---|---|---|
| CH | 652720 A5 | 11/1985 |

(Continued)

OTHER PUBLICATIONS

Shenenberger, "Hyperprolactinemia", available online at http://emedicine.medscape.com/article/121784-overview, 3 pages (2015).*
The American Cancer Society, "Pituitary tumors," available online at http://www.cancer.org/acs/groups/cid/documents/webcontent/003133-pdf.pdf, 43 pages (2014).*
Wolin et al., Gastrointest. Cancer Res. 5:161-168 (2012).*
Koussis et al., EC Cancer 2.1:45-51 (2016).*
Tartarone et al., Semin. Nucl. Med. 46:239-242 (2016).*
The Cancer Research UK, "Neuroendocrine tumours (NETs)," available online at http://www.cancerresearchuk.org/about-cancer/cancers-in-general/cancer-questions/what-are-neuroendocrine-tumours, 5 pages (2014).*
Wick, M. M., Levodopa and Dopamine Analogs: Melanin Precursors as Antitumor Agents in Experimental Human and Murine Leukemia, Cancer Treat Rep., 1979, 63: 991-997.
Yamashita, K. et al., "Inhibitory effect of somatostatin on Helicobacter pylon proliferation in vitro", 1998, Gastroenterology, 115:1123-1130.
Rohrer, Susan P. et al., Rapid Identification of Subtype-Selective Agonists of the Somatostatin Receptor Through Combinatorial Chemistry, Science, 1998, 282:737-740.

(Continued)

*Primary Examiner* — Hasan Ahmed
*Assistant Examiner* — Thea D'Ambrosio
(74) *Attorney, Agent, or Firm* — Eileen J. Ennis; Ipsen Bioscience, Inc.

(57) ABSTRACT

The present invention relates to novel somatostatin-dopamine chimeric analogs and their therapeutic uses for the inhibition, prevention, and/or treatment of neoplasia, neuroendocrine tumors, Cushing's disease/syndrome, and other conditions.

18 Claims, 5 Drawing Sheets

(56) References Cited

U.S. PATENT DOCUMENTS

| | | |
|---|---|---|
| 2006/0052289 A1 | 3/2006 | Bruns et al. |
| 2006/0058221 A1 | 3/2006 | Miller |
| 2006/0063704 A1 | 3/2006 | Dong et al. |
| 2006/0211607 A1 | 9/2006 | Culler et al. |
| 2006/0251726 A1 | 11/2006 | Lin et al. |
| 2006/0292099 A1 | 12/2006 | Milburn et al. |
| 2007/0154392 A1 | 7/2007 | Loerrach et al. |
| 2008/0039405 A1 | 2/2008 | Langley et al. |
| 2011/0064742 A1 | 3/2011 | Mladen et al. |
| 2011/0065632 A1 | 3/2011 | Dong et al. |
| 2011/0178013 A1 | 7/2011 | Paternostre et al. |
| 2012/0010154 A1 | 1/2012 | Dong et al. |
| 2015/0252078 A1* | 9/2015 | Dong ............ A61K 38/12 424/9.1 |
| 2015/0290330 A1* | 10/2015 | Dong ............ C07C 215/52 514/11.1 |

FOREIGN PATENT DOCUMENTS

| | | |
|---|---|---|
| DE | 140044 | 2/1980 |
| EP | 0126968 B1 | 12/1988 |
| EP | 1099707 A2 | 5/2011 |
| GB | 959261 | 5/1964 |
| GB | 2103603 A | 2/1983 |
| GB | 2112382 A | 7/1983 |
| WO | 91/11447 A1 | 8/1991 |
| WO | 94/14806 A1 | 7/1994 |
| WO | 94/17104 A1 | 8/1994 |
| WO | 99/22735 A1 | 5/1999 |
| WO | 00/04018 A1 | 1/2000 |
| WO | 00/04916 A1 | 2/2000 |
| WO | 01/12155 A1 | 2/2001 |
| WO | 02/10215 A1 | 2/2002 |
| WO | 02/085902 A1 | 10/2002 |
| WO | 02/100888 A1 | 12/2002 |
| WO | 03/014158 A1 | 2/2003 |
| WO | 2004/091490 A2 | 10/2004 |
| WO | 2005/058252 A2 | 6/2005 |
| WO | 2005/117830 A1 | 12/2005 |
| WO | 2005/120453 A1 | 12/2005 |
| WO | 2007/144492 A2 | 12/2007 |
| WO | 2009/139855 A2 | 11/2009 |
| WO | 2010/037930 A1 | 4/2010 |
| WO | 2011/104627 A1 | 9/2011 |
| WO | 2011115871 A1 | 9/2011 |
| WO | 2014/070965 A2 | 5/2014 |

OTHER PUBLICATIONS

Ross, Nathan T. et al., Synthetic Mimetics of Protein Secondary Structure Domains, Phil. Trans. R. Soc., 2010, 368:989-1008.

International Search Report and Written Opinion from ISA/US mailed Apr. 30, 2014 for International Application No. PCT/US2013/067651.

International Search Report and Written Opinion from ISA/US mailed May 12, 2014 for International Application No. PCT/US2013/67661.

Andersen, M., The Role of Lanreotide Autogel(R) in the Treatment of Acromegaly, Expert Review of Endo. & Metabolism, 2007, p. 433-441, vol. 2, No. 4, Future Drugs Ltd., GB.

Baragli, et al., "Hetero-oligomerization of dopamine (D2R) and SST receptors (SSTRs) in CHO-K1 cells and cortical cultured neurons," Proc. 85th Endo. Soc. Mtg, Philadelphia, PA, USA, 2003, p. 2-669, Abstract only.

Basu, S. et al., "The neurotransmitter dopamine inhibits angiogenesis induced by vascular permeability factor/vascular endothelial growth factor," Nature Medicine, 2001, 7:569-574.

Basu, S. et al., "Dopamine, a neurotransmitter, influences the immune system," J. of Neuroimmunology, 2000, 102:113-124.

Basu, S. et al., "Role of Dopamine in Malignant Tumor Growth," Endocrine, 2000, 12:237-241.

Bosquet, C. et al., "Antiproliferative Effect of Somatostatin and Analogs," Chemotherapy, 2001, 47:30-39.

Colao, A. et al., "Growth hormone and prolactin excess," The Lancet, 1998, 352:1455-1461.

Culler, M. et al., The somatostatin-dopamine chimeric molecule, BIM-23A760, does not induce the insulin/glycemic effects observed with individual somatostatin or dopamine agonists in cynomolgus monkeys (Macaca fascicularis), 12th Mtg. of the Euro. Neuro. Assoc., Athens, Greece, 2006.

Culler, M. D., "Somatostatin-Dopamine Chimeras: A Novel Approach to Treatment of Neuroendocrine Tumors," Horm. Metab. Res., 2011, 43: 854-857.

Figueroa, F. E. et al., "Bromocriptine induces immunological changes related to disease parameters in rheumatoid arthritis", Br. J. Rheum., 1997, 36:1022-1023.

Fioravanti et al., "Somatostatin 14 and joint inflammation: evidence for intraarticular efficacy of prolonged administration in rheumatoid arthritis", Drugs Exp. Clin. Res., 1995, 21:97-103. (Abstract only).

Florio, T. et al., "Efficacy of a dopamine-somatostatin chimeric molecule, BIM-23A760, in the control of cell growth from primary cultures of human non-functioning pituitary adenomas: a multicenter study," Endocrine-Related Cancer, 2008, 15:583-596.

Freda, P. et al., "Clinical Review 110: Diagnosis and treatment of pituitary tumors," J. Clin. Endo. Metab., 1999, 84 (11):3859-3866.

Froidevaux, S. et al., "Somatostatin Analogs and Radiopeptides in Cancer Therapy," Biopolymers, 2002, 66:161-183.

Gabor, F. et al., "Drug-protein conjugates: haptenation of 1-methyl-10a-methozydihydrolysergol and 5-bromonicotinic acid to albumin for the production of epitope-specific monoclonal antibodies against nicergoline", J. Pharm. Sci., 1995, 84:1120-1125.

Goldstein, M. et al., "Dopaminergic mechanisms in the pathogenesis of schizophrenia," FASEB Journal, 1992, 6: 2413-2421.

Graybiel, A. et al., "The Nigrostriatal System in Parkinson's Disease," Adv. Neurol., 1990, 53: 17-29.

Hoffman, A.J. et al., "Synthesis and LSD-like Discriminative Stimulus Properties in a Series of N(6)-Alkyl Norlysergic Acid N,N-Diethylamide Derivatives," J. Med. Chem., 1985, 28(9):1252-1255.

Ishibashi, M., et al., "Inhibition of growth of human small cell lung cancer by bromocriptine", Cancer Res., 1994, 54:3442-3446.

Jaquet, P., "Evidence for dopamine agonists in the treatment of acromegaly," J. Endo., 1997, 155:S59-S60.

Jaquet, P. et al., "Quantitative and functional expression of somatostatin receptor subtypes in human prolactinomas," J. Clin. Endo. Metab., 1999, 84(9):3268-3276.

Jaquet, P. et al., "Efficacy of chimeric molecules directed towards multiple somatostatin and dopamine receptors on inhibition of GH and prolactin secretion from GH-secreting pituitary adenomas classified as partially responsive to somatostatin analog therapy", Eu. J. Endo., 2005, 153:135-141.

Jenkinson, D. H. et al., "International Union of Pharmacology Committee on Receptor Nomenclature and Drug Classification. IX. Recommendations on Terms and Symbols in Quantitative Pharmacology," Pharmacol. Rev., 1995, 47(2):255-266.

Krepelka, J. et al., "Some esters of N-(D-6-methyl-8-ergolin-1-ylmethyl)-carbamic acid," Collection Czechoslov. Chem. Commun., 1977, 42:1886-1889.

Losse, G. et al., "Synthese von lysergyl-enkephalin-derivaten," Eur. J. Med. Chem., 1979, 14:325-328.

Maheshwari, H. et al., "Long-acting peptidomimergic control of gigantism caused by pituitary acidophilic stem cell adenoma," J. Clin. Endo. Metab., 2000, 85(9):3409-3416.

Mantegani, S. et al., "Synthesis and antihypertensive activity of 2,4-dioxoimidazolidin-1-yl and perhydro-2,4-dioxopyrimidin-1-yl ergoline derivatives," II Farmaco, 1998, 53:293-304.

Miyagi, M. et al., "Dopamine receptor affinities in vitro and stereotypic activities in vivo of cabergoline in rats," Biol. Pharm. Bull., 1996, 19:1210-1213.

Nicolaus, B. J. R., "Symbiotic Approach to Drug Design," Decision Making in Drug Research, 1983, 173-186.

Olanow, C. W. et al., "Etiology and Pathogenesis of Parkinson's Disease," Annu. Rev. Neurosci, 1999, 22: 123-144.

Patel, Yogesh C., "Somatostatin and Its Receptor Family," Frontiers in Neuroendocrinology, 1999, 20: 157-198.

(56) References Cited

OTHER PUBLICATIONS

Pfeiffer, M. et al., "Heterodimerization of Somatostatin and Opioid Receptors Cross-modulates Phosphorylation, Internalization, and Densensitization," J. Biol. Chem., 2002, 277: 19762-19772.

Racine, M. et al., "Medical Management of Growth Hormone-Secreting Pituitary Adenomas," Pituitary, 2002, 5: 67-76.

Reisine, T. et al., "Molecular Biology of Somatostatin Receptors," Endo. Rev., 1995, 16: 427-442.

Reubi, J.C. et al., "Distribution of somatostatin receptors in normal and neoplastic human tissues: Recent advances and potential relevance," Yale J. Biol. and Med., 1997, 70:471-479.

Reubi, J. C. et al., "Somatostatin Receptors in Human Endocrine Tumors," Cancer Res., 1987, 47: 551-558.

Rocheville, M. et al., "Receptors for Dopamine and Somatostatin: Formulation of Hetero-Oligomers with Enhanced Functional Activity," Science, 2000, 288(5643):154-157.

Saveanu, A. et al, Demonstration of Enhanced Potency of a Chimeric Somatostatin-Dopamine Molecule, BIM-23A387, in Suppressing Growth Hormone and Prolactin Secretion from Human Pituitary Somatotoph Adenoma Cells, J. of Clinical Endo. & Metabolism, 2002, p. 5545-5552, vol. 87, No. 12, The Endocrine Society, US.

Saveanu, A. et al., "A chimeric somatostatin-dopamine molecule, BIM-23A387 has enhanced potency in suppressing GH and PRL secretion in acromegaly," ENEA 2002 Conference, Munich, Germany, Sep. 12-14, 2002, OC-2.4, p. 49, Abstract (XP-002306950).

Stoll, A. et al., "Synthesis of 6-Methyl-8-oxyisoergoline (1) and Attempts to Dehydrogenate Same to 6-Methyl-ergolin-8-one," 28th Report on Ergot Alkaloids, Helvetica Chimica Acta., 1952, 35(152-153):1249-1258.

Strosberg, J. et al., "Antiproliferative effect of somatostatin analogs in gastroenteropancreatic neuroendocrine tumors," World J. Gastroenterol, 2010, 26: 2963-2970.

Sweet, et al., "Piribedil—an oral dopamine agonist for treatment of Parkinson's disease", Trans. Am. Neurol. Assoc., 1974, 99:258-60. (Title only).

Tangbanluekal, L. et al., "Prolactin mediates estradiol-induced inflammation in the lateral prostate of Wistar rats," Endocrinology, 1993, 132:2407-2416.

Taylor, J. E., et al.,"In vitro and in vivo inhibition of human small cell lung carcinoma (NCI-H69) growth by a somatostatin analogue", Biochem. Biophys. Res. Comm., 1988, 153:81-86.

Temperilli, A. et al., "Anti-hypertensive activity of ergolinyl-ureido and thioureido derivatives", Eur. J. Med. Chem., 1988, 23:77-81.

Terenius, L., "Somatostatin and ACTH are peptides with partial antagonist-like selectivity for opiate receptors", Eur. J. Pharmacol., 1976, 38:211-3. (Abstract only).

Torsello, A. et al., "Short Ghrelin Peptides Neither Displace Ghrelin Binding In Vitro nor Stimulate GH Release In Vivo," Endo., 2002, 143: 1968-1971.

Walzel, B. et al., "Mechanism of alkaloid cyclopeptide synthesis in the ergot fungus Claviceps purpurea," Chemistry and Biology, 1997, 4:223-230.

Wick, M. M. et al., "Dopamine: A Novel Antitumor Agent Active Against B-16 Melanoma In Vivo," J. Investigative Derm., 1978, 71: 163-164.

Wick, M. M., "3,4-Dihydroxybenzylamine: A Dopamine Analog With Enhanced Antitumor Activity Against B16 Melanoma," J. Natl. Cancer Inst., 1979, 63: 1465-1467.

Reubi, Jean Claude et al., "A new peptidic somatostatin agonist with high affinity to all five somatostatin receptors," EP J. of Pharma., 2002, 456: 45-49.

Sarantakis, D., "Structure-Activity Studies of Somatostatin Analogs, Substituted at Positions 4 and 5," Peptides, 1986: Proceedings of the 19th European Peptide Symposium, Porto Carras, Chalkidiki, Greece, 1987, 535-538.

Sasaki, Yusuke et al., "Solid-Phase Synthesis and Biological Properties of PSI[CH2NH] Pseudopeptide Analogues of a Highly Potent Somatostatin Octapeptide," J. of Medicinal Chemistry, 1987, 30: 1162-1166.

* cited by examiner

SEQUENCE LISTING

```
<160> NUMBER OF SEQ ID NOS: 59

<210> SEQ ID NO 1
<211> LENGTH: 8
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with (D-6-methyl-8beta-ergolinyl)-
      propionyl via a psi(CH2NH) bond at the alpha-amino group
<220> FEATURE:
<221> NAME/KEY: MOD_RES
<222> LOCATION: (1)..(8)
<223> OTHER INFORMATION: cyclized with a lactam bridge
<220> FEATURE:
<221> NAME/KEY: MOD_RES
<222> LOCATION: (1)..(1)
<223> OTHER INFORMATION: Xaa = D-Lys
<220> FEATURE:
<221> NAME/KEY: MOD_RES
<222> LOCATION: (5)..(5)
<223> OTHER INFORMATION: Xaa = D-Trp
<220> FEATURE:
<221> NAME/KEY: MOD_RES
<222> LOCATION: (8)..(8)
<223> OTHER INFORMATION: modified with 4-Fl

<400> SEQUENCE: 1

Xaa Arg Phe Phe Xaa Lys Thr Phe
1               5

<210> SEQ ID NO 2
<211> LENGTH: 8
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with (D-6-methyl-8beta-ergolinyl)-
      butanoyl via a psi(CH2NH) bond at the alpha-amino group
<220> FEATURE:
<221> NAME/KEY: MOD_RES
<222> LOCATION: (1)..(8)
```

```
<223> OTHER INFORMATION: cyclized with a lactam bridge
<220> FEATURE:
<221> NAME/KEY: MOD_RES
<222> LOCATION: (1)..(1)
<223> OTHER INFORMATION: Xaa = D-Lys
<220> FEATURE:
<221> NAME/KEY: MOD_RES
<222> LOCATION: (5)..(5)
<223> OTHER INFORMATION: Xaa = D-Trp
<220> FEATURE:
<221> NAME/KEY: MOD_RES
<222> LOCATION: (8)..(8)
<223> OTHER INFORMATION: modified with 4-Fl

<400> SEQUENCE: 2

Xaa Arg Phe Phe Xaa Lys Thr Phe
1               5

<210> SEQ ID NO 3
<211> LENGTH: 8
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with (D-6-methyl-8beta-ergolinyl)-
      pentanoyl via a psi(CH2NH) bond at the alpha-amino group
<220> FEATURE:
<221> NAME/KEY: MOD_RES
<222> LOCATION: (1)..(8)
<223> OTHER INFORMATION: cyclized with a lactam bridge
<220> FEATURE:
<221> NAME/KEY: MOD_RES
<222> LOCATION: (1)..(1)
<223> OTHER INFORMATION: Xaa = D-Lys
<220> FEATURE:
<221> NAME/KEY: MOD_RES
<222> LOCATION: (5)..(5)
<223> OTHER INFORMATION: Xaa = D-Trp
<220> FEATURE:
<221> NAME/KEY: MOD_RES
<222> LOCATION: (8)..(8)
<223> OTHER INFORMATION: modified with 4-Fl

<400> SEQUENCE: 3

Xaa Arg Phe Phe Xaa Lys Thr Phe
1               5

<210> SEQ ID NO 4
<211> LENGTH: 9
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with (D-6-methyl-8beta-
      ergolinylmethyl)thioacetyl (Dop1) via an amide bond at the alpha-
      amino group
<220> FEATURE:
<221> NAME/KEY: MOD_RES
<222> LOCATION: (1)..(2)
<223> OTHER INFORMATION: a psi(CH2NH) bond
<220> FEATURE:
<221> NAME/KEY: MOD_RES
<222> LOCATION: (2)..(9)
<223> OTHER INFORMATION: cyclized with a lactam bridge
<220> FEATURE:
<221> NAME/KEY: MOD_RES
<222> LOCATION: (2)..(2)
<223> OTHER INFORMATION: Xaa = D-Lys
<220> FEATURE:
```

```
<221> NAME/KEY: MOD_RES
<222> LOCATION: (5)..(5)
<223> OTHER INFORMATION: Xaa = beta-(4-pyridinyl)alanine (4-Pal)
<220> FEATURE:
<221> NAME/KEY: MOD_RES
<222> LOCATION: (6)..(6)
<223> OTHER INFORMATION: Xaa = D-Trp

<400> SEQUENCE: 4

Tyr Xaa Arg Phe Xaa Xaa Lys Thr Phe
1               5

<210> SEQ ID NO 5
<211> LENGTH: 9
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with (D-6-methyl-8beta-
      ergolinylmethyl)thioacetyl (Dop1) via an amide bond at the alpha-
      amino group
<220> FEATURE:
<221> NAME/KEY: MOD_RES
<222> LOCATION: (1)..(2)
<223> OTHER INFORMATION: a psi(CH2NH) bond
<220> FEATURE:
<221> NAME/KEY: MOD_RES
<222> LOCATION: (2)..(9)
<223> OTHER INFORMATION: cyclized with a lactam bridge
<220> FEATURE:
<221> NAME/KEY: MOD_RES
<222> LOCATION: (2)..(2)
<223> OTHER INFORMATION: Xaa = D-Lys
<220> FEATURE:
<221> NAME/KEY: MOD_RES
<222> LOCATION: (6)..(6)
<223> OTHER INFORMATION: Xaa = D-Trp
<220> FEATURE:
<221> NAME/KEY: MOD_RES
<222> LOCATION: (9)..(9)
<223> OTHER INFORMATION: modified with 4-Fl

<400> SEQUENCE: 5

Tyr Xaa Arg Phe Phe Xaa Lys Thr Phe
1               5

<210> SEQ ID NO 6
<211> LENGTH: 8
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with (D-6-methyl-8beta-
      ergolinylmethyl)thioacetyl (Dop1) via a psi(CH2NH) bond at the
      alpha-amino group
<220> FEATURE:
<221> NAME/KEY: MOD_RES
<222> LOCATION: (1)..(8)
<223> OTHER INFORMATION: cyclized with a lactam bridge
<220> FEATURE:
<221> NAME/KEY: MOD_RES
<222> LOCATION: (1)..(1)
<223> OTHER INFORMATION: Xaa = D-Lys
<220> FEATURE:
<221> NAME/KEY: MOD_RES
<222> LOCATION: (5)..(5)
<223> OTHER INFORMATION: Xaa = D-Trp
<220> FEATURE:
<221> NAME/KEY: MOD_RES
```

```
<222> LOCATION: (8)..(8)
<223> OTHER INFORMATION: modified with 4-Fl

<400> SEQUENCE: 6

Xaa Arg Phe Phe Xaa Lys Thr Phe
1               5

<210> SEQ ID NO 7
<211> LENGTH: 8
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with (D-6-methyl-8beta-
      ergolinylmethyl)thioacetyl (Dop1) via a psi(CH2NH) bond at the
      alpha-amino group
<220> FEATURE:
<221> NAME/KEY: MOD_RES
<222> LOCATION: (1)..(8)
<223> OTHER INFORMATION: cyclized with a lactam bridge
<220> FEATURE:
<221> NAME/KEY: MOD_RES
<222> LOCATION: (1)..(1)
<223> OTHER INFORMATION: Xaa = D-Lys
<220> FEATURE:
<221> NAME/KEY: MOD_RES
<222> LOCATION: (5)..(5)
<223> OTHER INFORMATION: Xaa = D-Trp
<220> FEATURE:
<221> NAME/KEY: MOD_RES
<222> LOCATION: (8)..(8)
<223> OTHER INFORMATION: modified with 3,4-Fl

<400> SEQUENCE: 7

Xaa Arg Phe Phe Xaa Lys Thr Phe
1               5

<210> SEQ ID NO 8
<211> LENGTH: 8
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with (D-6-methyl-8beta-
      ergolinylmethyl)thioacetyl (Dop1) via a psi(CH2NH) bond at the
      alpha-amino group
<220> FEATURE:
<221> NAME/KEY: MOD_RES
<222> LOCATION: (1)..(8)
<223> OTHER INFORMATION: cyclized with a lactam bridge
<220> FEATURE:
<221> NAME/KEY: MOD_RES
<222> LOCATION: (1)..(1)
<223> OTHER INFORMATION: Xaa = D-Lys
<220> FEATURE:
<221> NAME/KEY: MOD_RES
<222> LOCATION: (5)..(5)
<223> OTHER INFORMATION: Xaa = D-Trp
<220> FEATURE:
<221> NAME/KEY: MOD_RES
<222> LOCATION: (8)..(8)
<223> OTHER INFORMATION: modified with 3,5-Fl

<400> SEQUENCE: 8

Xaa Arg Phe Phe Xaa Lys Thr Phe
1               5
```

```
<210> SEQ ID NO 9
<211> LENGTH: 8
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with (D-6-methyl-8beta-
      ergolinylmethyl)thioacetyl (Dop1) via a psi(CH2NH) bond at the
      alpha-amino group
<220> FEATURE:
<221> NAME/KEY: MOD_RES
<222> LOCATION: (1)..(8)
<223> OTHER INFORMATION: cyclized with a lactam bridge
<220> FEATURE:
<221> NAME/KEY: MOD_RES
<222> LOCATION: (1)..(1)
<223> OTHER INFORMATION: Xaa = D-Lys
<220> FEATURE:
<221> NAME/KEY: MOD_RES
<222> LOCATION: (5)..(5)
<223> OTHER INFORMATION: Xaa = D-Trp
<220> FEATURE:
<221> NAME/KEY: MOD_RES
<222> LOCATION: (8)..(8)
<223> OTHER INFORMATION: modified with 3-Fl

<400> SEQUENCE: 9

Xaa Arg Phe Phe Xaa Lys Thr Phe
1               5

<210> SEQ ID NO 10
<211> LENGTH: 8
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with (D-6-methyl-8beta-
      ergolinylmethyl)thioacetyl (Dop1) via a psi(CH2NH) bond at the
      alpha-amino group
<220> FEATURE:
<221> NAME/KEY: MOD_RES
<222> LOCATION: (1)..(8)
<223> OTHER INFORMATION: cyclized with a lactam bridge
<220> FEATURE:
<221> NAME/KEY: MOD_RES
<222> LOCATION: (1)..(1)
<223> OTHER INFORMATION: Xaa = D-Lys
<220> FEATURE:
<221> NAME/KEY: MOD_RES
<222> LOCATION: (5)..(5)
<223> OTHER INFORMATION: Xaa = D-Trp
<220> FEATURE:
<221> NAME/KEY: MOD_RES
<222> LOCATION: (8)..(8)
<223> OTHER INFORMATION: modified with 2-Fl

<400> SEQUENCE: 10

Xaa Arg Phe Phe Xaa Lys Thr Phe
1               5

<210> SEQ ID NO 11
<211> LENGTH: 8
<212> TYPE: PRT
<213> ORGANISM: Artificial Sequence
<220> FEATURE:
<223> OTHER INFORMATION: Somatostatin-dopamine chimeric peptide analog
<220> FEATURE:
```

```
<221> NAME/KEY: MOD_RES
<222> LOCATION: (1)..(1)
<223> OTHER INFORMATION: modified with (D-6-methyl-8beta-
      ergolinylmethyl)thioacetyl (Dop1) via a psi(CH2NH) bond at the
      alpha-amino group
<220> FEATURE:
<221> NAME/KEY: MOD_RES
<222> LOCATION: (1)..(8)
<223> OTHER INFORMATION: cyclized with a lactam bridge
<220> FEATURE:
<221> NAME/KEY: MOD_RES
<222> LOCATION: (1)..(1)
<223> OTHER INFORMATION: Xaa = D-Lys
<220> FEATURE:
<221> NAME/KEY: MOD_RES
<222> LOCATION: (5)..(5)
<223> OTHER INFORMATION: Xaa = D-Trp
<220> FEATURE:
<221> NAME/KEY: MOD_RES
<222> LOCATION: (8)..(8)
<223> OTHER INFORMATION: modified with 2,3,4,5,6-Fl

<400> SEQUENCE: 11

Xaa Arg Phe Phe Xaa Lys Thr Phe
1               5

<210> SEQ ID NO 12
<211> LENGTH: 8
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with (D-6-methyl-8beta-
      ergolinylmethyl)thioacetyl (Dop1) via a psi(CH2NH) bond at the
      alpha-amino group
<220> FEATURE:
<221> NAME/KEY: MOD_RES
<222> LOCATION: (1)..(8)
<223> OTHER INFORMATION: cyclized with a lactam bridge
<220> FEATURE:
<221> NAME/KEY: MOD_RES
<222> LOCATION: (1)..(1)
<223> OTHER INFORMATION: Xaa = D-Lys
<220> FEATURE:
<221> NAME/KEY: MOD_RES
<222> LOCATION: (4)..(4)
<223> OTHER INFORMATION: Xaa = beta-(4-pyridinyl)alanine (4-Pal)
<220> FEATURE:
<221> NAME/KEY: MOD_RES
<222> LOCATION: (5)..(5)
<223> OTHER INFORMATION: Xaa = D-Trp

<400> SEQUENCE: 12

Xaa Arg Phe Xaa Xaa Lys Thr Tyr
1               5

<210> SEQ ID NO 13
<211> LENGTH: 9
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with (D-6-methyl-8beta-
      ergolinylmethyl)thioacetyl (Dop1) via an amide bond at the alpha-
      amino group
<220> FEATURE:
<221> NAME/KEY: MOD_RES
<222> LOCATION: (1)..(1)
<223> OTHER INFORMATION: modified with (D-6-methyl-8beta-
```

```
       ergolinylmethyl)thioacetyl (Dop1) via an amide bond at the
       epsilon-amino group
<220> FEATURE:
<221> NAME/KEY: MOD_RES
<222> LOCATION: (1)..(2)
<223> OTHER INFORMATION: a psi(CH2NH) bond
<220> FEATURE:
<221> NAME/KEY: MOD_RES
<222> LOCATION: (2)..(9)
<223> OTHER INFORMATION: cyclized with a lactam bridge
<220> FEATURE:
<221> NAME/KEY: MOD_RES
<222> LOCATION: (2)..(2)
<223> OTHER INFORMATION: Xaa = D-Lys
<220> FEATURE:
<221> NAME/KEY: MOD_RES
<222> LOCATION: (5)..(5)
<223> OTHER INFORMATION: Xaa = beta-(4-pyridinyl)alanine (4-Pal)
<220> FEATURE:
<221> NAME/KEY: MOD_RES
<222> LOCATION: (6)..(6)
<223> OTHER INFORMATION: Xaa = D-Trp

<400> SEQUENCE: 13

Lys Xaa Arg Phe Xaa Xaa Lys Thr Tyr
1               5

<210> SEQ ID NO 14
<211> LENGTH: 9
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with (D-6-methyl-8beta-
       ergolinylmethyl)thioacetyl (Dop1) via an amide bond at the alpha-
       amino group
<220> FEATURE:
<221> NAME/KEY: MOD_RES
<222> LOCATION: (1)..(1)
<223> OTHER INFORMATION: modified with (D-6-methyl-8beta-
       ergolinylmethyl)thioacetyl (Dop1) via an amide bond at the
       epsilon-amino group
<220> FEATURE:
<221> NAME/KEY: MOD_RES
<222> LOCATION: (1)..(2)
<223> OTHER INFORMATION: a psi(CH2NH) bond
<220> FEATURE:
<221> NAME/KEY: MOD_RES
<222> LOCATION: (2)..(9)
<223> OTHER INFORMATION: cyclized with a lactam bridge
<220> FEATURE:
<221> NAME/KEY: MOD_RES
<222> LOCATION: (2)..(2)
<223> OTHER INFORMATION: Xaa = D-Lys
<220> FEATURE:
<221> NAME/KEY: MOD_RES
<222> LOCATION: (5)..(5)
<223> OTHER INFORMATION: Xaa = beta-(4-pyridinyl)alanine (4-Pal)
<220> FEATURE:
<221> NAME/KEY: MOD_RES
<222> LOCATION: (6)..(6)
<223> OTHER INFORMATION: Xaa = D-Trp

<400> SEQUENCE: 14

Lys Xaa Arg Phe Xaa Xaa Lys Thr Phe
1               5

<210> SEQ ID NO 15
<211> LENGTH: 8
<212> TYPE: PRT
<213> ORGANISM: Artificial Sequence
<220> FEATURE:
```

```
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with (D-6-methyl-8beta-
      ergolinylmethyl)thioacetyl (Dop1) in which the thioether group is
      modified to (SO2), via a psi(CH2NH) bond at the alpha-amino group
<220> FEATURE:
<221> NAME/KEY: MOD_RES
<222> LOCATION: (1)..(8)
<223> OTHER INFORMATION: cyclized with a lactam bridge
<220> FEATURE:
<221> NAME/KEY: MOD_RES
<222> LOCATION: (1)..(1)
<223> OTHER INFORMATION: Xaa = D-Lys
<220> FEATURE:
<221> NAME/KEY: MOD_RES
<222> LOCATION: (5)..(5)
<223> OTHER INFORMATION: Xaa = D-Trp
<220> FEATURE:
<221> NAME/KEY: MOD_RES
<222> LOCATION: (8)..(8)
<223> OTHER INFORMATION: modified with 4-Fl

<400> SEQUENCE: 15

Xaa Arg Phe Phe Xaa Lys Thr Phe
1               5

<210> SEQ ID NO 16
<211> LENGTH: 8
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with (D-6-methyl-8beta-
      ergolinylmethyl)thioacetyl (Dop1) in which the thioether group is
      modified to (SO) R-stereoisomer form, via a psi(CH2NH) bond at the
      alpha-amino group
<220> FEATURE:
<221> NAME/KEY: MOD_RES
<222> LOCATION: (1)..(8)
<223> OTHER INFORMATION: cyclized with a lactam bridge
<220> FEATURE:
<221> NAME/KEY: MOD_RES
<222> LOCATION: (1)..(1)
<223> OTHER INFORMATION: Xaa = D-Lys
<220> FEATURE:
<221> NAME/KEY: MOD_RES
<222> LOCATION: (4)..(4)
<223> OTHER INFORMATION: Xaa = beta-(4-pyridinyl)alanine (4-Pal)
<220> FEATURE:
<221> NAME/KEY: MOD_RES
<222> LOCATION: (5)..(5)
<223> OTHER INFORMATION: Xaa = D-Trp

<400> SEQUENCE: 16

Xaa Arg Phe Xaa Xaa Lys Thr Tyr
1               5

<210> SEQ ID NO 17
<211> LENGTH: 8
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with (D-6-methyl-8beta-
      ergolinylmethyl)thioacetyl (Dop1) in which the thioether group is
      modified to (SO) S-stereoisomer form, via a psi(CH2NH) bond via at
      the alpha-amino group
```

```
<220> FEATURE:
<221> NAME/KEY: MOD_RES
<222> LOCATION: (1)..(8)
<223> OTHER INFORMATION: cyclized with a lactam bridge
<220> FEATURE:
<221> NAME/KEY: MOD_RES
<222> LOCATION: (1)..(1)
<223> OTHER INFORMATION: Xaa = D-Lys
<220> FEATURE:
<221> NAME/KEY: MOD_RES
<222> LOCATION: (4)..(4)
<223> OTHER INFORMATION: Xaa = beta-(4-pyridinyl)alanine (4-Pal)
<220> FEATURE:
<221> NAME/KEY: MOD_RES
<222> LOCATION: (5)..(5)
<223> OTHER INFORMATION: Xaa = D-Trp

<400> SEQUENCE: 17

Xaa Arg Phe Xaa Xaa Lys Thr Tyr
1               5

<210> SEQ ID NO 18
<211> LENGTH: 8
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with (D-6-methyl-8beta-
      ergolinylmethyl)thioacetyl (Dop1) in which the thioether group is
      modified to (SO), via a psi(CH2NH) bond at the alpha-amino group
<220> FEATURE:
<221> NAME/KEY: MOD_RES
<222> LOCATION: (1)..(8)
<223> OTHER INFORMATION: cyclized with a lactam bridge
<220> FEATURE:
<221> NAME/KEY: MOD_RES
<222> LOCATION: (1)..(1)
<223> OTHER INFORMATION: Xaa = D-Lys
<220> FEATURE:
<221> NAME/KEY: MOD_RES
<222> LOCATION: (4)..(4)
<223> OTHER INFORMATION: Xaa = beta-(4-pyridinyl)alanine (4-Pal)
<220> FEATURE:
<221> NAME/KEY: MOD_RES
<222> LOCATION: (5)..(5)
<223> OTHER INFORMATION: Xaa = D-Trp

<400> SEQUENCE: 18

Xaa Arg Phe Xaa Xaa Lys Thr Tyr
1               5

<210> SEQ ID NO 19
<211> LENGTH: 9
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with (D-6-methyl-8beta-
      ergolinylmethyl)thioacetyl (Dop1) in which the thioether is
      modified to (SO), via an amide bond at the alpha-amino group
<220> FEATURE:
<221> NAME/KEY: MOD_RES
<222> LOCATION: (1)..(2)
<223> OTHER INFORMATION: a psi(CH2NH) bond
<220> FEATURE:
<221> NAME/KEY: MOD_RES
<222> LOCATION: (2)..(9)
<223> OTHER INFORMATION: cyclized with a lactam bridge
<220> FEATURE:
```

```
<221> NAME/KEY: MOD_RES
<222> LOCATION: (2)..(2)
<223> OTHER INFORMATION: Xaa = D-Lys
<220> FEATURE:
<221> NAME/KEY: MOD_RES
<222> LOCATION: (6)..(6)
<223> OTHER INFORMATION: Xaa = D-Trp
<220> FEATURE:
<221> NAME/KEY: MOD_RES
<222> LOCATION: (9)..(9)
<223> OTHER INFORMATION: modified with 4-Fl

<400> SEQUENCE: 19

Tyr Xaa Arg Phe Phe Xaa Lys Thr Phe
1               5

<210> SEQ ID NO 20
<211> LENGTH: 8
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with (D-6-methyl-8beta-
      ergolinylmethyl)thioacetyl (Dop1) in which the thioether group is
      modified to (SO), via a psi(CH2NH) bond at the alpha-amino group
<220> FEATURE:
<221> NAME/KEY: MOD_RES
<222> LOCATION: (1)..(8)
<223> OTHER INFORMATION: cyclized with a lactam bridge
<220> FEATURE:
<221> NAME/KEY: MOD_RES
<222> LOCATION: (1)..(1)
<223> OTHER INFORMATION: Xaa = D-Lys
<220> FEATURE:
<221> NAME/KEY: MOD_RES
<222> LOCATION: (5)..(5)
<223> OTHER INFORMATION: Xaa = D-Trp
<220> FEATURE:
<221> NAME/KEY: MOD_RES
<222> LOCATION: (8)..(8)
<223> OTHER INFORMATION: modified with 4-Fl

<400> SEQUENCE: 20

Xaa Arg Phe Phe Xaa Lys Thr Phe
1               5

<210> SEQ ID NO 21
<211> LENGTH: 9
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with (D-6-methyl-8beta-
      ergolinylmethyl)thioacetyl (Dop1) in which the thioether group is
      modified to (SO), via an amide bond at the alpha-amino group
<220> FEATURE:
<221> NAME/KEY: MOD_RES
<222> LOCATION: (1)..(2)
<223> OTHER INFORMATION: a psi(CH2NH) bond
<220> FEATURE:
<221> NAME/KEY: MOD_RES
<222> LOCATION: (2)..(9)
<223> OTHER INFORMATION: cyclized with a lactam bridge
<220> FEATURE:
<221> NAME/KEY: MOD_RES
<222> LOCATION: (2)..(2)
<223> OTHER INFORMATION: Xaa = D-Lys
<220> FEATURE:
<221> NAME/KEY: MOD_RES
```

```
<222> LOCATION: (5)..(5)
<223> OTHER INFORMATION: Xaa = beta-(4-pyridinyl)alanine (4-Pal)
<220> FEATURE:
<221> NAME/KEY: MOD_RES
<222> LOCATION: (6)..(6)
<223> OTHER INFORMATION: Xaa = D-Trp

<400> SEQUENCE: 21

Tyr Xaa Arg Phe Xaa Xaa Lys Thr Phe
1               5

<210> SEQ ID NO 22
<211> LENGTH: 9
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with (D-6-methyl-8beta-
      ergolinylmethyl)thioacetyl (Dop1) in which the thioether group is
      modified to (SO), via an amide bond at the alpha-amino group
<220> FEATURE:
<221> NAME/KEY: MOD_RES
<222> LOCATION: (1)..(1)
<223> OTHER INFORMATION: modified with (D-6-methyl-8beta-
      ergolinylmethyl)thioacetyl (Dop1) in which the thioether is
      modified to (SO), via an amide bond at the epsilon-amino group
<220> FEATURE:
<221> NAME/KEY: MOD_RES
<222> LOCATION: (1)..(2)
<223> OTHER INFORMATION: a psi(CH2NH) bond
<220> FEATURE:
<221> NAME/KEY: MOD_RES
<222> LOCATION: (2)..(9)
<223> OTHER INFORMATION: cyclized with a lactam bridge
<220> FEATURE:
<221> NAME/KEY: MOD_RES
<222> LOCATION: (2)..(2)
<223> OTHER INFORMATION: Xaa = D-Lys
<220> FEATURE:
<221> NAME/KEY: MOD_RES
<222> LOCATION: (5)..(5)
<223> OTHER INFORMATION: Xaa = beta-(4-pyridinyl)alanine (4-Pal)
<220> FEATURE:
<221> NAME/KEY: MOD_RES
<222> LOCATION: (6)..(6)
<223> OTHER INFORMATION: Xaa = D-Trp

<400> SEQUENCE: 22

Lys Xaa Arg Phe Xaa Xaa Lys Thr Tyr
1               5

<210> SEQ ID NO 23
<211> LENGTH: 9
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with (D-6-methyl-8beta-
      ergolinylmethyl)thioacetyl (Dop1) in which the thioether group is
      modified to (SO), via an amide bond at the alpha-amino group
<220> FEATURE:
<221> NAME/KEY: MOD_RES
<222> LOCATION: (1)..(1)
<223> OTHER INFORMATION: modified with (D-6-methyl-8beta-
      ergolinylmethyl)thioacetyl (Dop1) in which the thioether is
      modified to (SO), via an amide bond at the epsilon-amino group
<220> FEATURE:
<221> NAME/KEY: MOD_RES
<222> LOCATION: (1)..(2)
```

<223> OTHER INFORMATION: a psi(CH2NH) bond
<220> FEATURE:
<221> NAME/KEY: MOD_RES
<222> LOCATION: (2)..(9)
<223> OTHER INFORMATION: cyclized with a lactam bridge
<220> FEATURE:
<221> NAME/KEY: MOD_RES
<222> LOCATION: (2)..(2)
<223> OTHER INFORMATION: Xaa = D-Lys
<220> FEATURE:
<221> NAME/KEY: MOD_RES
<222> LOCATION: (5)..(5)
<223> OTHER INFORMATION: Xaa = beta-(4-pyridinyl)alanine (4-Pal)
<220> FEATURE:
<221> NAME/KEY: MOD_RES
<222> LOCATION: (6)..(6)
<223> OTHER INFORMATION: Xaa = D-Trp

<400> SEQUENCE: 23

Lys Xaa Arg Phe Xaa Xaa Lys Thr Phe
1               5

<210> SEQ ID NO 24
<211> LENGTH: 9
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with (D-6-methyl-8beta-
      ergolinylmethyl)thioacetyl (Dop1) in which the thioether group is
      modified to (SO2), via an amide bond at the alpha-amino group
<220> FEATURE:
<221> NAME/KEY: MOD_RES
<222> LOCATION: (1)..(2)
<223> OTHER INFORMATION: a psi(CH2NH) bond
<220> FEATURE:
<221> NAME/KEY: MOD_RES
<222> LOCATION: (2)..(9)
<223> OTHER INFORMATION: cyclized with a lactam bridge
<220> FEATURE:
<221> NAME/KEY: MOD_RES
<222> LOCATION: (2)..(2)
<223> OTHER INFORMATION: Xaa = D-Lys
<220> FEATURE:
<221> NAME/KEY: MOD_RES
<222> LOCATION: (6)..(6)
<223> OTHER INFORMATION: Xaa = D-Trp
<220> FEATURE:
<221> NAME/KEY: MOD_RES
<222> LOCATION: (8)..(8)
<223> OTHER INFORMATION: modified with 4-Fl

<400> SEQUENCE: 24

Tyr Xaa Arg Phe Phe Xaa Lys Thr Phe
1               5

<210> SEQ ID NO 25
<211> LENGTH: 8
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with (D-6-methyl-8beta-
      ergolinylmethyl)thioacetyl (Dop1) in which the thioether group is
      modified to (SO2), via a psi(CH2NH) bond at the alpha-amino group
<220> FEATURE:
<221> NAME/KEY: MOD_RES
<222> LOCATION: (1)..(8)
<223> OTHER INFORMATION: cyclized with a lactam bridge

```
<220> FEATURE:
<221> NAME/KEY: MOD_RES
<222> LOCATION: (1)..(1)
<223> OTHER INFORMATION: Xaa = D-Lys
<220> FEATURE:
<221> NAME/KEY: MOD_RES
<222> LOCATION: (4)..(4)
<223> OTHER INFORMATION: Xaa = beta-(4-pyridinyl)alanine (4-Pal)
<220> FEATURE:
<221> NAME/KEY: MOD_RES
<222> LOCATION: (5)..(5)
<223> OTHER INFORMATION: Xaa = D-Trp

<400> SEQUENCE: 25

Xaa Arg Phe Xaa Xaa Lys Thr Tyr
 1               5

<210> SEQ ID NO 26
<211> LENGTH: 9
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with (D-6-methyl-8beta-
     ergolinylmethyl)thioacetyl (Dop1) in which the thioether group is
     modified to (SO2), via an amide bond at the alpha-amino group
<220> FEATURE:
<221> NAME/KEY: MOD_RES
<222> LOCATION: (1)..(2)
<223> OTHER INFORMATION: a psi(CH2NH) bond
<220> FEATURE:
<221> NAME/KEY: MOD_RES
<222> LOCATION: (2)..(9)
<223> OTHER INFORMATION: cyclized with a lactam bridge
<220> FEATURE:
<221> NAME/KEY: MOD_RES
<222> LOCATION: (2)..(2)
<223> OTHER INFORMATION: Xaa = D-Lys
<220> FEATURE:
<221> NAME/KEY: MOD_RES
<222> LOCATION: (5)..(5)
<223> OTHER INFORMATION: Xaa = beta-(4-pyridinyl)alanine (4-Pal)
<220> FEATURE:
<221> NAME/KEY: MOD_RES
<222> LOCATION: (6)..(6)
<223> OTHER INFORMATION: Xaa = D-Trp

<400> SEQUENCE: 26

Tyr Xaa Arg Phe Xaa Xaa Lys Thr Phe
 1               5

<210> SEQ ID NO 27
<211> LENGTH: 8
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with
     3-[N-(D-6-methyl-8beta-ergolinylmethyl)]-aminopropionyl via a
     psi(CH2NAc) bond at the alpha-amino group
<220> FEATURE:
<221> NAME/KEY: MOD_RES
<222> LOCATION: (1)..(8)
<223> OTHER INFORMATION: cyclized with a lactam bridge
<220> FEATURE:
<221> NAME/KEY: MOD_RES
<222> LOCATION: (1)..(1)
<223> OTHER INFORMATION: Xaa = D-Lys
<220> FEATURE:
```

```
<221> NAME/KEY: MOD_RES
<222> LOCATION: (5)..(5)
<223> OTHER INFORMATION: Xaa = D-Trp
<220> FEATURE:
<221> NAME/KEY: MOD_RES
<222> LOCATION: (8)..(8)
<223> OTHER INFORMATION: modified with 4-Fl

<400> SEQUENCE: 27

Xaa Arg Phe Phe Xaa Lys Thr Phe
1               5

<210> SEQ ID NO 28
<211> LENGTH: 8
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with (D-6-methyl-8beta-
      ergolinylmethyl)thioacetyl (Dop1) via a psi(CH2NH) bond at the
      alpha-amino group
<220> FEATURE:
<221> NAME/KEY: MOD_RES
<222> LOCATION: (1)..(8)
<223> OTHER INFORMATION: cyclized with a lactam bridge
<220> FEATURE:
<221> NAME/KEY: MOD_RES
<222> LOCATION: (1)..(1)
<223> OTHER INFORMATION: Xaa = D-Lys
<220> FEATURE:
<221> NAME/KEY: MOD_RES
<222> LOCATION: (4)..(4)
<223> OTHER INFORMATION: Xaa = beta-(4-pyridinyl)alanine (4-Pal)
<220> FEATURE:
<221> NAME/KEY: MOD_RES
<222> LOCATION: (5)..(5)
<223> OTHER INFORMATION: Xaa = D-Trp

<400> SEQUENCE: 28

Xaa Arg Phe Xaa Xaa Lys Thr Phe
1               5

<210> SEQ ID NO 29
<211> LENGTH: 8
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with (D-6-methyl-8beta-
      ergolinylmethyl)thioacetyl (Dop1) via an amide bond at the alpha-
      amino group
<220> FEATURE:
<221> NAME/KEY: MOD_RES
<222> LOCATION: (1)..(8)
<223> OTHER INFORMATION: cyclized with a lactam bridge
<220> FEATURE:
<221> NAME/KEY: MOD_RES
<222> LOCATION: (1)..(1)
<223> OTHER INFORMATION: Xaa = D-Lys
<220> FEATURE:
<221> NAME/KEY: MOD_RES
<222> LOCATION: (4)..(4)
<223> OTHER INFORMATION: Xaa = beta-(4-pyridinyl)alanine (4-Pal)
<220> FEATURE:
<221> NAME/KEY: MOD_RES
<222> LOCATION: (5)..(5)
<223> OTHER INFORMATION: Xaa = D-Trp
```

```
<400> SEQUENCE: 29

Xaa Arg Phe Xaa Xaa Lys Thr Phe
1               5

<210> SEQ ID NO 30
<211> LENGTH: 8
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with (D-6-methyl-8beta-
      ergolinylmethyl)thioacetyl (Dop1) via an amide bond at the alpha-
      amino group
<220> FEATURE:
<221> NAME/KEY: MOD_RES
<222> LOCATION: (1)..(8)
<223> OTHER INFORMATION: cyclized with a lactam bridge
<220> FEATURE:
<221> NAME/KEY: MOD_RES
<222> LOCATION: (1)..(1)
<223> OTHER INFORMATION: Xaa = D-Lys
<220> FEATURE:
<221> NAME/KEY: MOD_RES
<222> LOCATION: (4)..(4)
<223> OTHER INFORMATION: Xaa = beta-(4-pyridinyl)alanine (4-Pal)
<220> FEATURE:
<221> NAME/KEY: MOD_RES
<222> LOCATION: (5)..(5)
<223> OTHER INFORMATION: Xaa = D-Trp

<400> SEQUENCE: 30

Xaa Arg Phe Xaa Xaa Lys Thr Tyr
1               5

<210> SEQ ID NO 31
<211> LENGTH: 8
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with (D-6-methyl-8beta-
      ergolinylmethyl)thioacetyl (Dop1) via a psi(CH2NH) bond at the
      alpha-amino group
<220> FEATURE:
<221> NAME/KEY: MOD_RES
<222> LOCATION: (1)..(8)
<223> OTHER INFORMATION: cyclized with a lactam bridge
<220> FEATURE:
<221> NAME/KEY: MOD_RES
<222> LOCATION: (1)..(1)
<223> OTHER INFORMATION: Xaa = D-Lys
<220> FEATURE:
<221> NAME/KEY: MOD_RES
<222> LOCATION: (5)..(5)
<223> OTHER INFORMATION: Xaa = D-Trp

<400> SEQUENCE: 31

Xaa Arg Phe Phe Xaa Lys Thr Phe
1               5

<210> SEQ ID NO 32
<211> LENGTH: 9
<212> TYPE: PRT
<213> ORGANISM: Artificial Sequence
<220> FEATURE:
<223> OTHER INFORMATION: Somatostatin-dopamine chimeric peptide analog
```

```
<220> FEATURE:
<221> NAME/KEY: MOD_RES
<222> LOCATION: (1)..(1)
<223> OTHER INFORMATION: modified with 3-[N-acetyl-N-(D-6-methyl-8beta-
      ergolinylmethyl)]-aminopropionyl via an amide bond at the alpha-
      amino group
<220> FEATURE:
<221> NAME/KEY: MOD_RES
<222> LOCATION: (1)..(2)
<223> OTHER INFORMATION: a psi(CH2NH) bond
<220> FEATURE:
<221> NAME/KEY: MOD_RES
<222> LOCATION: (2)..(9)
<223> OTHER INFORMATION: cyclized with a lactam bridge
<220> FEATURE:
<221> NAME/KEY: MOD_RES
<222> LOCATION: (2)..(2)
<223> OTHER INFORMATION: Xaa = D-Lys
<220> FEATURE:
<221> NAME/KEY: MOD_RES
<222> LOCATION: (6)..(6)
<223> OTHER INFORMATION: Xaa = D-Trp
<220> FEATURE:
<221> NAME/KEY: MOD_RES
<222> LOCATION: (9)..(9)
<223> OTHER INFORMATION: modified with 4-Fl

<400> SEQUENCE: 32

Tyr Xaa Arg Phe Phe Xaa Lys Thr Phe
1               5

<210> SEQ ID NO 33
<211> LENGTH: 8
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with
      3-[N-acetyl-N-(D-6-methyl-8beta-ergolinylmethyl)]-aminopropionyl
      via a psi(CH2NAc) bond at the alpha-amino group
<220> FEATURE:
<221> NAME/KEY: MOD_RES
<222> LOCATION: (1)..(8)
<223> OTHER INFORMATION: cyclized with a lactam bridge
<220> FEATURE:
<221> NAME/KEY: MOD_RES
<222> LOCATION: (1)..(1)
<223> OTHER INFORMATION: Xaa = D-Lys
<220> FEATURE:
<221> NAME/KEY: MOD_RES
<222> LOCATION: (5)..(5)
<223> OTHER INFORMATION: Xaa = D-Trp
<220> FEATURE:
<221> NAME/KEY: MOD_RES
<222> LOCATION: (8)..(8)
<223> OTHER INFORMATION: modified with 4-Fl

<400> SEQUENCE: 33

Xaa Arg Phe Phe Xaa Lys Thr Phe
1               5

<210> SEQ ID NO 34
<211> LENGTH: 9
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
```

```
<222> LOCATION: (1)..(1)
<223> OTHER INFORMATION: modified with
      3-[N-acetyl-N-(D-6-methyl-8beta-ergolinylmethyl)]-aminopropionyl
      via a psi(CH2NH) bond at the alpha-amino group
<220> FEATURE:
<221> NAME/KEY: MOD_RES
<222> LOCATION: (1)..(2)
<223> OTHER INFORMATION: via a psi(CH2NH) bond
<220> FEATURE:
<221> NAME/KEY: MOD_RES
<222> LOCATION: (2)..(9)
<223> OTHER INFORMATION: cyclized with a lactam bridge
<220> FEATURE:
<221> NAME/KEY: MOD_RES
<222> LOCATION: (2)..(2)
<223> OTHER INFORMATION: Xaa = D-Lys
<220> FEATURE:
<221> NAME/KEY: MOD_RES
<222> LOCATION: (6)..(6)
<223> OTHER INFORMATION: Xaa = D-Trp
<220> FEATURE:
<221> NAME/KEY: MOD_RES
<222> LOCATION: (9)..(9)
<223> OTHER INFORMATION: modified with 4-Fl

<400> SEQUENCE: 34

Tyr Xaa Arg Phe Phe Xaa Lys Thr Phe
1               5

<210> SEQ ID NO 35
<211> LENGTH: 8
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with two (D-6-methyl-8beta-
      ergolinylmethyl)thioacetyl (Dop1) moieties via psi(CH2N) bonds at
      the alpha-amino group
<220> FEATURE:
<221> NAME/KEY: MOD_RES
<222> LOCATION: (1)..(8)
<223> OTHER INFORMATION: cyclized with a lactam bridge
<220> FEATURE:
<221> NAME/KEY: MOD_RES
<222> LOCATION: (1)..(1)
<223> OTHER INFORMATION: Xaa = D-Lys
<220> FEATURE:
<221> NAME/KEY: MOD_RES
<222> LOCATION: (4)..(4)
<223> OTHER INFORMATION: Xaa = beta-(4-pyridinyl)alanine (4-Pal)
<220> FEATURE:
<221> NAME/KEY: MOD_RES
<222> LOCATION: (5)..(5)
<223> OTHER INFORMATION: Xaa = D-Trp

<400> SEQUENCE: 35

Xaa Arg Phe Xaa Xaa Lys Thr Phe
1               5

<210> SEQ ID NO 36
<211> LENGTH: 8
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with
      3-[N-acetyl-N-(D-6-methyl-8beta-ergolinylmethyl)]-aminopropionyl
      via a psi(CH2NH) bond at the alpha-amino group
<220> FEATURE:
```

```
<221> NAME/KEY: MOD_RES
<222> LOCATION: (1)..(8)
<223> OTHER INFORMATION: cyclized with a lactam bridge
<220> FEATURE:
<221> NAME/KEY: MOD_RES
<222> LOCATION: (1)..(1)
<223> OTHER INFORMATION: Xaa = D-Lys
<220> FEATURE:
<221> NAME/KEY: MOD_RES
<222> LOCATION: (5)..(5)
<223> OTHER INFORMATION: Xaa = D-Trp
<220> FEATURE:
<221> NAME/KEY: MOD_RES
<222> LOCATION: (8)..(8)
<223> OTHER INFORMATION: modified with 4-Fl

<400> SEQUENCE: 36

Xaa Arg Phe Phe Xaa Lys Thr Phe
1               5

<210> SEQ ID NO 37
<211> LENGTH: 9
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with (D-6-methyl-8beta-
      ergolinylmethyl)thioacetyl (Dop1) via an amide bond at the alpha-
      amino group
<220> FEATURE:
<221> NAME/KEY: MOD_RES
<222> LOCATION: (1)..(2)
<223> OTHER INFORMATION: a psi(CH2NH) bond
<220> FEATURE:
<221> NAME/KEY: MOD_RES
<222> LOCATION: (2)..(9)
<223> OTHER INFORMATION: cyclized with a lactam bridge
<220> FEATURE:
<221> NAME/KEY: MOD_RES
<222> LOCATION: (2)..(2)
<223> OTHER INFORMATION: Xaa = D-ornithine (D-Orn)
<220> FEATURE:
<221> NAME/KEY: MOD_RES
<222> LOCATION: (6)..(6)
<223> OTHER INFORMATION: Xaa = D-Trp

<400> SEQUENCE: 37

Tyr Xaa Arg Phe Phe Xaa Lys Thr Phe
1               5

<210> SEQ ID NO 38
<211> LENGTH: 9
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with (D-6-methyl-8beta-
      ergolinylmethyl)thioacetyl (Dop1) via an amide bond at the alpha-
      amino group
<220> FEATURE:
<221> NAME/KEY: MOD_RES
<222> LOCATION: (1)..(2)
<223> OTHER INFORMATION: a psi(CH2NH) bond
<220> FEATURE:
<221> NAME/KEY: MOD_RES
<222> LOCATION: (2)..(9)
<223> OTHER INFORMATION: cyclized with a lactam bridge
<220> FEATURE:
<221> NAME/KEY: MOD_RES
```

```
<222> LOCATION: (6)..(6)
<223> OTHER INFORMATION: Xaa = D-Trp

<400> SEQUENCE: 38

Tyr Lys Arg Phe Phe Xaa Lys Thr Phe
1               5

<210> SEQ ID NO 39
<211> LENGTH: 9
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with (D-6-methyl-8beta-
      ergolinylmethyl)thioacetyl (Dop1) via an amide bond at the alpha-
      amino group
<220> FEATURE:
<221> NAME/KEY: MOD_RES
<222> LOCATION: (1)..(2)
<223> OTHER INFORMATION: a psi(CH2NH) bond
<220> FEATURE:
<221> NAME/KEY: MOD_RES
<222> LOCATION: (2)..(9)
<223> OTHER INFORMATION: cyclized with a lactam bridge
<220> FEATURE:
<221> NAME/KEY: MOD_RES
<222> LOCATION: (2)..(2)
<223> OTHER INFORMATION: Xaa = D-Lys
<220> FEATURE:
<221> NAME/KEY: MOD_RES
<222> LOCATION: (6)..(6)
<223> OTHER INFORMATION: Xaa = D-Trp

<400> SEQUENCE: 39

Tyr Xaa Arg Phe Phe Xaa Lys Thr Phe
1               5

<210> SEQ ID NO 40
<211> LENGTH: 9
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with (D-6-methyl-8beta-
      ergolinylmethyl)thioacetyl (Dop1) via an amide bond at the alpha-
      amino group
<220> FEATURE:
<221> NAME/KEY: MOD_RES
<222> LOCATION: (1)..(2)
<223> OTHER INFORMATION: a psi(CH2NH) bond
<220> FEATURE:
<221> NAME/KEY: MOD_RES
<222> LOCATION: (2)..(9)
<223> OTHER INFORMATION: cyclized with a lactam bridge
<220> FEATURE:
<221> NAME/KEY: MOD_RES
<222> LOCATION: (2)..(2)
<223> OTHER INFORMATION: Xaa = D-Lys
<220> FEATURE:
<221> NAME/KEY: MOD_RES
<222> LOCATION: (6)..(6)
<223> OTHER INFORMATION: Xaa = D-Trp

<400> SEQUENCE: 40

Tyr Xaa Arg Phe Phe Xaa Lys Thr Tyr
1               5
```

```
<210> SEQ ID NO 41
<211> LENGTH: 8
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with (D-6-methyl-8beta-
      ergolinylmethyl)thioacetyl (Dop1) via an amide bond at the alpha-
      amino group
<220> FEATURE:
<221> NAME/KEY: MOD_RES
<222> LOCATION: (1)..(8)
<223> OTHER INFORMATION: cyclized with a lactam bridge
<220> FEATURE:
<221> NAME/KEY: MOD_RES
<222> LOCATION: (1)..(1)
<223> OTHER INFORMATION: Xaa = D-Lys
<220> FEATURE:
<221> NAME/KEY: MOD_RES
<222> LOCATION: (5)..(5)
<223> OTHER INFORMATION: Xaa = D-Trp
<220> FEATURE:
<221> NAME/KEY: MOD_RES
<222> LOCATION: (8)..(8)
<223> OTHER INFORMATION: modified with 4-Fl

<400> SEQUENCE: 41

Xaa Arg Phe Phe Xaa Lys Thr Phe
1               5

<210> SEQ ID NO 42
<211> LENGTH: 8
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with two (D-6-methyl-8beta-
      ergolinylmethyl)thioacetyl (Dop1) moieties via psi(CH2N) bonds at
      the alpha-amino group
<220> FEATURE:
<221> NAME/KEY: MOD_RES
<222> LOCATION: (1)..(8)
<223> OTHER INFORMATION: cyclized with a lactam bridge
<220> FEATURE:
<221> NAME/KEY: MOD_RES
<222> LOCATION: (1)..(1)
<223> OTHER INFORMATION: Xaa = D-Lys
<220> FEATURE:
<221> NAME/KEY: MOD_RES
<222> LOCATION: (4)..(4)
<223> OTHER INFORMATION: Xaa = beta-(4-pyridinyl)alanine (4-Pal)
<220> FEATURE:
<221> NAME/KEY: MOD_RES
<222> LOCATION: (5)..(5)
<223> OTHER INFORMATION: Xaa = D-Trp

<400> SEQUENCE: 42

Xaa Arg Phe Xaa Xaa Lys Thr Tyr
1               5

<210> SEQ ID NO 43
<211> LENGTH: 9
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
```

```
<223> OTHER INFORMATION: modified with (D-6-methyl-8beta-
      ergolinylmethyl)thioacetyl (Dop1) via an amide bond at the alpha-
      amino group
<220> FEATURE:
<221> NAME/KEY: MOD_RES
<222> LOCATION: (1)..(1)
<223> OTHER INFORMATION: Xaa = D-Tyr
<220> FEATURE:
<221> NAME/KEY: MOD_RES
<222> LOCATION: (2)..(9)
<223> OTHER INFORMATION: cyclized with a lactam bridge
<220> FEATURE:
<221> NAME/KEY: MOD_RES
<222> LOCATION: (2)..(2)
<223> OTHER INFORMATION: Xaa = D-Lys
<220> FEATURE:
<221> NAME/KEY: MOD_RES
<222> LOCATION: (6)..(6)
<223> OTHER INFORMATION: Xaa = D-Trp

<400> SEQUENCE: 43

Xaa Xaa Arg Phe Phe Xaa Lys Thr Phe
1               5

<210> SEQ ID NO 44
<211> LENGTH: 9
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with (D-6-methyl-8beta-
      ergolinylmethyl)thioacetyl (Dop1) via an amide bond at the alpha-
      amino group
<220> FEATURE:
<221> NAME/KEY: MOD_RES
<222> LOCATION: (1)..(2)
<223> OTHER INFORMATION: a psi(CH2NH) bond
<220> FEATURE:
<221> NAME/KEY: MOD_RES
<222> LOCATION: (2)..(9)
<223> OTHER INFORMATION: cyclized with a lactam bridge
<220> FEATURE:
<221> NAME/KEY: MOD_RES
<222> LOCATION: (2)..(2)
<223> OTHER INFORMATION: Xaa = D-Lys
<220> FEATURE:
<221> NAME/KEY: MOD_RES
<222> LOCATION: (5)..(5)
<223> OTHER INFORMATION: Xaa = beta-(3-pyridinyl)alanine (3-Pal)
<220> FEATURE:
<221> NAME/KEY: MOD_RES
<222> LOCATION: (6)..(6)
<223> OTHER INFORMATION: Xaa = D-Trp

<400> SEQUENCE: 44

Tyr Xaa Arg Phe Xaa Xaa Lys Thr Phe
1               5

<210> SEQ ID NO 45
<211> LENGTH: 8
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with two (D-6-methyl-8beta-
      ergolinylmethyl)thioacetyl (Dop1) moieties via psi(CH2N) bonds at
      the alpha-amino group
<220> FEATURE:
<221> NAME/KEY: MOD_RES
```

```
<222> LOCATION: (1)..(8)
<223> OTHER INFORMATION: cyclized with a lactam bridge
<220> FEATURE:
<221> NAME/KEY: MOD_RES
<222> LOCATION: (1)..(1)
<223> OTHER INFORMATION: Xaa = D-Lys
<220> FEATURE:
<221> NAME/KEY: MOD_RES
<222> LOCATION: (5)..(5)
<223> OTHER INFORMATION: Xaa = D-Trp
<220> FEATURE:
<221> NAME/KEY: MOD_RES
<222> LOCATION: (8)..(8)
<223> OTHER INFORMATION: modified with 4-Fl

<400> SEQUENCE: 45

Xaa Arg Phe Phe Xaa Lys Thr Phe
1               5

<210> SEQ ID NO 46
<211> LENGTH: 8
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with two (D-6-methyl-8beta-
      ergolinylmethyl)thioacetyl (Dop1) moieties via psi(CH2N) bonds at
      the alpha-amino group
<220> FEATURE:
<221> NAME/KEY: MOD_RES
<222> LOCATION: (1)..(8)
<223> OTHER INFORMATION: cyclized with a lactam bridge
<220> FEATURE:
<221> NAME/KEY: MOD_RES
<222> LOCATION: (1)..(1)
<223> OTHER INFORMATION: Xaa = D-Lys
<220> FEATURE:
<221> NAME/KEY: MOD_RES
<222> LOCATION: (5)..(5)
<223> OTHER INFORMATION: Xaa = D-Trp

<400> SEQUENCE: 46

Xaa Arg Phe Phe Xaa Lys Thr Phe
1               5

<210> SEQ ID NO 47
<211> LENGTH: 9
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with (D-6-methyl-8beta-
      ergolinylmethyl)thioacetyl (Dop1) via an amide bond at the alpha-
      amino group
<220> FEATURE:
<221> NAME/KEY: MOD_RES
<222> LOCATION: (1)..(2)
<223> OTHER INFORMATION: a psi(CH2NH) bond
<220> FEATURE:
<221> NAME/KEY: MOD_RES
<222> LOCATION: (1)..(1)
<223> OTHER INFORMATION: Xaa = D-Tyr
<220> FEATURE:
<221> NAME/KEY: MOD_RES
<222> LOCATION: (2)..(9)
<223> OTHER INFORMATION: cyclized with a lactam bridge
<220> FEATURE:
<221> NAME/KEY: MOD_RES
<222> LOCATION: (2)..(2)
```

```
<223> OTHER INFORMATION: Xaa = D-Lys
<220> FEATURE:
<221> NAME/KEY: MOD_RES
<222> LOCATION: (6)..(6)
<223> OTHER INFORMATION: Xaa = D-Trp

<400> SEQUENCE: 47

Xaa Xaa Arg Phe Phe Xaa Lys Thr Phe
1               5

<210> SEQ ID NO 48
<211> LENGTH: 9
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with
      [N-(D-6-methyl-8beta-ergolinylmethyl)-N-(methylsulfonyl)]-
      aminopropionyl via an amide bond at the alpha-amino group
<220> FEATURE:
<221> NAME/KEY: MOD_RES
<222> LOCATION: (1)..(2)
<223> OTHER INFORMATION: a psi(CH2NH) bond
<220> FEATURE:
<221> NAME/KEY: MOD_RES
<222> LOCATION: (2)..(9)
<223> OTHER INFORMATION: cyclized with a lactam bridge
<220> FEATURE:
<221> NAME/KEY: MOD_RES
<222> LOCATION: (2)..(2)
<223> OTHER INFORMATION: Xaa = D-Lys
<220> FEATURE:
<221> NAME/KEY: MOD_RES
<222> LOCATION: (6)..(6)
<223> OTHER INFORMATION: Xaa = D-Trp
<220> FEATURE:
<221> NAME/KEY: MOD_RES
<222> LOCATION: (9)..(9)
<223> OTHER INFORMATION: modified with 4-Fl

<400> SEQUENCE: 48

Tyr Xaa Arg Phe Phe Xaa Lys Thr Phe
1               5

<210> SEQ ID NO 49
<211> LENGTH: 9
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with (D-6-methyl-8beta-
      ergolinylmethyl)thioacetyl (Dop1) via an amide bond at the alpha-
      amino group
<220> FEATURE:
<221> NAME/KEY: MOD_RES
<222> LOCATION: (1)..(2)
<223> OTHER INFORMATION: a psi(CH2NH) bond
<220> FEATURE:
<221> NAME/KEY: MOD_RES
<222> LOCATION: (2)..(9)
<223> OTHER INFORMATION: cyclized with a lactam bridge
<220> FEATURE:
<221> NAME/KEY: MOD_RES
<222> LOCATION: (2)..(2)
<223> OTHER INFORMATION: Xaa = ornithine (Orn)
<220> FEATURE:
<221> NAME/KEY: MOD_RES
<222> LOCATION: (6)..(6)
<223> OTHER INFORMATION: Xaa = D-Trp
```

```
<400> SEQUENCE: 49

Tyr Xaa Arg Phe Phe Xaa Lys Thr Phe
1               5

<210> SEQ ID NO 50
<211> LENGTH: 8
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with (D-6-methyl-8beta-
      ergolinylmethyl)thioacetyl (Dop1) via an amide bond at the alpha-
      amino group
<220> FEATURE:
<221> NAME/KEY: MOD_RES
<222> LOCATION: (1)..(8)
<223> OTHER INFORMATION: cyclized with a lactam bridge
<220> FEATURE:
<221> NAME/KEY: MOD_RES
<222> LOCATION: (1)..(1)
<223> OTHER INFORMATION: Xaa = D-Lys
<220> FEATURE:
<221> NAME/KEY: MOD_RES
<222> LOCATION: (5)..(5)
<223> OTHER INFORMATION: Xaa = D-Trp

<400> SEQUENCE: 50

Xaa Arg Phe Phe Xaa Lys Thr Phe
1               5

<210> SEQ ID NO 51
<211> LENGTH: 9
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with (D-6-methyl-8beta-
      ergolinylmethyl)thioacetyl (Dop1) via an amide bond at the alpha-
      amino group
<220> FEATURE:
<221> NAME/KEY: MOD_RES
<222> LOCATION: (1)..(2)
<223> OTHER INFORMATION: a psi(CH2NH) bond
<220> FEATURE:
<221> NAME/KEY: MOD_RES
<222> LOCATION: (1)..(1)
<223> OTHER INFORMATION: Xaa = D-Tyr
<220> FEATURE:
<221> NAME/KEY: MOD_RES
<222> LOCATION: (2)..(9)
<223> OTHER INFORMATION: cyclized with a lactam bridge
<220> FEATURE:
<221> NAME/KEY: MOD_RES
<222> LOCATION: (2)..(2)
<223> OTHER INFORMATION: Xaa = D-Lys
<220> FEATURE:
<221> NAME/KEY: MOD_RES
<222> LOCATION: (4)..(4)
<223> OTHER INFORMATION: Xaa = beta-(4-pyridinyl)alanine (4-Pal)
<220> FEATURE:
<221> NAME/KEY: MOD_RES
<222> LOCATION: (6)..(6)
<223> OTHER INFORMATION: Xaa = D-Trp

<400> SEQUENCE: 51

Xaa Xaa Arg Xaa Tyr Xaa Lys Thr Phe
1               5
```

```
<210> SEQ ID NO 52
<211> LENGTH: 9
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with (D-6-methyl-8beta-
      ergolinylmethyl)thioacetyl (Dop1) via an amide bond at the alpha-
      amino group
<220> FEATURE:
<221> NAME/KEY: MOD_RES
<222> LOCATION: (1)..(1)
<223> OTHER INFORMATION: modified with (D-6-methyl-8beta-
      ergolinylmethyl)thioacetyl (Dop1) via an amide bond at the
      epsilon-amino group
<220> FEATURE:
<221> NAME/KEY: MOD_RES
<222> LOCATION: (1)..(2)
<223> OTHER INFORMATION: a psi(CH2NH) bond
<220> FEATURE:
<221> NAME/KEY: MOD_RES
<222> LOCATION: (2)..(9)
<223> OTHER INFORMATION: cyclized with a lactam bridge
<220> FEATURE:
<221> NAME/KEY: MOD_RES
<222> LOCATION: (2)..(2)
<223> OTHER INFORMATION: Xaa = D-Lys
<220> FEATURE:
<221> NAME/KEY: MOD_RES
<222> LOCATION: (6)..(6)
<223> OTHER INFORMATION: Xaa = D-Trp
<220> FEATURE:
<221> NAME/KEY: MOD_RES
<222> LOCATION: (9)..(9)
<223> OTHER INFORMATION: modified with 4-Fl

<400> SEQUENCE: 52

Lys Xaa Arg Phe Phe Xaa Lys Thr Phe
1               5

<210> SEQ ID NO 53
<211> LENGTH: 8
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with [D-6-methyl-8beta-
      ergolinylmethyl]-sulfonylpropyl
<220> FEATURE:
<221> NAME/KEY: MOD_RES
<222> LOCATION: (1)..(8)
<223> OTHER INFORMATION: cyclized with a lactam bridge
<220> FEATURE:
<221> NAME/KEY: MOD_RES
<222> LOCATION: (1)..(1)
<223> OTHER INFORMATION: Xaa = D-Lys
<220> FEATURE:
<221> NAME/KEY: MOD_RES
<222> LOCATION: (5)..(5)
<223> OTHER INFORMATION: Xaa = D-Trp
<220> FEATURE:
<221> NAME/KEY: MOD_RES
<222> LOCATION: (8)..(8)
<223> OTHER INFORMATION: modified with 4-Fl

<400> SEQUENCE: 53

Xaa Arg Phe Phe Xaa Lys Thr Phe
1               5
```

```
<210> SEQ ID NO 54
<211> LENGTH: 9
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: labeled with 125-Iodine
<220> FEATURE:
<221> NAME/KEY: MOD_RES
<222> LOCATION: (2)..(2)
<223> OTHER INFORMATION: Xaa = D-Phe
<220> FEATURE:
<221> NAME/KEY: MOD_RES
<222> LOCATION: (3)..(8)
<223> OTHER INFORMATION: cyclized with a lactam bridge
<220> FEATURE:
<221> NAME/KEY: MOD_RES
<222> LOCATION: (5)..(5)
<223> OTHER INFORMATION: Xaa = D-Trp
<220> FEATURE:
<221> NAME/KEY: MOD_RES
<222> LOCATION: (9)..(9)
<223> OTHER INFORMATION: AMIDATION

<400> SEQUENCE: 54

Tyr Xaa Cys Tyr Xaa Lys Val Cys Thr
1               5

<210> SEQ ID NO 55
<211> LENGTH: 8
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with (D-6-methyl-8beta-
     ergolinylmethyl)thioacetyl (Dop1)
<220> FEATURE:
<221> NAME/KEY: MOD_RES
<222> LOCATION: (1)..(8)
<223> OTHER INFORMATION: cyclized with a lactam bridge
<220> FEATURE:
<221> NAME/KEY: MOD_RES
<222> LOCATION: (1)..(1)
<223> OTHER INFORMATION: Xaa = D-2,4-diaminobutyric acid (D-Dab)
<220> FEATURE:
<221> NAME/KEY: MOD_RES
<222> LOCATION: (5)..(5)
<223> OTHER INFORMATION: Xaa = D-Trp

<400> SEQUENCE: 55

Xaa Arg Phe Phe Xaa Lys Thr Phe
1               5

<210> SEQ ID NO 56
<211> LENGTH: 9
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with (D-6-methyl-8beta-
     ergolinylmethyl)thioacetyl (Dop1)
<220> FEATURE:
<221> NAME/KEY: MOD_RES
<222> LOCATION: (2)..(9)
```

```
<223> OTHER INFORMATION: cyclized with a lactam bridge
<220> FEATURE:
<221> NAME/KEY: MOD_RES
<222> LOCATION: (2)..(2)
<223> OTHER INFORMATION: Xaa = D-2,4-diaminobutyric acid (D-Dab)
<220> FEATURE:
<221> NAME/KEY: MOD_RES
<222> LOCATION: (6)..(6)
<223> OTHER INFORMATION: Xaa = D-Trp

<400> SEQUENCE: 56

Tyr Xaa Arg Phe Phe Xaa Lys Thr Phe
1               5

<210> SEQ ID NO 57
<211> LENGTH: 9
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: modified with (D-6-methyl-8beta-
      ergolinylmethyl)thioacetyl (Dop1) via an amide bond at the alpha-
      amino group
<220> FEATURE:
<221> NAME/KEY: MOD_RES
<222> LOCATION: (1)..(1)
<223> OTHER INFORMATION: modified with (D-6-methyl-8beta-
      ergolinylmethyl)thioacetyl (Dop1) via an amide bond at the
      epsilon-amino group
<220> FEATURE:
<221> NAME/KEY: MOD_RES
<222> LOCATION: (2)..(9)
<223> OTHER INFORMATION: cyclized with a lactam bridge
<220> FEATURE:
<221> NAME/KEY: MOD_RES
<222> LOCATION: (2)..(2)
<223> OTHER INFORMATION: Xaa = D-2,4-diaminobutyric acid (D-Dab)
<220> FEATURE:
<221> NAME/KEY: MOD_RES
<222> LOCATION: (6)..(6)
<223> OTHER INFORMATION: Xaa = D-Trp

<400> SEQUENCE: 57

Lys Xaa Arg Phe Phe Xaa Lys Thr Phe
1               5

<210> SEQ ID NO 58
<211> LENGTH: 9
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: Xaa = D-Tyr or Tyr or D-Lys or Lys or deleted
<220> FEATURE:
<221> NAME/KEY: MOD_RES
<222> LOCATION: (2)..(2)
<223> OTHER INFORMATION: Xaa = D-Lys
<220> FEATURE:
<221> NAME/KEY: MOD_RES
<222> LOCATION: (2)..(9)
<223> OTHER INFORMATION: cyclized with a lactam bridge
<220> FEATURE:
<221> NAME/KEY: MOD_RES
<222> LOCATION: (5)..(5)
<223> OTHER INFORMATION: Xaa = Phe or beta-(2-pyridinyl)alanine (2-Pal)
      or beta-(3-pyridinyl)alanine (3-Pal) or beta-(4-pyridinyl)alanine
      (4-Pal)
<220> FEATURE:
<221> NAME/KEY: MOD_RES
```

```
<222> LOCATION: (6)..(6)
<223> OTHER INFORMATION: Xaa = D-Trp
<220> FEATURE:
<221> NAME/KEY: MOD_RES
<222> LOCATION: (9)..(9)
<223> OTHER INFORMATION: Xaa = Phe or 2-FPhe or 3-FPhe or 4-FPhe or 3,4-
      FPhe or 3,5-FPhe or 2,3,4,5,6-FPhe or Tyr

<400> SEQUENCE: 58

Xaa Xaa Arg Phe Xaa Xaa Lys Thr Xaa
1               5

<210> SEQ ID NO 59
<211> LENGTH: 9
<212> TYPE: PRT
<213> ORGANISM: Artificial Sequence
<220> FEATURE:
<223> OTHER INFORMATION: Somatostatin-dopamine chimeric peptide analog
<220> FEATURE:
<221> NAME/KEY: MOD_RES
<222> LOCATION: (1)..(1)
<223> OTHER INFORMATION: Xaa = D-Tyr or Tyr or D-Lys or Lys or deleted
<220> FEATURE:
<221> NAME/KEY: MOD_RES
<222> LOCATION: (1)..(2)
<223> OTHER INFORMATION: a pseudopeptide bond
<220> FEATURE:
<221> NAME/KEY: MOD_RES
<222> LOCATION: (2)..(2)
<223> OTHER INFORMATION: Xaa = D-Lys
<220> FEATURE:
<221> NAME/KEY: MOD_RES
<222> LOCATION: (2)..(9)
<223> OTHER INFORMATION: cyclized with a lactam bridge
<220> FEATURE:
<221> NAME/KEY: MOD_RES
<222> LOCATION: (5)..(5)
<223> OTHER INFORMATION: Xaa = Phe or beta-(2-pyridinyl)alanine (2-Pal)
      or beta-(3-pyridinyl)alanine (3-Pal) or beta-(4-pyridinyl)alanine
      (4-Pal)
<220> FEATURE:
<221> NAME/KEY: MOD_RES
<222> LOCATION: (6)..(6)
<223> OTHER INFORMATION: Xaa = D-Trp
<220> FEATURE:
<221> NAME/KEY: MOD_RES
<222> LOCATION: (9)..(9)
<223> OTHER INFORMATION: Xaa = Phe or 2-FPhe or 3-FPhe or 4-FPhe or
      3,4-FPhe or 3,5-FPhe or 2,3,4,5,6-FPhe or Tyr

<400> SEQUENCE: 59

Xaa Xaa Arg Phe Xaa Xaa Lys Thr Xaa
1               5
```

SOMATOSTATIN-DOPAMINE CHIMERIC ANALOGS

FIELD OF THE INVENTION

The present invention relates to novel somatostatin-dopamine chimeric analogs having improved activity and uses thereof in, inter alia, the inhibition, prevention, and/or treatment of neuroendocrine tumors, neoplasia, acromegaly, Cushing's disease/syndrome and/or other conditions.

SEQUENCE LISTING

The instant application contains a Sequence Listing which has been submitted in ASCII format via EFS-Web, and is hereby incorporated by reference in its entirety. The ASCII copy, is named "V4_225_Seq_Listing_V6_corrected_ST25.txt", created Sep. 2, 2015, and has the file size of 42 KB. This text file serves as both the paper copy required by 37 CFR 1.821(c) and the computer readable form (CRF) required by 37 CFR 1.821(e).

BACKGROUND OF THE INVENTION

Naturally occurring somatostatins (SSTs), which are also known as somatotropin release-inhibiting factors (SRIFs), have diverse biological effects in many cells and organs throughout the body. They are produced by normal endocrine, gastrointestinal, immune and neuronal cells, as well as by certain tumors (Patel, Y. C., *Frontiers in Neuroendocrinology*, 20(3): 157-198 (1999); Froidevaux, et al., *Biopolymers*, 66(3): 161-83 (2002)). The effects of somatostatins are broadly inhibitory on the secretion of hormones, as well as on the proliferation and survival of cells. They inhibit both endocrine secretion (e.g., growth hormone, insulin, glucagon, gastrin, cholecystokinin, vasoactive intestinal peptide, and secretin) and exocrine secretion (e.g., gastric acid, intestinal fluid and pancreatic enzymes) (Patel. Y. C., (1999) op. cit.). Somatostatins also inhibit proliferation of both normal and tumor cells (Bousquet, et al., *Chemotherapy*, 47(2): 30-39 (2001)).

These biological effects of somatostatins, all inhibitory in nature, are elicited through a series of G protein-coupled receptors, of which five different subtypes have been characterized (SSTR1-5) (Reubi, et al., *Cancer Res*, 47: 551-558 (1987); Reisine, et al., *Endocrine Review*, 16: 427-442 (1995); Patel, Y. C., (1999) op. cit.). SSTR1-5 have similar affinities for the endogenous somatostatin ligands but have differing distribution in various tissues.

Somatostatin analogs were initially developed for the control of hormonal syndromes associated with neuroendocrine tumors (NETs). In recent years, accumulating data has supported their role as antiproliferative agents, capable of stabilizing tumor growth in patients with metastatic neuroendocrine malignancies, including carcinoid and pancreatic endocrine tumors (Strosberg, et al., *World J Gastroenterol*, 26(24): 2963-2970 (2010)).

Examples of somatostatin analogs are disclosed in, e.g., PCT publication Nos. WO 02/10215; WO 2007/144492; WO 2010/037930; WO 99/22735; and WO 03/014158.

Dopamine is a catecholamine neurotransmitter that has been implicated in the pathogenesis of both Parkinson's disease and schizophrenia (Graybiel, et al., *Adv. Neurol.*, 53: 17-29 (1990); Goldstein, et al., *FASEB Journal*, 6: 2413-2421 (1992); Olanow, et al., *Annu. Rev. Neurosci.*, 22, 123-144 (1999)). Dopamine and related molecules have been shown to inhibit the growth of several types of malignant tumors in mice, and this activity has been variously attributed to inhibition of tumor-cell proliferation, stimulation of tumor immunity or effects on melanin metabolism in malignant melanomas. (Wick, M. M., *J. Invest. Dermatol.*, 71: 163-164 (1978); Wick, M. M., *J. Natl. Cancer Inst.*, 63: 1465-1467 (1979); Wick, M. M., *Cancer Treat Rep.*, 63: 991-997 (1979); Basu, et al., *Endocrine*, 12: 237-241 (2000); Basu, et al., *J. Neuroimmunol.*, 102: 113-124 (2000)).

It has been shown that dopamine receptor subtype DRD2 and somatostatin receptor subtype SSTR2, as well as other somatostatin receptor subtypes and members of the dopamine and opiate receptor families, interact physically through hetero-oligomerization to create a novel receptor with enhanced functional activity (Rocheville, et al., *Science*, 288(5463): 154-157 (2000); Baragli, et al., *Hetero-oligomerization of dopamine (D2R) and SST receptors (SSTR2) in CHO—K1 cells and cortical cultured neurons*, Proc. 85$^{th}$ Endo. Soc. Meeting, Philadelphia, Pa., USA (2003) (Abstract P2-669); Pfeiffer, et al., *J. Biol. Chem.*, 277: 19762-19772 (2002)).

A combination of basic research observations concerning the interaction of somatostatin and dopamine receptors and clinical reports of enhanced efficacy of combined somatostatin and dopamine analog treatment in suppressing growth hormone hypersecretion led to the concept of creating chimeric molecules combining structural features of both compound classes. Examples of somatostatin-dopamine chimeric molecules are disclosed in U.S. patent application publication No. US 2004/0209798 and PCT publication Nos. WO 2004/091490, WO 2002/100888, and WO 2009/139855.

Exemplary somatostatin-dopamine chimeric molecules are taught in the art to retain the ability to interact with receptors of both families and display greatly enhanced potency and efficacy, as compared with that of individual SST or DA receptor agonists. In vitro studies with pituitary adenoma cells from acromegalic patients have demonstrated that the chimeric molecules have exceptional activity with regard to suppression of growth hormone and prolactin secretion by pituitary adenoma cells from acromegalic patients (Saveanu, et al., *J Clin Endocrinol Metab*, 87(12): 5545-5552 (2002); Jaquet, et al., *European Journal of Endocrinology*, 153: 135-141 (2005)). Similarly, potent suppression of ACTH secretion from Cushing's-causing corticotroph tumors, and suppression of nonfunctioning pituitary adenoma proliferation has been observed (Florio, et al., *Endocrine-Related Cancer*, 15: 583-596 (2008)). The somatostatin-dopamine chimeric compounds are also quite potent and efficacious in suppressing both growth hormone and IGF1 in vivo when tested in nonhuman primates, with no effect on either insulin secretion or glycemic control (Culler, et al., *The somatostatin-dopamine chimeric molecule, BIM-23A760, does not induce the insulin/glycemic effects observed with individual somatostatin or dopamine agonists in cynomolgus monkeys (Macaca fascicularis)*, 12th Meeting of the European Neuroendocrine Association, Athens, Greece (2006)).

Initial clinical studies examining acute, subcutaneous administration of select somatostatin-dopamine chimeric compounds revealed both prolonged circulating half-life and extended duration of biological effect (Culler, M., *Horm Metab Res*, 43(12): 854-857 (2011)). With chronic administration, however, select somatostatin-dopamine chimeric compounds were found to produce a metabolite with dopaminergic activity that gradually accumulates and interferes with the activity of the parent compound (Culler, M., (2011) op. cit.).

Clearly, needs remain for additional somatostatin-dopamine chimeric analogs having improved activity for use in, inter alia, the inhibition, prevention, and/or treatment of neuroendocrine tumors and/or diseases.

SUMMARY OF THE INVENTION

The present invention is based on the discovery of improved somatostatin-dopamine chimeric analogs, that is, chimeric compounds that retain both somatostatin and dopamine activity. Preferred somatostatin-dopamine chimeric analogs of the invention show a level of activity in comparison to certain previously reported somatostatin-dopamine compounds that make them promising additions to the developing family of somatostatin-dopamine analogs.

The improved somatostatin-dopamine chimeric analogs of the invention are considered to be useful, e.g., in vitro, for use as research tools, diagnostic assays, etc., or in vivo, for use as diagnostic or therapeutic agents. Preferred chimeric analogs of the invention display enhanced activity when compared to native somatostatin and dopamine, either alone or in combination and particularly display enhanced activity compared to the somatostatin-dopamine chimeric analogs previously reported.

The present invention provides a novel series of somatostatin-dopamine chimeric compounds having at least one moiety which binds to one or more dopamine receptor subtypes and a somatostatin analog moiety according to Formula I (SEQ ID NO:58), and pharmaceutically acceptable salts thereof:

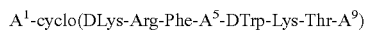
$A^1$-cyclo(DLys-Arg-Phe-$A^5$-DTrp-Lys-Thr-$A^9$)    (I)

wherein:
$A^1$ is DTyr, Tyr, DLys, Lys, or absent;
$A^5$ is Phe, 2Pal, 3Pal, or 4Pal; and
$A^9$ is Phe, 2FPhe, 3FPhe, 4FPhe, 3,4FPhe, 3,5FPhe, 2,3,4,5,6FPhe, or Tyr;

wherein said at least one moiety which binds to one or more dopamine receptor subtypes is, independently for each occurrence, attached to the N-terminal amine group, or an internal amine or hydroxyl group, of said somatostatin analog moiety according to Formula I.

Additionally, the present invention provides a novel series of somatostatin-dopamine chimeric compounds having at least one moiety which binds to one or more dopamine receptor subtypes and a somatostatin analog moiety according to Formula II (SEQ ID NO:59), and pharmaceutically acceptable salts thereof:

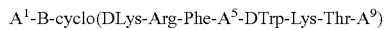
$A^1$-B-cyclo(DLys-Arg-Phe-$A^5$-DTrp-Lys-Thr-$A^9$)    (II)

wherein:
$A^1$ is DTyr, Tyr, DLys, Lys, or absent;
B is a pseudopeptide bond;
$A^5$ is Phe, 2Pal, 3Pal, or 4Pal; and
$A^9$ is Phe, 2FPhe, 3FPhe, 4FPhe, 3,4FPhe, 3,5FPhe, 2,3,4,5,6FPhe, or Tyr;

wherein said at least one moiety which binds to one or more dopamine receptor subtypes is, independently for each occurrence, attached to the N-terminal amine group, or an internal amine or hydroxyl group, of said somatostatin analog moiety according to Formula II.

According to a preferred embodiment of the present invention, said pseudopeptide bond according to Formula II is psi($CH_2NR$), as defined herein, wherein R is H, $(C_{1-10})$alkyl, substituted $(C_{1-10})$alkyl, $(C_{1-10})$heteroalkyl, substituted $(C_{1-10})$heteroalkyl, $(C_{2-10})$alkenyl, substituted $(C_{2-10})$alkenyl, $(C_{2-10})$alkynyl, substituted $(C_{2-10})$alkynyl, aryl, alkylaryl, substituted alkylaryl, arylalkyl, substituted arylalkyl, $(C_{2-10})$acyl, substituted $(C_{2-10})$acyl, or a moiety which binds to one or more dopamine receptor subtypes, e.g., Dop1, Dop1(SO), or Dop1($SO_2$), as defined herein, or any of these moieties whose carbonyl group has been modified to $CH_2$.

In a particular embodiment of the present invention, said somatostatin-dopamine chimeric compounds are according to Formula III, and pharmaceutically acceptable salts thereof:

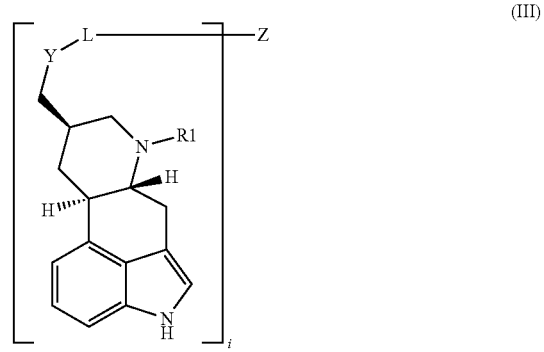

wherein:
Z is said somatostatin analog moiety according to Formula I or Formula II;
Y is —O—, —C(O)—, —S—, —O—$(CH_2)_n$—C(O)—, —S—$(CH_2)_n$—C(O)—, —S(O)—, —S(O)$_2$—, —S—C(O)—, —O—C(O)—, —N($R^5$)—C(O)—, —N($R^5$)S(O)$_2$—, or —N($R^6$)—;
L is —$(CH_2)_n$—C(O)— or —$(CH_2)_n$—;
i is 1 or 2;
n is 1-10;
R1 is $(C_{1-3})$alkyl; and
$R^5$ and $R^6$ each is, independently for each occurrence, H, $(C_{1-10})$alkyl, substituted $(C_{1-10})$alkyl, $(C_{1-10})$heteroalkyl, substituted $(C_{1-10})$heteroalkyl, $(C_{2-10})$alkenyl, substituted $(C_{2-10})$alkenyl, $(C_{2-10})$alkynyl, substituted $(C_{2-10})$alkynyl, aryl, alkylaryl, substituted alkylaryl, arylalkyl, substituted arylalkyl, $(C_{2-10})$acyl, or substituted $(C_{2-10})$acyl;

wherein each moiety depicted between the brackets is, independently for each occurrence, attached to the N-terminal amine group, or an internal amine or hydroxyl group, of Z.

In another particular embodiment of the present invention, said somatostatin-dopamine chimeric compounds are according to Formula IIIa, and pharmaceutically acceptable salts thereof:

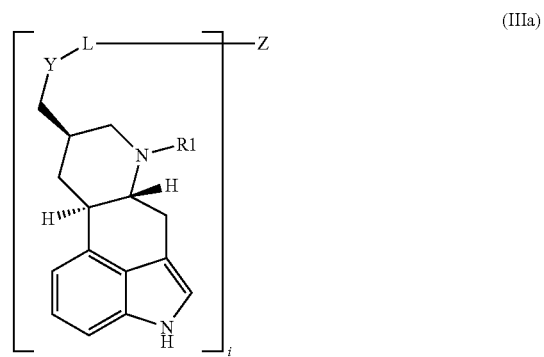

wherein:
Z is said somatostatin analog moiety according to Formula I or Formula II;
Y is —O—, —C(O)—, —S—, —O—$(CH_2)_n$—C(O)—, —S—$(CH_2)_n$—C(O)—, —S(O)—, —S(O)$_2$—, —S—C(O)—, —O—C(O)—, —N($R^5$)—C(O)—, —N($R^5$)S(O)$_2$—, —N($R^6$)—, or absent;
L is —$(CH_2)_n$—C(O)— or —$(CH_2)_n$—;
i is 1 or 2;
n is 1-10;
R1 is ($C_{1-3}$)alkyl; and
$R^5$ and $R^6$ each is, independently for each occurrence, H, ($C_{1-10}$)alkyl, substituted ($C_{1-10}$)alkyl, ($C_{1-10}$)heteroalkyl, substituted ($C_{1-10}$)heteroalkyl, ($C_{2-10}$)alkenyl, substituted ($C_{2-10}$)alkenyl, ($C_{2-10}$)alkynyl, substituted ($C_{2-10}$)alkynyl, aryl, alkylaryl, substituted alkylaryl, arylalkyl, substituted arylalkyl, ($C_{2-10}$)acyl, or substituted ($C_{2-10}$)acyl;
wherein each moiety depicted between the brackets is, independently for each occurrence, attached to the N-terminal amine group, or an internal amine or hydroxyl group, of Z.

The present invention further provides pharmaceutical compositions comprising the somatostatin-dopamine chimeric compounds of the invention.

The present invention further provides in vitro and in vivo uses of the claimed compounds and pharmaceutical compositions.

DETAILED DESCRIPTION OF THE INVENTION

Definitions

Figure 1:
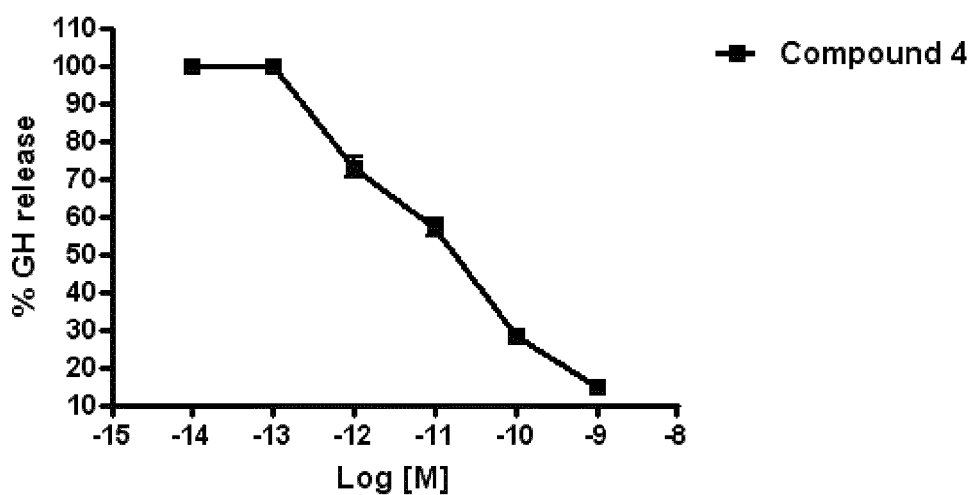
FIG. 1 is a graph showing the Growth hormone suppressing activity of Compound 4 (see Table I hereinbelow for its chemical name and its corresponding structural representation) on pituitary tumor cells of acromegalic patients presenting with macroadenoma. Various concentrations of Compound 4 were added to the medium and the cells were incubated for 18 hours before measurement of Growth hormone levels in the medium using the AlphaLISA Growth Hormone Immunoassay Research kit (PerkinElmer).
Figure 2:
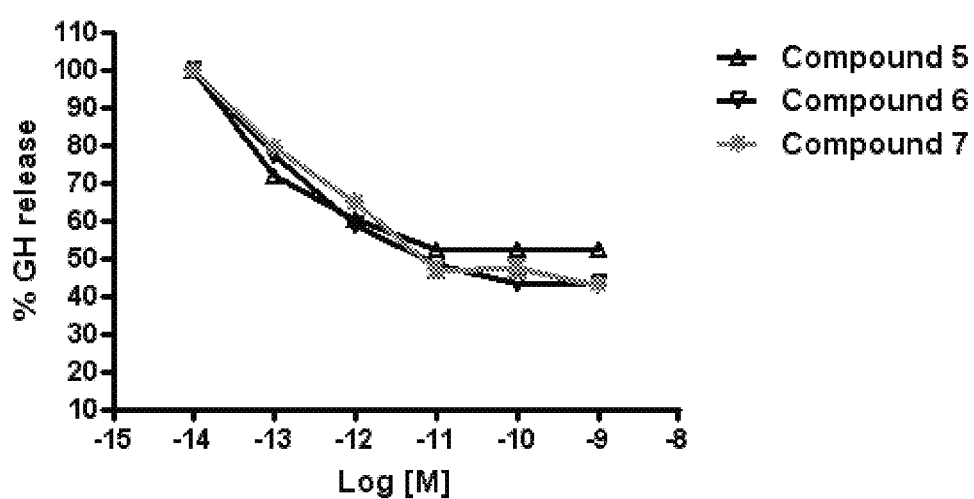
FIG. 2 is a graph showing the Growth hormone suppressing activity of Compounds 5, 6, and 7 (see Table I hereinbelow for their chemical name and their corresponding structural representation) on pituitary tumor cells of acromegalic patients presenting with macroadenoma. Various concentrations of Compounds 5, 6, and 7 were added to the medium and the cells were incubated for 18 hours before measurement of Growth hormone levels in the medium using the AlphaLISA Growth Hormone Immunoassay Research kit (PerkinElmer).
Figure 3:
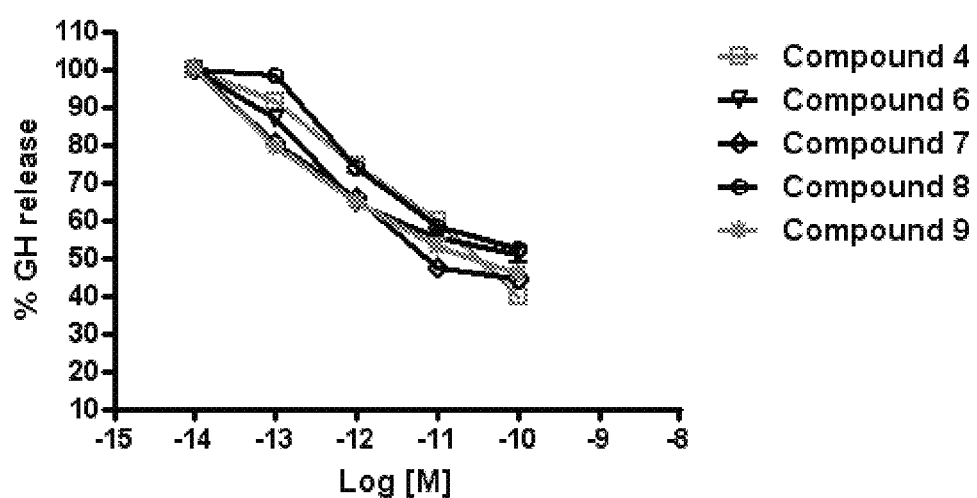
FIG. 3 is a graph showing the Growth hormone suppressing activity of Compounds 4, 6, 7, 8, and 9 (see Table I hereinbelow for their chemical name and their corresponding structural representation) on pituitary tumor cells of acromegalic patients presenting with macroadenoma. Various concentrations of Compounds 4, 6, 7, 8, and 9 were added to the medium and the cells were incubated for 18 hours before measurement of Growth hormone levels in the medium using the AlphaLISA Growth Hormone Immunoassay Research kit (PerkinElmer).
Figure 4:
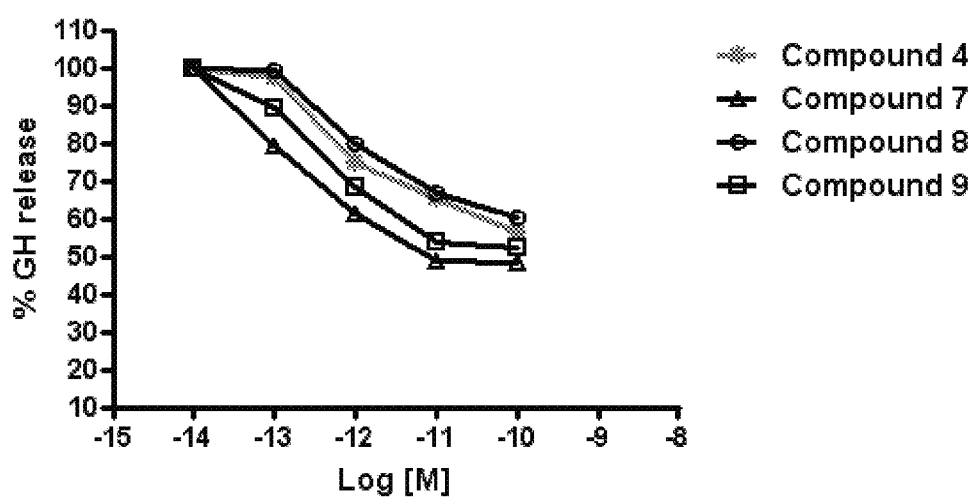
FIG. 4 is a graph showing the Growth hormone suppressing activity of Compounds 4, 7, 8, and 9 (see Table I hereinbelow for their chemical name and their corresponding structural representation) on pituitary tumor cells of acromegalic patients presenting with macroadenoma. Various concentrations of Compounds 4, 7, 8, and 9 were added to the medium and the cells were incubated for 18 hours before measurement of Growth hormone levels in the medium using the AlphaLISA Growth Hormone Immunoassay Research kit (PerkinElmer).

The nomenclature used to define the peptides is that typically used in the art wherein the amino group at the N-terminus appears to the left and the carboxyl group at the C-terminus appears to the right. Where an amino acid has isomeric forms, it is the L form of the amino acid that is represented unless otherwise explicitly indicated, e.g., "DLys" for D-lysine.

Lines between amino acid residues, unless otherwise defined, represent peptide bonds between the amino acid residues. The Greek letter ψ, designated herein as "psi", is used herein to indicate that a peptide bond (i.e., amide bond) has been replaced by a pseudopeptide bond (e.g., reduced amide bond). As used herein, the format of the psi term is X-psi($CH_2NR$)—X', wherein X is an amino acyl radical or an acyl radical, e.g., Dop1, Dop1(SO), or Dop1($SO_2$), as defined herein, whose carbonyl group has been modified to $CH_2$, and wherein X' is an amino acyl radical whose α-amino group has been modified to NR, wherein R is, e.g., H, ($C_{1-10}$)alkyl, ($C_{2-10}$)acyl, or a moiety which binds to one or more dopamine receptor subtypes, e.g., Dop1, Dop1(SO), or Dop1($SO_2$), as defined herein, or any of these moieties whose carbonyl group has been modified to $CH_2$. For example, if X is Dop1 whose carbonyl group has been modified to $CH_2$, and if R is acetyl, then X-psi($CH_2NR$)—X' is provided as "Dop1-psi($CH_2NAc$)—X'". For another example, if X and R are both Dop1 whose carbonyl group has been modified to $CH_2$, then X-psi($CH_2NR$)—X' is provided as "bis[Dop1-psi($CH_2N$)]—X'", wherein the pseudopeptide bond is designated as Dop1-psi($CH_2N$) in which Dop1 corresponds to R in the formula X-psi($CH_2NR$)—X'. The nature of the pseudopeptide bond in the instance of bis[Dop1-psi($CH_2N$)]—X' should be made more clear by referring to the pictorial representation of the term "bis[Dop1-psi($CH_2N$)]—X'" as provided hereinbelow.

The term "Dop1", as used herein, means a compound having the chemical name (D-6-methyl-8β-ergolinylmethyl)thioacetyl and having the following structure:

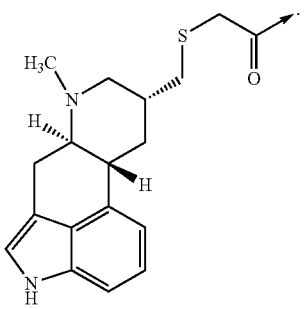

The term "Dop1-psi(CH$_2$NH)—X'", as used herein, means a compound having the following structure:

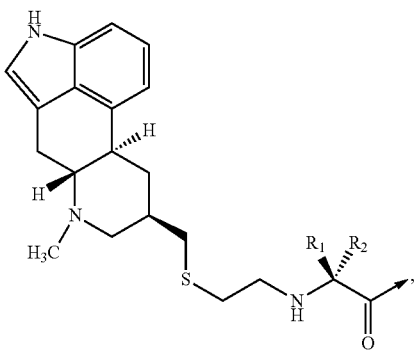

wherein the term "X'" is an amino acyl radical of the formula

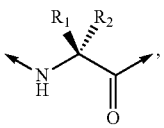

wherein R$_1$ and R$_2$ each is, independently for each occurrence, hydrogen or the side chain of an amino acid (e.g., R$_1$=CH$_3$ and R$_2$=H, for alanine).

The term "bis[Dop1-psi(CH$_2$N)]—X'", as used herein, means a compound having the following structure:

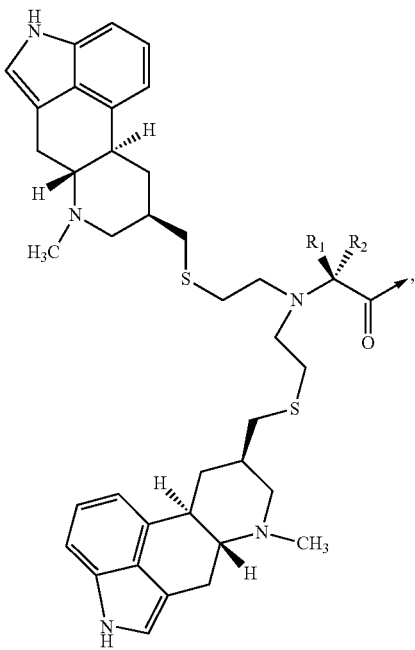

wherein the term "X'" is an amino acyl radical of the formula

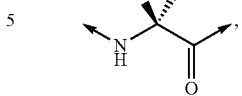

wherein R$_1$ and R$_2$ each is, independently for each occurrence, hydrogen or the side chain of an amino acid.

The term "Dop1(SO$_2$)", as used herein, means a compound having the following structure:

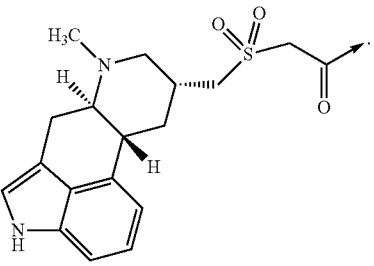

The term "Dop1(SO$_2$)-psi(CH$_2$NH)—X'", as used herein, means a compound having the following structure:

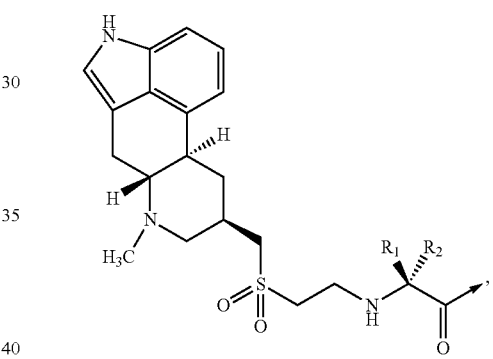

wherein the term "X'" is an amino acyl radical of the formula

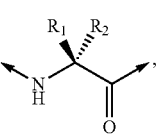

wherein R$_1$ and R$_2$ each is, independently for each occurrence, hydrogen or the side chain of an amino acid.

The term "Dop1(SO)", as used herein, means a compound having the following structure:

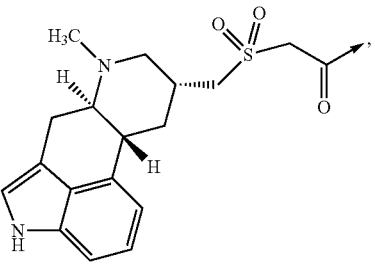

wherein, unless stereochemistry at the sulfur atom is specified, a compound represented by this term is either Dop1 [(R)SO], i.e.,

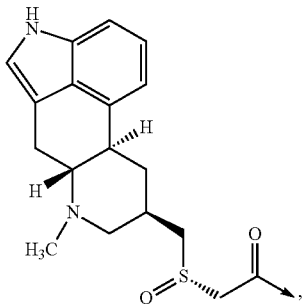

or Dop1[(S)SO], i.e.,

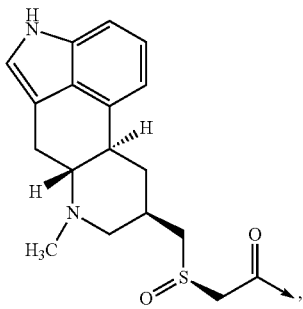

or a diastereomeric mixture comprising Dop1[(R)SO] and Dop1[(S)SO].

The term "Dop1(SO)-psi(CH₂NH)—X'", as used herein, means a compound having the following structure:

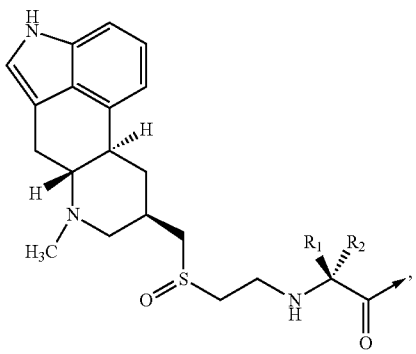

wherein the term "X'" is an amino acyl radical of the formula

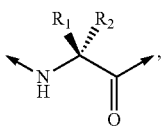

wherein R₁ and R₂ each is, independently for each occurrence, hydrogen or the side chain of an amino acid, and wherein, unless stereochemistry at the sulfur atom is specified, a compound represented by this term is either Dop1 [(R)SO]-psi(CH₂NH)—X', i.e.

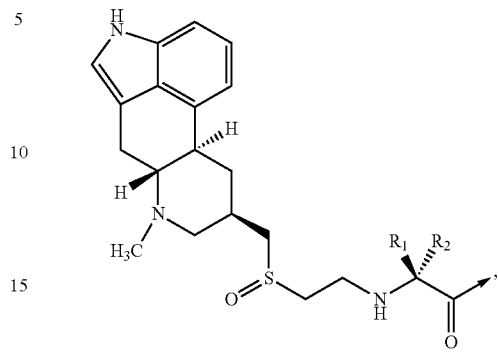

or Dop1[(S)SO]-psi(CH₂NH)—X', i.e.,

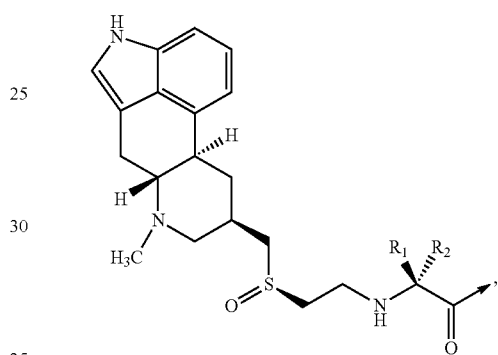

or a diastereomeric mixture comprising Dop1[(R)SO]-psi (CH₂NH)—X' and Dop1[(S)SO]-psi(CH₂NH)—X'.

Some of the compounds of the instant invention have at least one asymmetric center. Additional asymmetric centers may be present in the molecule depending upon the nature of the various substituents of the molecule. Each such asymmetric center will produce two optical isomers and it is intended that all such optical isomers, as separated, pure or partially purified optical isomers, racemic mixtures or diastereomeric mixtures thereof, are included within the scope of the instant invention.

By a "somatostatin receptor agonist" is meant a compound that has a high binding affinity (e.g., $K_i$ of less than 100 nM, or preferably less than 10 nM, or more preferably less than 1 nM) for a somatostatin receptor (e.g., as defined by the receptor binding assay described below), such as any of the different subtypes: e.g., SSTR1, SSTR2, SSTR3, SSTR4, and SSTR5, and elicits a somatostatin-like effect; for example, in an assay for the inhibition of cAMP intracellular production.

By a "somatostatin selective agonist" is meant a somatostatin receptor agonist which has a higher binding affinity (e.g., lower $K_i$) and/or potency (e.g., low $EC_{50}$) for one somatostatin receptor subtype than for any other somatostatin receptor subtype, such as, for example, a somatostatin SSTR2 selective agonist.

By a "dopamine receptor agonist" is meant a compound that has a high binding affinity (e.g., $K_i$ of less than 100 nM, or preferably less than 10 nM, or more preferably less than 1 nM) for a dopamine receptor (e.g., as defined by the receptor binding assay described below), such as any of the different subtypes: e.g., D1, D2, D3, D4, and D5 receptors, and elicits a dopamine-like effect; for example, in an assay for the inhibition of cAMP intracellular production.

By "somatostatin receptor agonist effect" is meant a ligand after binding to the somatostatin receptor activates the somatostatin receptor-mediated signaling pathway(s).

By "dopamine receptor agonist effect" is meant a ligand after binding to the dopamine receptor activates the dopamine receptor-mediated signaling pathway(s).

By "alkyl", e.g., $(C_{1-10})$alkyl, is meant a hydrocarbon group containing one or more carbon atoms, where multiple carbon atoms if present are joined by single bonds. The alkyl hydrocarbon group may be straight-chain or contain one or more branches or cyclic groups.

By "substituted alkyl", e.g., substituted $(C_{1-10})$alkyl, is meant an alkyl wherein one or more hydrogen atoms of the hydrocarbon group are replaced with one or more substituents selected from the group consisting of halogen (i.e., fluorine, chlorine, bromine, and iodine), —OH, —CN, —SH, —NH$_2$, —NHCH$_3$, —NO$_2$, —$(C_{1-2})$alkyl substituted with 1 to 5 halogens, —CF$_3$, —OCH$_3$, —OCF$_3$, and —(CH$_2$)$_{0-4}$—COOH. In different embodiments 1, 2, 3 or 4 substituents are present. The presence of —(CH$_2$)$_{0-4}$—COOH results in the production of an alkyl acid. Examples of alkyl acids containing, or consisting of, —(CH$_2$)$_{0-4}$—COOH include 2-norbornane acetic acid, tert-butyric acid and 3-cyclopentyl propionic acid.

By "heteroalkyl", e.g., $(C_{1-10})$heteroalkyl, is meant an alkyl wherein one of more of the carbon atoms in the hydrocarbon group are replaced with one or more of the following groups: amino, amido, —O—, or carbonyl. In different embodiments 1 or 2 heteroatoms are present.

By "substituted heteroalkyl", e.g., substituted $(C_{1-10})$heteroalkyl, is meant a heteroalkyl wherein one or more hydrogen atoms of the hydrocarbon group are replaced with one or more substituents selected from the group consisting of halogen, (i.e., fluorine, chlorine, bromine, and iodine), —OH, —CN, —SH, —NH$_2$, —NHCH$_3$, —NO$_2$, —$(C_{1-2})$alkyl substituted with 1 to 5 halogens, —CF$_3$, —OCH$_3$, —OCF$_3$, and —(CH$_2$)$_{0-4}$—COOH. In different embodiments 1, 2, 3 or 4 substituents are present.

By "alkenyl", e.g., $(C_{2-10})$alkenyl, is meant a hydrocarbon group made up of two or more carbons where one or more carbon-carbon double bonds are present. The alkenyl hydrocarbon group may be straight-chain or contain one or more branches or cyclic groups.

By "substituted alkenyl", e.g., substituted $(C_{2-10})$alkenyl, is meant an alkenyl wherein one or more hydrogen atoms of the hydrocarbon group are replaced with one or more substituents selected from the group consisting of halogen, (i.e., fluorine, chlorine, bromine, and iodine), —OH, —CN, —SH, —NH$_2$, —NHCH$_3$, —NO$_2$, —$(C_{1-2})$alkyl substituted with 1 to 5 halogens, —CF$_3$, —OCH$_3$, —OCF$_3$, and —(CH$_2$)$_{0-4}$—COOH. In different embodiments 1, 2, 3 or 4 substituents are present.

By "alkynyl", e.g., $(C_{2-10})$alkynyl, is meant a hydrocarbon group made up of two or more carbons where one or more carbon-carbon triple bonds are present. The alkynyl hydrocarbon group may be straight-chain or contain one or more branches or cyclic groups.

By "substituted alkynyl", e.g., substituted $(C_{2-10})$alkynyl, is meant an alkynyl wherein one or more hydrogen atoms of the hydrocarbon group are replaced with one or more substituents selected from the group consisting of a halogen (i.e., fluorine, chlorine, bromine, and iodine), —OH, —CN, —SH, —NH$_2$, —NHCH$_3$, —NO$_2$, —$(C_{1-2})$alkyl substituted with 1 to 5 halogens, —CF$_3$, —OCH$_3$, —OCF$_3$, and —(CH$_2$)$_{0-4}$—COOH. In different embodiments 1, 2, 3 or 4 substituents are present.

By "aryl" is meant an optionally substituted aromatic group with at least one ring having a conjugated pi-electron system, containing up to two conjugated or fused ring systems. An aryl includes carbocyclic aryl, heterocyclic aryl and biaryl groups. Preferably, the aryl is a 5 or 6 membered ring. Preferred atoms for a heterocyclic aryl are one or more sulfur, oxygen, and/or nitrogen. Examples of aryl include phenyl, 1-naphthyl, 2-naphthyl, indole, and quinoline, 2-imidazole, and 9-anthracene. Aryl substituents are selected from the group consisting of —C$_{1-4}$ alkyl, —C$_{1-4}$ alkoxy, halogen (i.e., fluorine, chlorine, bromine, and iodine), —OH, —CN, —SH, —NH$_2$, —NO$_2$, —$(C_{1-2})$alkyl substituted with 1 to 5 halogens, —CF$_3$, —OCF$_3$, and —(CH$_2$)$_{0-4}$—COOH. In different embodiments the aryl contains 0, 1, 2, 3, or 4 substituents.

By "acyl", e.g., $(C_{2-10})$acyl, is meant X'—R"—C(O)—, where R" is alkyl, substituted alkyl, heteroalkyl, substituted heteroalkyl, alkenyl, substituted alkenyl, alkynyl, substituted alkynyl, aryl, alkylaryl, or substituted alklyaryl and X' is H or absent.

By "arylalkyl" or "alkylaryl" is meant an "alkyl" joined to an "aryl".

A composition or method described herein as "comprising" one or more named elements or steps is open-ended, meaning that the named elements or steps are essential, but other elements or steps may be added within the scope of the composition or method. To avoid prolixity, it is also understood that any composition or method described as "comprising" (or which "comprises") one or more named elements or steps also describes the corresponding, more limited composition or method "consisting essentially of" (or which "consists essentially of") the same named elements or steps, meaning that the composition or method includes the named essential elements or steps and may also include additional elements or steps that do not materially affect the basic and novel characteristics of the composition or method. It is also understood that any composition or method described herein as "comprising" or "consisting essentially of" one or more named elements or steps also describes the corresponding, more limited, and closed-ended composition or method "consisting of" (or which "consists of") the named elements or steps to the exclusion of any other unnamed element or step. In any composition or method disclosed herein, known or disclosed equivalents of any named essential element or step may be substituted for that element or step. It is also understood that an element or step "selected from the group consisting of" refers to one or more of the elements or steps in the list that follows, including combinations of any two or more of the listed elements or steps.

In the context of therapeutic use of the somatostatin-dopamine chimeric compounds described herein, the terms "treatment", "to treat", or "treating" will refer to any use of the compounds calculated or intended to correct or reduce the disease condition(s) of patients, e.g., to arrest or inhibit the growth or proliferation of neuroendocrine tumors and/or alleviation of a symptom of neuroendocrine disease and other conditions. Thus, treating an individual may be carried out after any diagnosis indicating possible presence of neuroendocrine tumor or neuroendocrine disease.

The meaning of other terms will be understood by the context as understood by the skilled practitioner in the art, including the fields of organic chemistry, pharmacology, and physiology.

Abbreviations

In Formulas I and II, and in the chemical names as listed in Table I, the following abbreviations for amino acids are used: "Lys" for lysine; "Arg" for arginine; "Phe" for phenylalanine; "Trp" for tryptophan; "Thr" for threonine; "2Pal" for β-(2-pyridinyl)alanine; "3Pal" for β-(3-pyridinyl)alanine; "4Pal" for β-(4-pyridinyl)alanine; "Tyr" for tyrosine; "2FPhe, 3FPhe, 4FPhe, 3,4FPhe, 3,5FPhe, or 2,3,4,5,6FPhe" for phenylalanine fluorinated at each of the designated positions of the phenyl ring; and "Orn" for ornithine.

Certain abbreviations used herein are defined as follows:
By "Boc" is meant tert-butyloxycarbonyl.
By "BSA" is meant bovine serum albumin.
By "Bzl" is meant benzyl.
By "DCM" is meant dichloromethane.
By "DIC" is meant N,N-diisopropylcarbodiimide.
By "DIEA" is meant diisopropylethyl amine.
By "Dmab" is meant 4-{N-[1-(4,4-dimethyl-2,6-dioxocyclohexylidene)-3-methylbutyl]-amino}benzyl.
By "DMAP" is meant 4-(dimethylamino)pyridine.
By "DMF" is meant dimethylformamide.
By "DNP" is meant 2,4-dinitrophenyl.
By "DTT" is meant dithiothreitol.
By "ESI-MS" is meant electrospray Ionization mass spectrometry.
By "FBS" is meant fetal bovine serum.
By "Fmoc" is meant fluorenylmethyloxycarbonyl.
By "HBTU" is meant 2-(1-H-benzotriazole-1-yl)-1,1,3,3-tetramethyluronium hexafluorophosphate.
By "HOBt" is meant 1-hydroxy-benzotriazole.
By "LAH" is meant lithium aluminum hydride.
By "NMP" is meant N-methylpyrrolidone.
By "Pbf" is meant 2,2,4,6,7-pentamethyldihydrobenzofuran-5-sulfonyl.
By "PBS" is meant phosphate-buffered saline.
By "PyAOP" is meant (7-azabenzotriazol-1-yloxy)tripyrrolidinophosphonium hexafluorophosphate).
By "PyBOP" is meant benzotriazol-1-yl-oxytripyrrolidinophosphonium hexafluorophosphate.
By "tBu" is meant tert-butyl.
By "TIS" is meant triisopropylsilane.
By "Trt" is meant trityl.
By "TFA" is meant trifluoroacetic acid.

Embodiments of the Invention

In the compounds of Formulas I, II, III, and IIIa, $A^1$ is DTyr, Tyr, DLys, Lys, or absent. In some embodiments, $A^1$ is Tyr, Lys, or absent. In some embodiments, $A^1$ is Tyr or Lys. In some embodiments, $A^1$ is Tyr or absent. In some embodiments, $A^1$ is Lys or absent. In certain particular embodiments, $A^1$ is absent. In certain other particular embodiments, $A^1$ is Tyr.

In the compounds of Formulas I, II, III, and IIIa, $A^5$ is Phe, 2Pal, 3Pal, or 4Pal. In some embodiments, $A^5$ is Phe or 4Pal. In certain particular embodiments $A^5$ is 4Pal.

In the compounds of Formulas I, II, III, and IIIa, $A^9$ is Phe, 2FPhe, 3FPhe, 4FPhe, 3,4FPhe, 3,5FPhe, 2,3,4,5,6FPhe, or Tyr. In some embodiments, $A^9$ is Phe, 4FPhe, or Tyr. In certain particular embodiments, $A^9$ is Tyr.

In the compounds of Formulas II, III, and IIIa, B is a pseudopeptide bond. In some embodiments, B is -psi(CH$_2$NH)— or -psi(CH$_2$NR)—, wherein R is $(C_{1-10})$alkyl, substituted $(C_{1-10})$alkyl, $(C_{2-10})$heteroalkyl, substituted $(C_{1-10})$heteroalkyl, $(C_{2-10})$alkenyl, substituted $(C_{2-10})$alkenyl, $(C_{2-10})$alkynyl, substituted $(C_{2-10})$alkynyl, aryl, alkylaryl, substituted alkylaryl, arylalkyl, substituted arylalkyl, $(C_{2-10})$acyl, substituted $(C_{2-10})$acyl, or a moiety which binds to one or more dopamine receptor subtypes. In some embodiments, R is $(C_{1-3})$alkyl, $(C_{2-4})$acyl, or Dop1 whose carbonyl group has been modified to CH$_2$. In some embodiments, B is psi(CH$_2$NH), psi(CH$_2$NAc), or Dop1-psi(CH$_2$N). In some embodiments, B is -psi(CH$_2$NH)— or -psi(CH$_2$NAc)—. In certain particular embodiments, B is -psi(CH$_2$NH)—. In certain particular embodiments, B is -psi(CH$_2$NR)—, wherein R is Dop1 whose carbonyl group has been modified to CH$_2$.

In the compounds of Formulas III and IIIa, R1 is $(C_{1-3})$alkyl. In certain particular embodiments, R1 is —CH$_3$.

In the compounds of Formulas III and IIIa, Y is —O—, —C(O)—, —S—, —O—(CH$_2$)$_n$—C(O)—, —S—(CH$_2$)$_n$—C(O)—, —S(O)—, —S(O)$_2$—, —S—C(O)—, —O—C(O)—, —N(R$^5$)—C(O)—, —N(R$^5$)S(O)$_2$—, —N(R$^6$)—, or absent. In some embodiments, Y is —S—, —S(O)—, —S(O)$_2$—, —N(R$^5$)—C(O)—, or —N(R$^6$)—. In some embodiments, Y is —S—, —S(O)—, or —S(O)$_2$—. In some other embodiments, Y is —N(R$^5$)—C(O)— or —N(R$^6$)—. In certain embodiments, Y is —S— or —S(O)—. In certain particular embodiments, Y is —S—.

In the compounds of Formulas III and IIIa, $R^5$ and $R^6$ each is, independently for each occurrence, H, $(C_{1-10})$alkyl, substituted $(C_{1-10})$alkyl, $(C_{1-10})$heteroalkyl, substituted $(C_{1-10})$heteroalkyl, $(C_{2-10})$alkenyl, substituted $(C_{2-10})$alkenyl, $(C_{2-10})$alkynyl, substituted $(C_{2-10})$alkynyl, aryl, alkylaryl, substituted alkylaryl, arylalkyl, substituted arylalkyl, $(C_{2-10})$acyl, or substituted $(C_{2-10})$acyl. In some embodiments, $R^5$ is, independently for each occurrence, H, $(C_{1-4})$alkyl, substituted $(C_{1-4})$alkyl, $(C_{2-4})$heteroalkyl, substituted $(C_{2-4})$heteroalkyl, $(C_{2-4})$alkenyl, substituted $(C_{2-4})$alkenyl, $(C_{2-4})$alkynyl, substituted $(C_{2-4})$alkynyl, aryl, or arylalkyl. In some embodiments, $R^5$ is, independently for each occurrence, H or —CH$_3$. In some embodiments, $R^6$ is, independently for each occurrence, H, $(C_{1-4})$alkyl, substituted $(C_{1-4})$alkyl, $(C_{2-4})$heteroalkyl, substituted $(C_{2-4})$heteroalkyl, $(C_{2-4})$alkenyl, substituted $(C_{2-4})$alkenyl, $(C_{2-4})$alkynyl, substituted $(C_{2-4})$alkynyl, aryl, arylalkyl, or $(C_{2-4})$acyl. In some embodiments. $R^6$ is, independently for each occurrence, H, —CH$_3$ or Ac.

In the compounds of Formulas III and IIIa, L is —(CH$_2$)$_n$—C(O)— or —(CH$_2$)$_n$—, where n is 1-10. In some embodiments, n is 1-5. In some embodiments, n is 1-2. In certain embodiments, L is —(CH$_2$)—C(O)—, —(CH$_2$)—, or —(CH$_2$)$_2$—. In certain particular embodiments, L is —(CH$_2$)—.

According to a preferred embodiment of the present invention, said somatostatin-dopamine chimeric compounds according to Formulas I, II and III are characterized in that:
R1 is —CH$_3$;
Y is —S—, —S(O)—, —S(O)$_2$—, or —N(R$^5$)—S(O)$_2$—;
L is —CH$_2$—C(O)— or —(CH$_2$)$_2$—;
$A^1$ is Tyr, Lys, or absent;
B is psi(CH$_2$NH);
$A^5$ is Phe or 4Pal; and
$A^9$ is Phe, 4FPhe, or Tyr.

According to a particularly preferred embodiment of the present invention, said somatostatin-dopamine chimeric compounds according to Formulas I, II and III are characterized in that:

R1 is —CH₃;
Y is —S—, —S(O)—, —S(O)₂—, or —N(R⁵)—S(O)₂—;
L is —CH₂—C(O)— or —(CH₂)₂—;
A¹ is Tyr or Lys;
B is psi(CH₂NH);
A⁵ is 4Pal; and
A⁹ is Phe.

According to another particularly preferred embodiment of the present invention, said somatostatin-dopamine chimeric compounds according to Formulas I, II and III are characterized in that:
R1 is —CH₃;
Y is —S—, —S(O)—, —S(O)₂—, or —N(R⁵)—S(O)₂—;
L is —CH₂—C(O)— or —(CH₂)₂—;
A¹ is Tyr or absent;
B is psi(CH₂NH);
A⁵ is Phe; and
A⁹ is 4FPhe.

According to another particularly preferred embodiment of the present invention, said somatostatin-dopamine chimeric compounds according to Formulas I, II and III are characterized in that:
R1 is —CH₃;
Y is —S—, —S(O)—, —S(O)₂—, or —N(R⁵)—S(O)₂—;
L is —CH₂—C(O)— or —(CH₂)₂—;
A¹ is Lys or absent;
B is psi(CH₂NH);
A⁵ is 4Pal; and
A⁹ is Tyr.

According to another preferred embodiment of the present invention, said somatostatin-dopamine chimeric compounds according to Formulas I, II and III are characterized in that:
R1 is —CH₃;
Y is —S—, —S(O)—, —S(O)₂—, —N(R⁵)S(O)₂—, or —N(R⁶)—;
L is —(CH₂)—C(O)—, or —(CH₂)₂—; and
A¹ is Tyr, Lys, or absent.

According to another preferred embodiment of the present invention, said somatostatin-dopamine chimeric compounds according to Formulas I, II and III are characterized in that:
R1 is —CH₃;
Y is —S—, —S(O)—, —S(O)₂—, —N(R⁵)S(O)₂—, or —N(R⁶)—;
L is —(CH₂)—C(O)—, or —(CH₂)₂—; and
A¹ is Tyr or Lys.

According to another preferred embodiment of the present invention, said somatostatin-dopamine chimeric compounds according to Formulas I, II and III are characterized in that:
R1 is —CH₃;
Y is —S—, —S(O)—, —S(O)₂—, —N(R⁵)S(O)₂—, or —N(R⁶)—;
L is —(CH₂)—C(O)—, or —(CH₂)₂—; and
A¹ is Tyr or absent.

According to another preferred embodiment of the present invention, said somatostatin-dopamine chimeric compounds according to Formulas I, II and III are characterized in that:
R1 is —CH₃;
Y is —S—, —S(O)—, —S(O)₂—, —N(R⁵)S(O)₂—, or —N(R⁶)—;
L is —(CH₂)—C(O)—, or —(CH₂)₂—; and
A¹ is Lys or absent.

According to another preferred embodiment of the present invention, said somatostatin-dopamine chimeric compounds according to Formulas I, II and III are characterized in that:
R1 is —CH₃;
Y is —S—, —S(O)—, —S(O)₂—, —N(R⁵)S(O)₂—, or —N(R⁶)—;
L is —(CH₂)—C(O)—, or —(CH₂)₂—; and
A¹ is absent.

According to a preferred embodiment of the present invention, said somatostatin-dopamine chimeric compounds according to Formulas I, II and III are characterized in that:
R1 is —CH₃;
Y is —S—, —S(O)—, or —S(O)₂—;
L is —(CH₂)—C(O)—, or —(CH₂)₂—; and
A¹ is Tyr, Lys, or absent.

According to another preferred embodiment of the present invention, said somatostatin-dopamine chimeric compounds according to Formulas I, II and III are characterized in that:
R1 is —CH₃;
Y is —S—, —S(O)—, or —S(O)₂—;
L is —(CH₂)—C(O)—, or —(CH₂)₂—; and
A¹ is Tyr or Lys.

According to another preferred embodiment of the present invention, said somatostatin-dopamine chimeric compounds according to Formulas I, II and III are characterized in that:
R1 is —CH₃;
Y is —S—, —S(O)—, or —S(O)₂—;
L is —(CH₂)—C(O)—, or —(CH₂)₂—; and
A¹ is Tyr or absent.

According to another preferred embodiment of the present invention, said somatostatin-dopamine chimeric compounds according to Formulas I, II and III are characterized in that:
R1 is —CH₃;
Y is —S—, —S(O)—, or —S(O)₂—;
L is —(CH₂)—C(O)—, or —(CH₂)₂—; and
A¹ is Lys or absent.

According to another preferred embodiment of the present invention, said somatostatin-dopamine chimeric compounds according to Formulas I, II and III are characterized in that:
R1 is —CH₃;
Y is —S—, —S(O)—, or —S(O)₂—;
L is —(CH₂)—C(O)—, or —(CH₂)₂—; and
A¹ is absent.

According to a preferred embodiment of the present invention, said somatostatin-dopamine chimeric compounds according to Formulas I, II and III are characterized in that:
R1 is —CH₃;
Y is —S— or —S(O)—;
L is —(CH₂)—C(O)—, or —(CH₂)₂—; and
A¹ is Tyr, Lys, or absent.

According to another preferred embodiment of the present invention, said somatostatin-dopamine chimeric compounds according to Formulas I, II and III are characterized in that:
R1 is —CH₃;
Y is —S— or —S(O)—;
L is —(CH₂)—C(O)—, or —(CH₂)₂—; and
A¹ is Tyr or Lys.

According to another preferred embodiment of the present invention, said somatostatin-dopamine chimeric compounds according to Formulas I, II and III are characterized in that:
R1 is —CH$_3$;
Y is —S— or —S(O)—;
L is —(CH$_2$)—C(O)—, or —(CH$_2$)$_2$—; and
A$^1$ is Tyr or absent.

According to another preferred embodiment of the present invention, said somatostatin-dopamine chimeric compounds according to Formulas I, II and III are characterized in that:
R1 is —CH$_3$;
Y is —S— or —S(O)—;
L is —(CH$_2$)—C(O)—, or —(CH$_2$)$_2$—; and
A$^1$ is Lys or absent.

According to another preferred embodiment of the present invention, said somatostatin-dopamine chimeric compounds according to Formulas I, II and III are characterized in that:
R1 is —CH$_3$;
Y is —S— or —S(O)—;
L is —(CH$_2$)—C(O)—, or —(CH$_2$)$_2$—; and
A$^1$ is absent.

According to a preferred embodiment of the present invention, said somatostatin-dopamine chimeric compounds according to Formulas I, II and III are characterized in that:
R1 is —CH$_3$;
Y is —S—;
L is —(CH$_2$)—C(O)—, or —(CH$_2$)$_2$—; and
A$^1$ is Tyr, Lys, or absent.

According to another preferred embodiment of the present invention, said somatostatin-dopamine chimeric compounds according to Formulas I, II and III are characterized in that:
R1 is —CH$_3$;
Y is —S—;
L is —(CH$_2$)—C(O)—, or —(CH$_2$)$_2$—; and
A$^1$ is Tyr or Lys.

According to another preferred embodiment of the present invention, said somatostatin-dopamine chimeric compounds according to Formulas I, II and III are characterized in that:
R1 is —CH$_3$;
Y is —S—;
L is —(CH$_2$)—C(O)—, or —(CH$_2$)$_2$—; and
A$^1$ is Tyr or absent.

According to another preferred embodiment of the present invention, said somatostatin-dopamine chimeric compounds according to Formulas I, II and III are characterized in that:
R1 is —CH$_3$;
Y is —S—;
L is —(CH$_2$)—C(O)—, or —(CH$_2$)$_2$—; and
A$^1$ is Lys or absent.

According to another preferred embodiment of the present invention, said somatostatin-dopamine chimeric compounds according to Formulas I, II and III are characterized in that:
R1 is —CH$_3$;
Y is —S—;
L is —(CH$_2$)—C(O)—, or —(CH$_2$)$_2$—; and
A$^1$ is absent.

According to another preferred embodiment of the present invention, said somatostatin-dopamine chimeric compounds according to Formulas I, II and III are characterized in that:
R1 is —CH$_3$;
Y is —S—;
L is —(CH$_2$)$_2$—; and
A$^1$ is absent.

According to another preferred embodiment of the present invention, said somatostatin-dopamine chimeric compounds according to Formulas I, II and IIIa are characterized in that:
R1 is —CH$_3$;
Y is absent; and
L is —(CH$_2$)$_n$—.

According to another preferred embodiment of the present invention, said somatostatin-dopamine chimeric compounds according to Formulas I, II and IIIa are characterized in that:
R1 is —CH$_3$;
Y is absent; and
L is —(CH$_2$)$_2$—, —(CH$_2$)$_3$—, or —(CH$_2$)$_4$—; and
A$^1$ is Tyr, Lys, or absent.

According to another preferred embodiment of the present invention, said somatostatin-dopamine chimeric compounds according to Formulas I, II and IIIa are characterized in that:
R1 is —CH$_3$;
Y is absent; and
L is —(CH$_2$)$_2$—, —(CH$_2$)$_3$—, or —(CH$_2$)$_4$—; and
A$^1$ is Tyr or Lys.

According to another preferred embodiment of the present invention, said somatostatin-dopamine chimeric compounds according to Formulas I, II and IIIa are characterized in that:
R1 is —CH$_3$;
Y is absent; and
L is —(CH$_2$)$_2$—, —(CH$_2$)$_3$—, or —(CH$_2$)$_4$—; and
A$^1$ is Tyr or absent.

According to another preferred embodiment of the present invention, said somatostatin-dopamine chimeric compounds according to Formulas I, II and IIIa are characterized in that:
R1 is —CH$_3$;
Y is absent; and
L is —(CH$_2$)$_2$—, —(CH$_2$)$_3$—, or —(CH$_2$)$_4$—; and
A$^1$ is Lys or absent.

According to another preferred embodiment of the present invention, said somatostatin-dopamine chimeric compounds according to Formulas I, II and IIIa are characterized in that:
R1 is —CH$_3$;
Y is absent; and
L is —(CH$_2$)$_2$—, —(CH$_2$)$_3$—, or —(CH$_2$)$_4$—; and
A$^1$ is absent.

The above-mentioned preferred embodiments of the present invention are intended to be illustrative of the scope of the present invention, and they are in no way intended to limit the scope of the present invention to those which are specifically mentioned hereinabove. A skilled artisan would readily recognize that there are numerous other different combinations falling within the scope of Formulas I, II, III, and IIIa as defined herein. For instance, according to any one of the above-mentioned preferred embodiments of the present invention, A$^5$ may preferably be either Phe or 4Pal, and A$^9$ may preferably be Phe, 4FPhe, or Tyr.

Select compounds according to the present invention are provided in Table I.

TABLE I

| Compound No. | Chemical Name; Corresponding Structural Representations |
| --- | --- |
| 1 | (D-6-methyl-8β-ergolinyl)-propionyl-psi(CH₂NH)-cyclo(DLys-Arg-Phe-Phe-DTrp-Lys-Thr-4FPhe) (SEQ ID NO: 1); 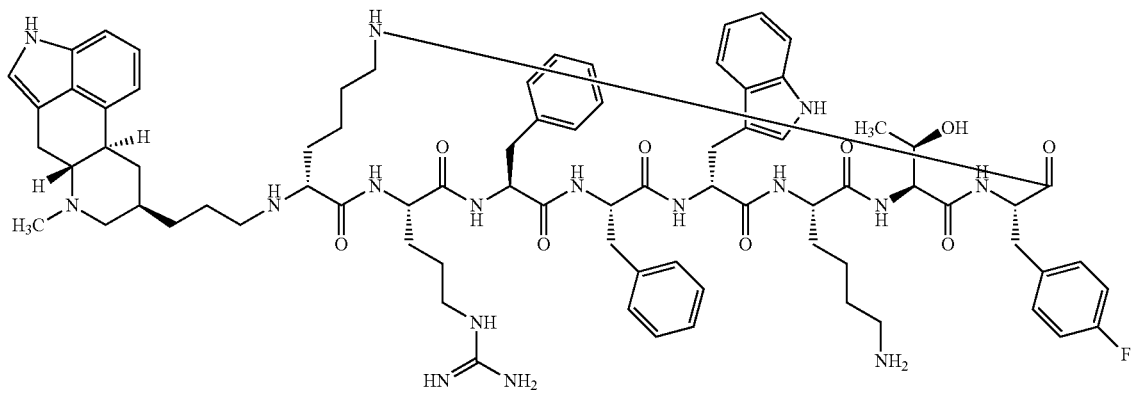 |
| 2 | (D-6-methyl-8β-ergolinyl)-butanoyl-psi(CH₂NH)-cyclo(DLys-Arg-Phe-Phe-DTrp-Lys-Thr-4FPhe) (SEQ ID NO: 2); 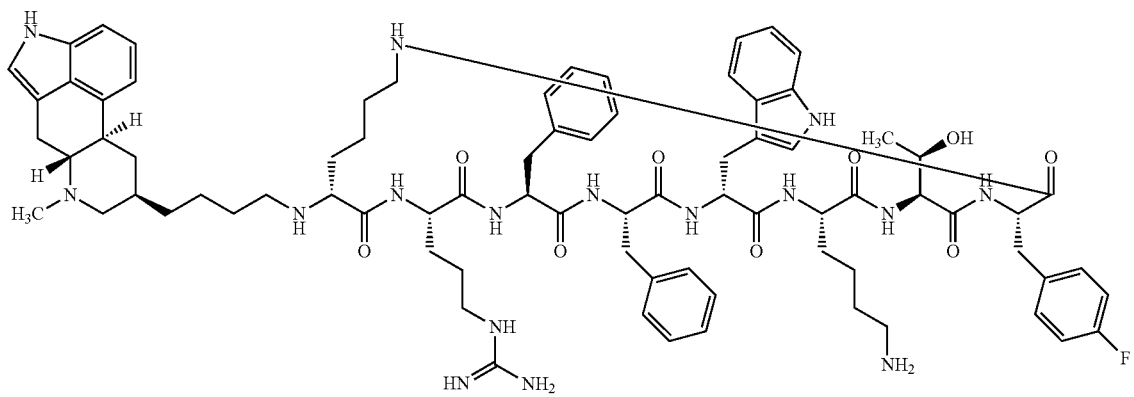 |
| 3 | (D-6-methyl-8β-ergolinyl)-pentanoyl-psi(CH₂NH)-cyclo(DLys-Arg-Phe-Phe-DTrp-Lys-Thr-4FPhe) (SEQ ID NO: 3); 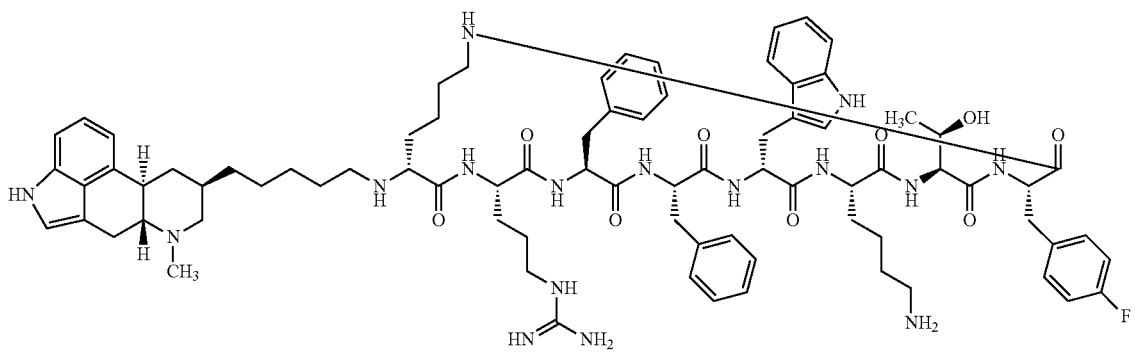 |

TABLE I-continued
| Compound No. | Chemical Name; Corresponding Structural Representations |
|---|---|
| 4 | Dop1-Tyr-psi(CH₂NH)-cyclo(DLys-Arg-Phe-4Pal-DTrp-Lys-Thr-Phe) (SEQ ID NO: 4); |
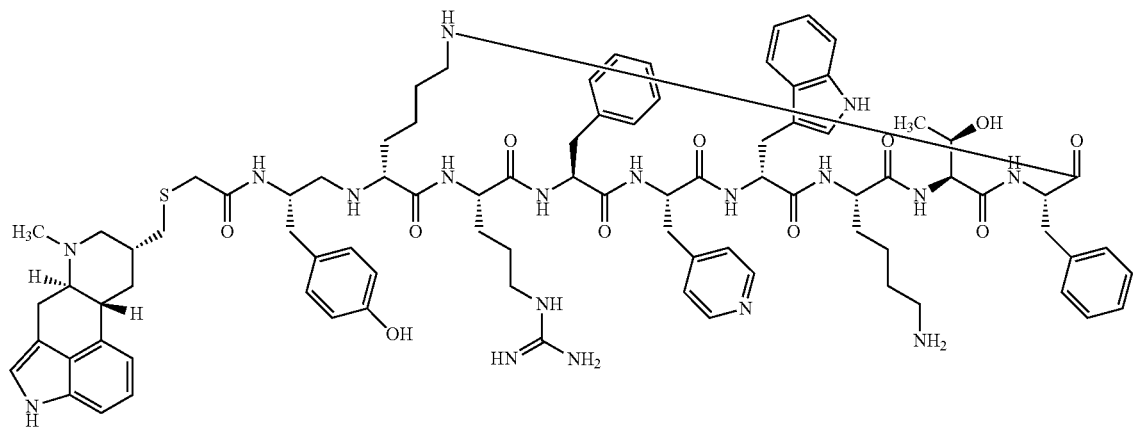
| 5 | Dop1-Tyr-psi(CH₂NH)-cyclo(DLys-Arg-Phe-Phe-DTrp-Lys-Thr-4FPhe) (SEQ ID NO: 5); |
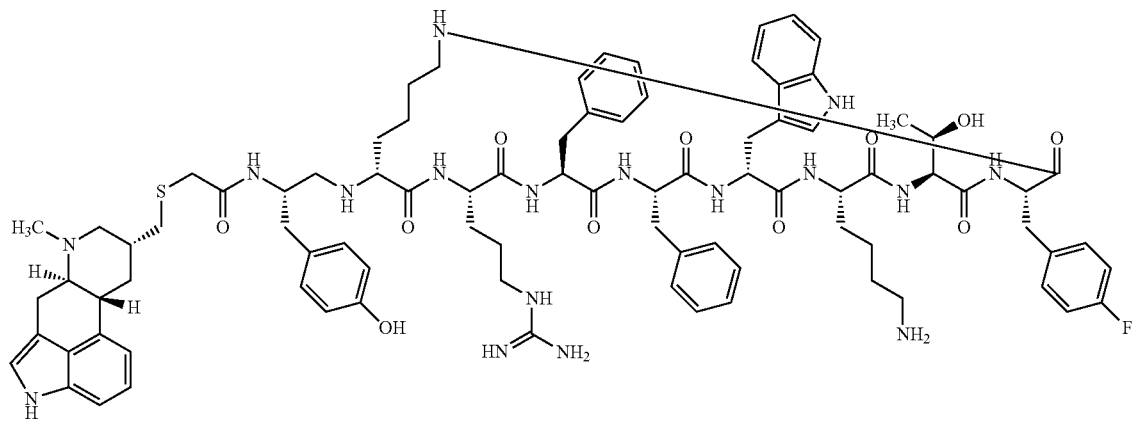
| 6 | Dop1-psi(CH₂NH)-cyclo(DLys-Arg-Phe-Phe-DTrp-Lys-Thr-4FPhe) (SEQ ID NO: 6); |
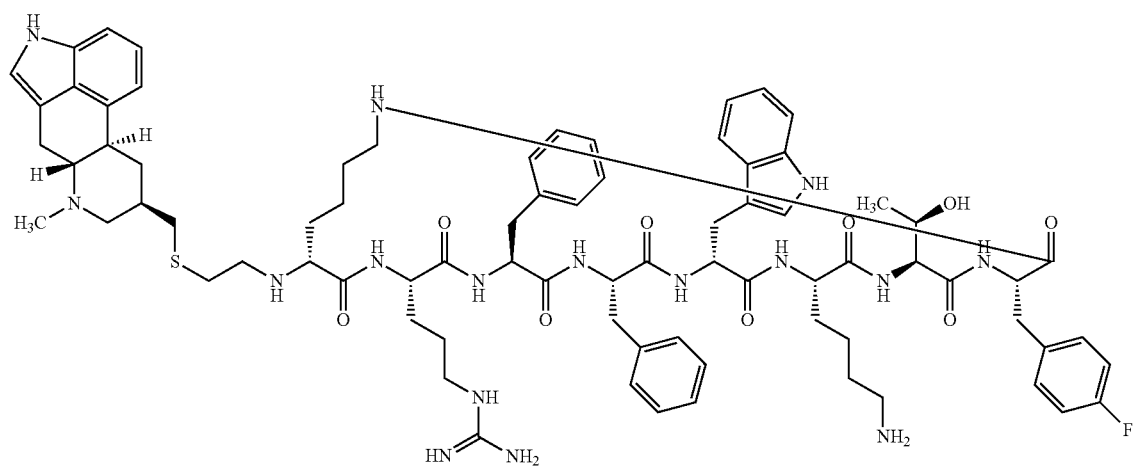

TABLE I-continued
| Compound No. | Chemical Name; Corresponding Structural Representations |
|---|---|
| 6A | Dop1-psi(CH$_2$NH)-cyclo(DLys-Arg-Phe-Phe-DTrp-Lys-Thr-3,4FPhe) (SEQ ID NO: 7); 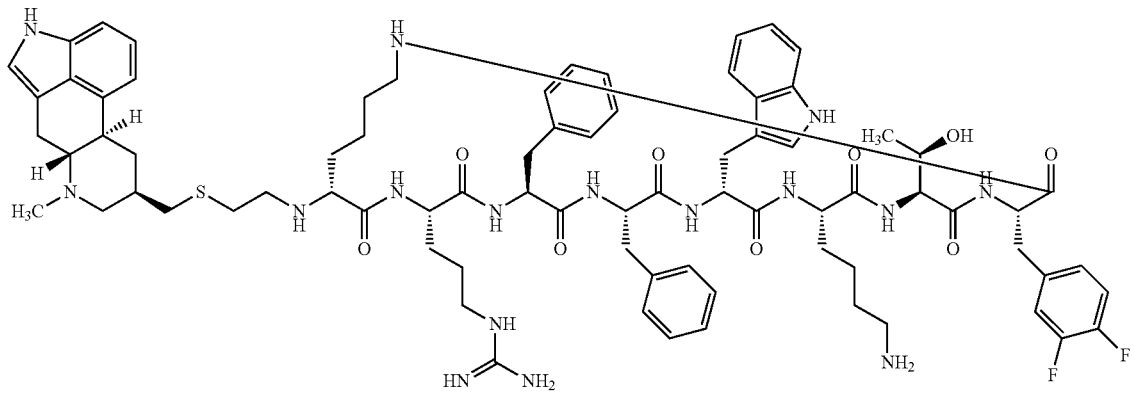 |
| 6B | Dop1-psi(CH$_2$NH)-cyclo(DLys-Arg-Phe-Phe-DTrp-Lys-Thr-3,5FPhe) (SEQ ID NO: 8); 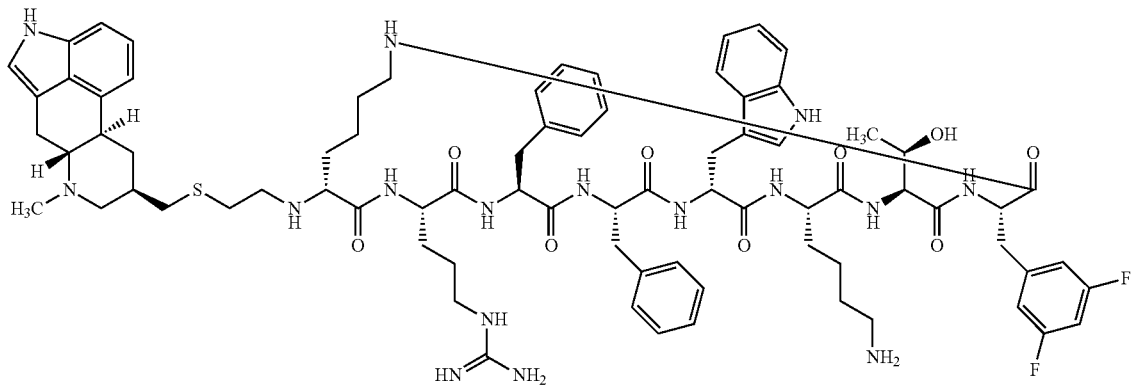 |
| 6C | Dop1-psi(CH$_2$NH)-cyclo(DLys-Arg-Phe-Phe-DTrp-Lys-Thr-3FPhe) (SEQ ID NO: 9); 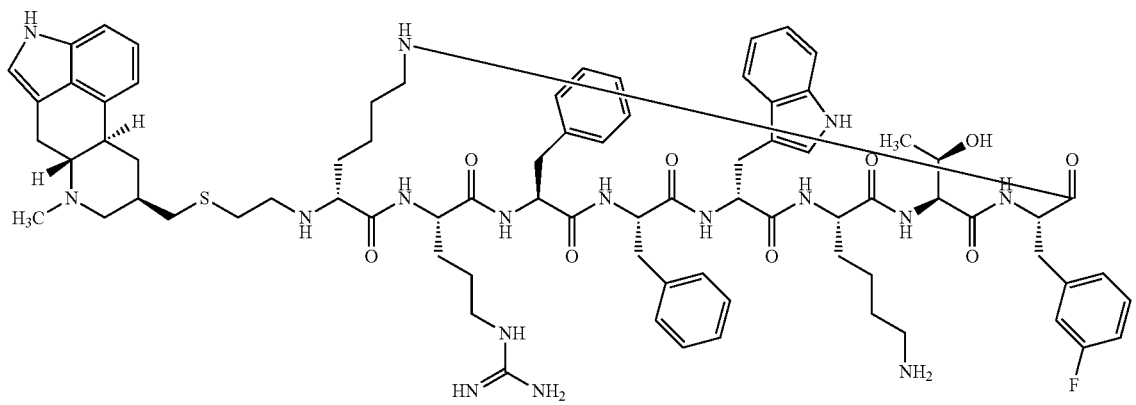 |

TABLE I-continued
| Compound No. | Chemical Name; Corresponding Structural Representations |
|---|---|
| 6D | Dop1-psi(CH₂NH)-cyclo(DLys-Arg-Phe-Phe-DTrp-Lys-Thr-2FPhe) (SEQ ID NO: 10); |
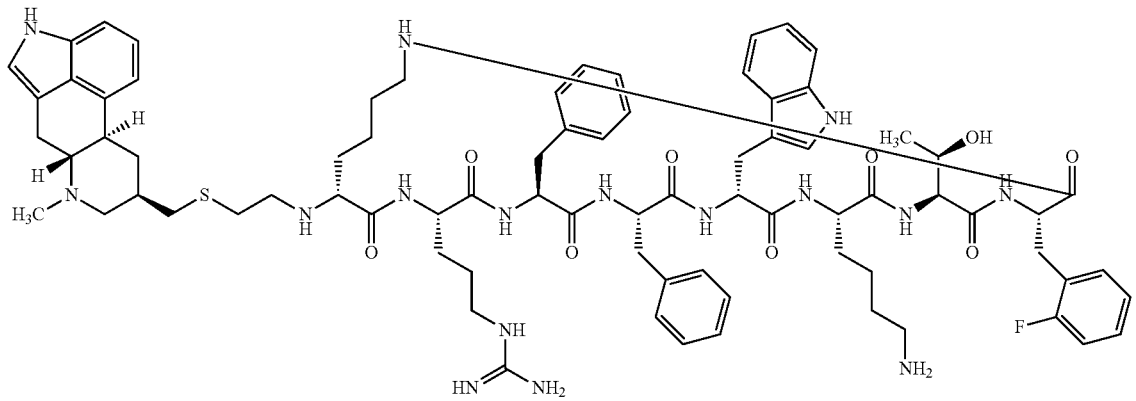
| 6E | Dop1-psi(CH₂NH)-cyclo(DLys-Arg-Phe-Phe-DTrp-Lys-Thr-2,3,4,5,6FPhe) (SEQ ID NO: 11); |
|---|---|
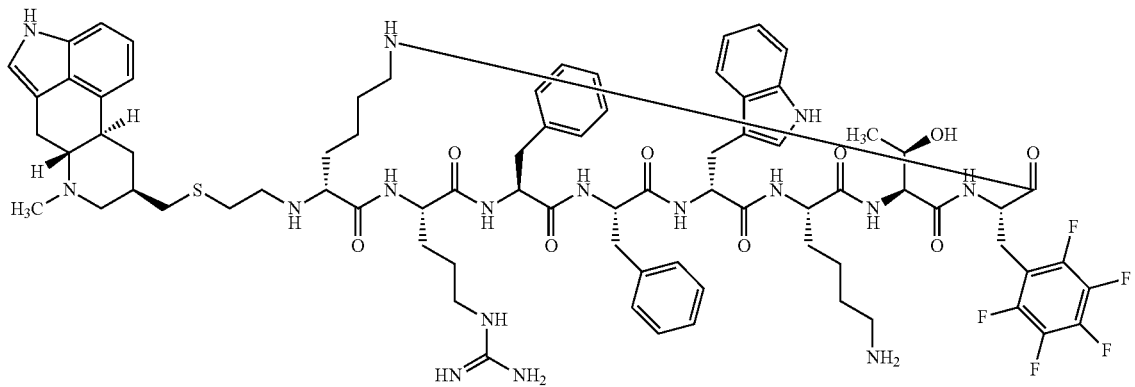
| 7 | Dop1-psi(CH₂NH)-cyclo(DLys-Arg-Phe-4Pal-DTrp-Lys-Thr-Tyr) (SEQ ID NO: 12); |
|---|---|
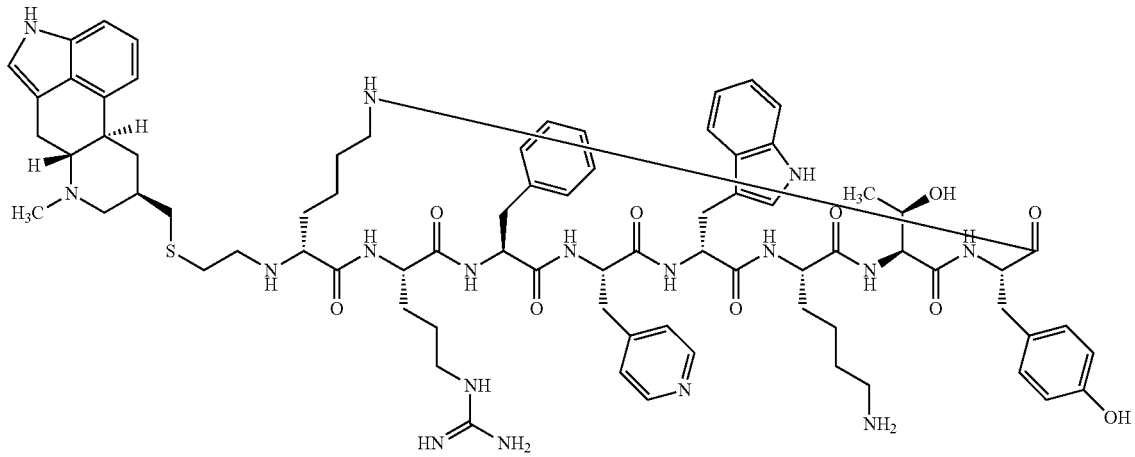

TABLE I-continued
| Compound No. | Chemical Name; Corresponding Structural Representations |
|---|---|
| 8 | Dop1-Lys(Dpo1)-psi(CH₂NH)-cyclo(DLys-Arg-Phe-4Pal-DTrp-Lys-Thr-Tyr) (SEQ ID NO: 13); |
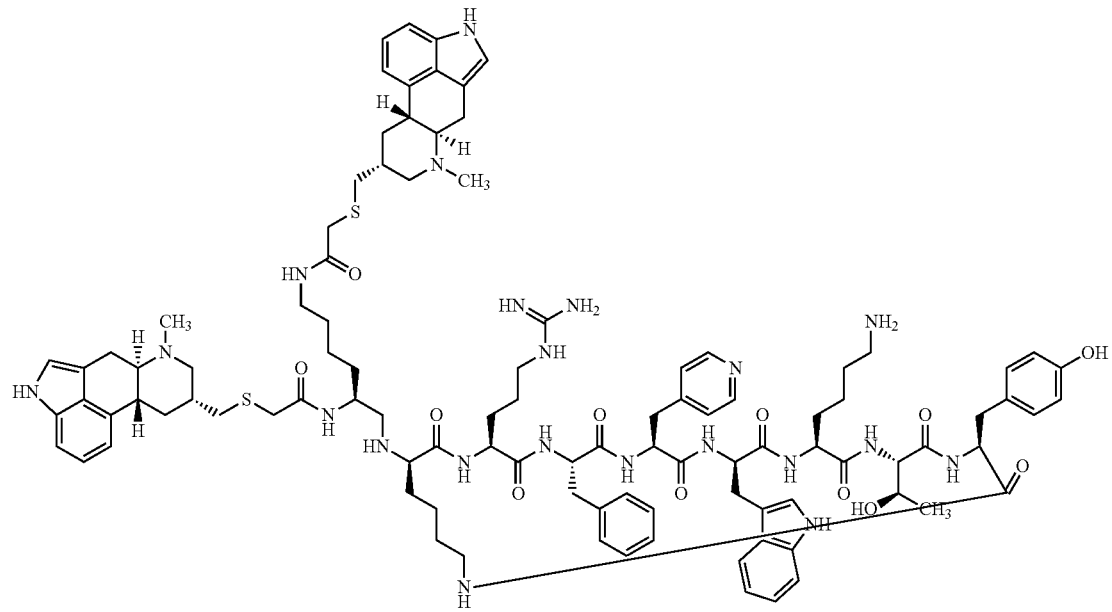
| 9 | Dop1-Lys(Dpo1)-psi(CH₂NH)-cyclo(DLys-Arg-Phe-4Pal-DTrp-Lys-Thr-Phe) (SEQ ID NO: 14); |
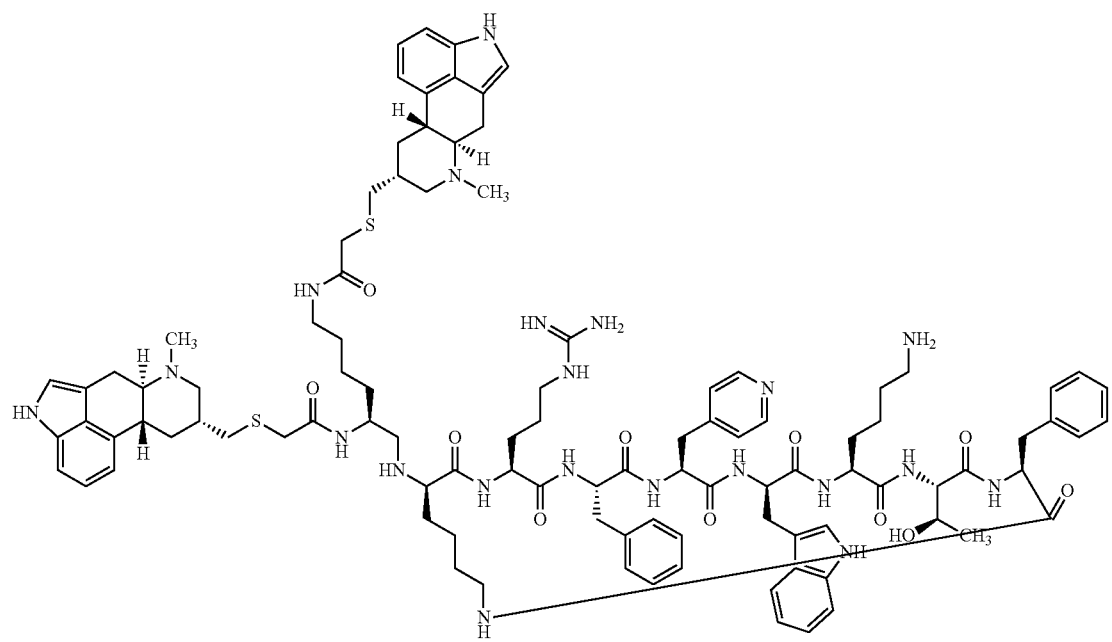

TABLE I-continued
| Compound No. | Chemical Name; Corresponding Structural Representations |
|---|---|
| 10 | Dop1(SO₂)-psi(CH₂NH)-cyclo(DLys-Arg-Phe-Phe-DTrp-Lys-Thr-4FPhe) (SEQ ID NO: 15); 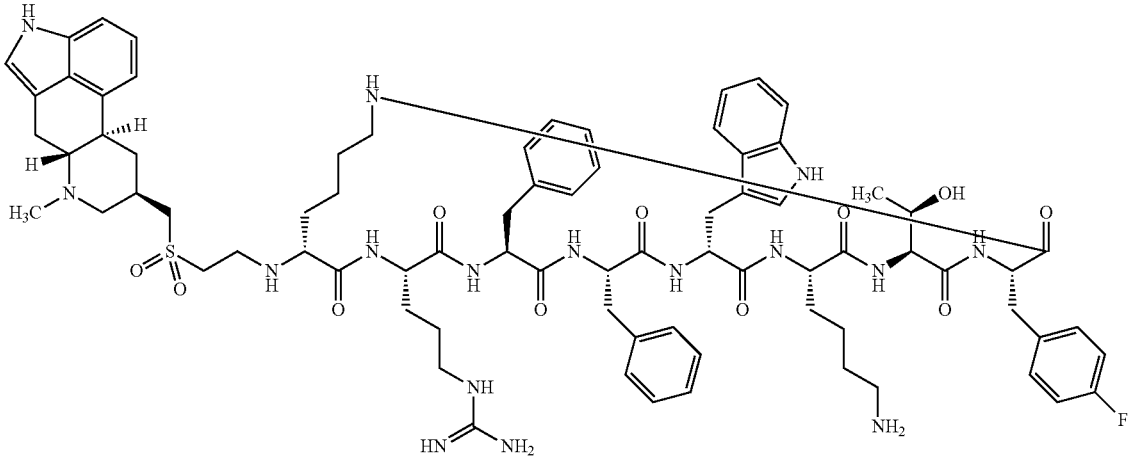 |
| 11 | Dop1[(R)SO]-psi(CH₂NH)-cyclo(DLys-Arg-Phe-4Pal-DTrp-Lys-Thr-Tyr) (SEQ ID NO: 16); 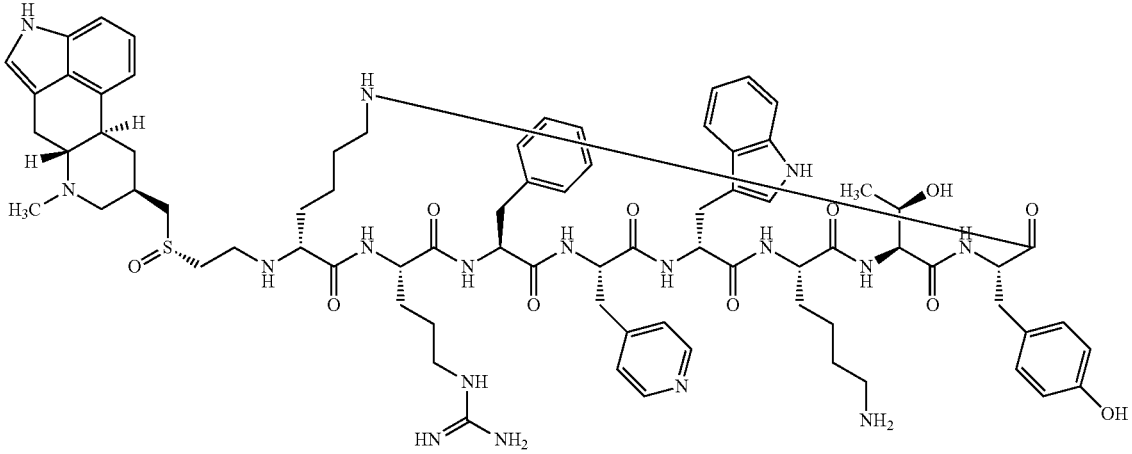 |
| 12 | Dop1[(S)SO]-psi(CH₂NH)-cyclo(DLys-Arg-Phe-4Pal-DTrp-Lys-Thr-Tyr) (SEQ ID NO: 17); 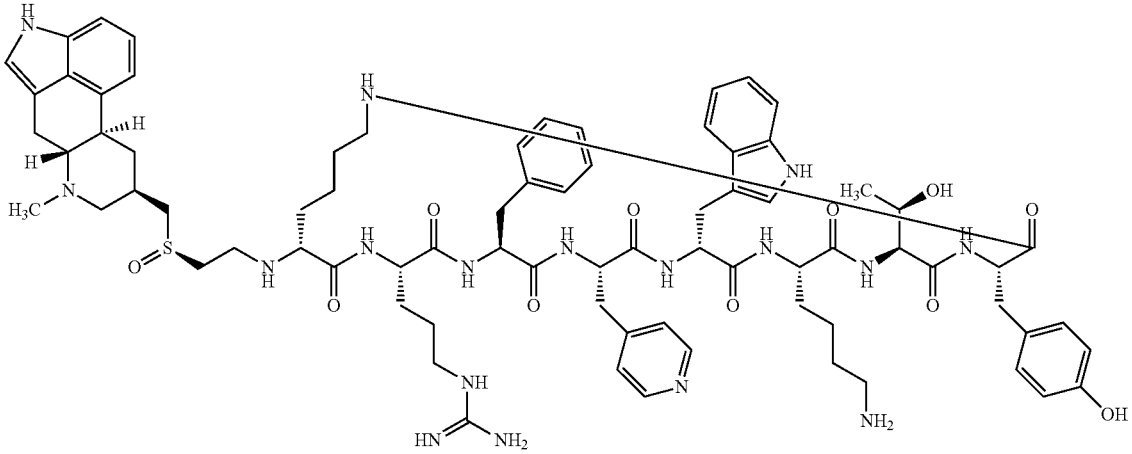 |

TABLE I-continued

| Compound No. | Chemical Name; Corresponding Structural Representations |
|---|---|
| 12A | Dop1(SO)-psi(CH₂NH)-cyclo(DLys-Arg-Phe-4Pal-DTrp-Lys-Thr-Tyr) (SEQ ID NO: 18); |
| 13 | Dop1(SO)-Tyr-psi(CH₂NH)-cyclo(DLys-Arg-Phe-Phe-DTrp-Lys-Thr-4FPhe) (SEQ ID NO: 19); |
| 14 | Dop1(SO)-psi(CH₂NH)-cyclo(DLys-Arg-Phe-Phe-DTrp-Lys-Thr-4FPhe) (SEQ ID NO: 20); |

TABLE I-continued
| Compound No. | Chemical Name; Corresponding Structural Representations |
|---|---|
| 15 | Dop1(SO)-Tyr-psi(CH2NH)-cyclo(DLys-Arg-Phe-4Pal-DTrp-Lys-Thr-Phe) (SEQ ID NO: 21); |
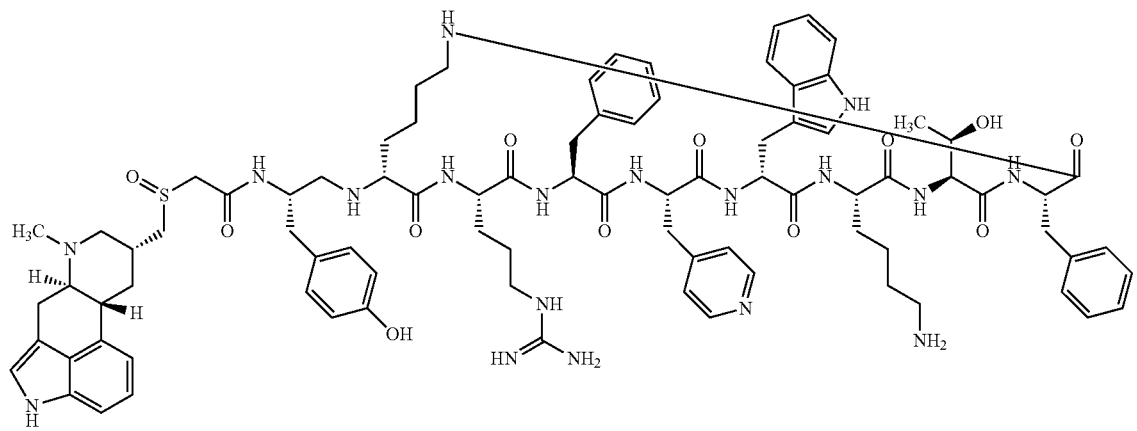
| 16 | Dop1(SO)-Lys[Dop1(SO)]-psi(CH2NH)-cyclo(DLys-Arg-Phe-4Pal-DTrp-Lys-Thr-Tyr) (SEQ ID NO: 22); |
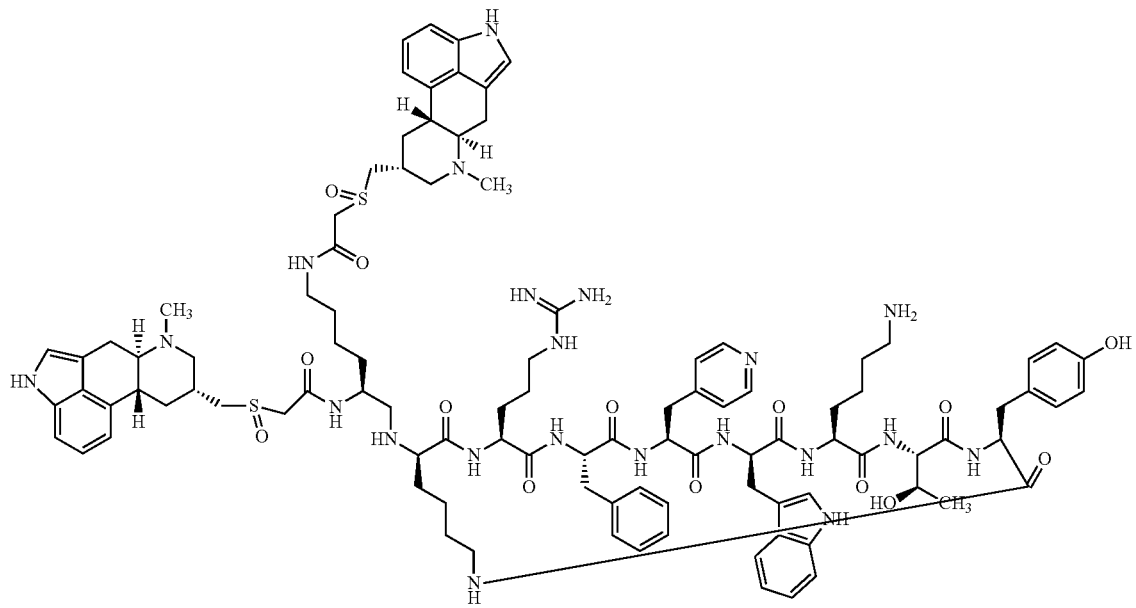

TABLE I-continued
| Compound No. | Chemical Name; Corresponding Structural Representations |
|---|---|
| 17 | Dop1(SO)-Lys[Dop1(SO)]-psi(CH₂NH)-cyclo(DLys-Arg-Phe-4Pal-DTrp-Lys-Thr-Phe) (SEQ ID NO: 23); |
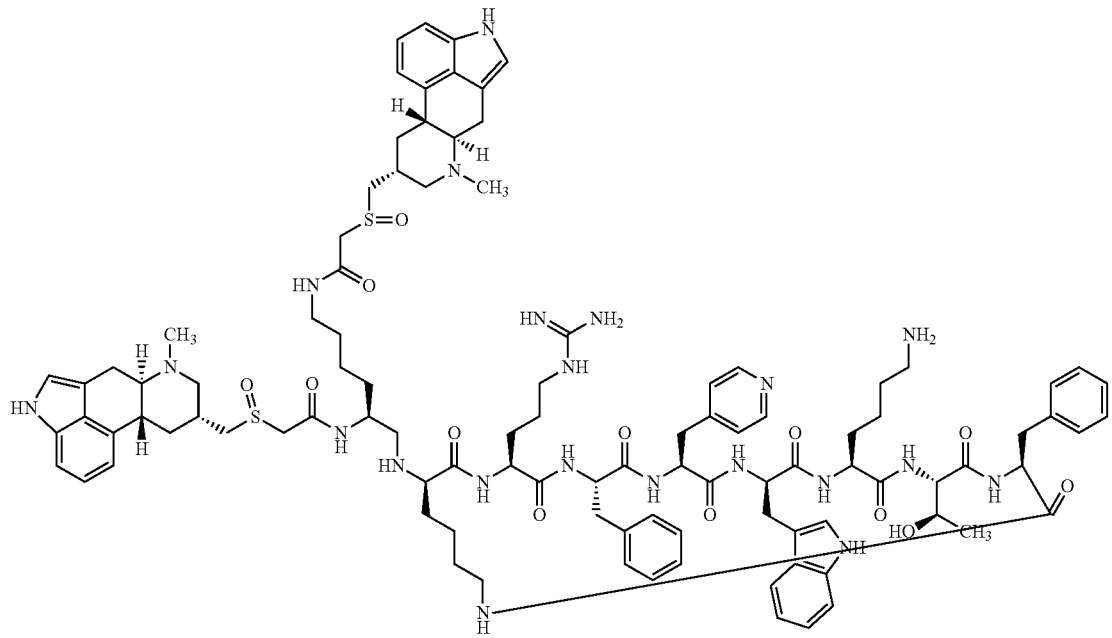
| 19 | Dop1(SO₂)-Tyr-psi(CH₂NH)-cyclo(DLys-Arg-Phe-Phe-DTrp-Lys-Thr-4FPhe) (SEQ ID NO: 24); |
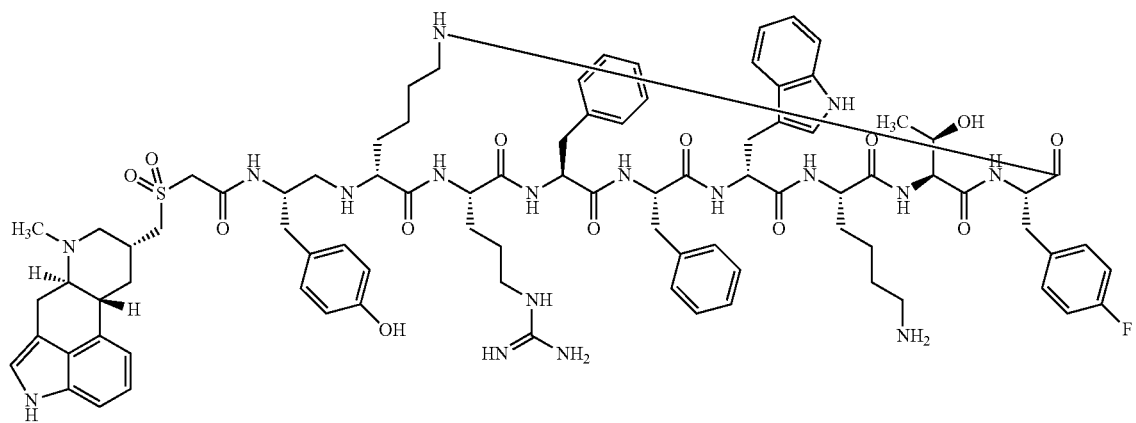

| Compound No. | Chemical Name; Corresponding Structural Representations |
|---|---|
| 20 | Dop1(SO₂)-psi(CH₂NH)-cyclo(DLys-Arg-Phe-4Pal-DTrp-Lys-Thr-Tyr) (SEQ ID NO: 25); |
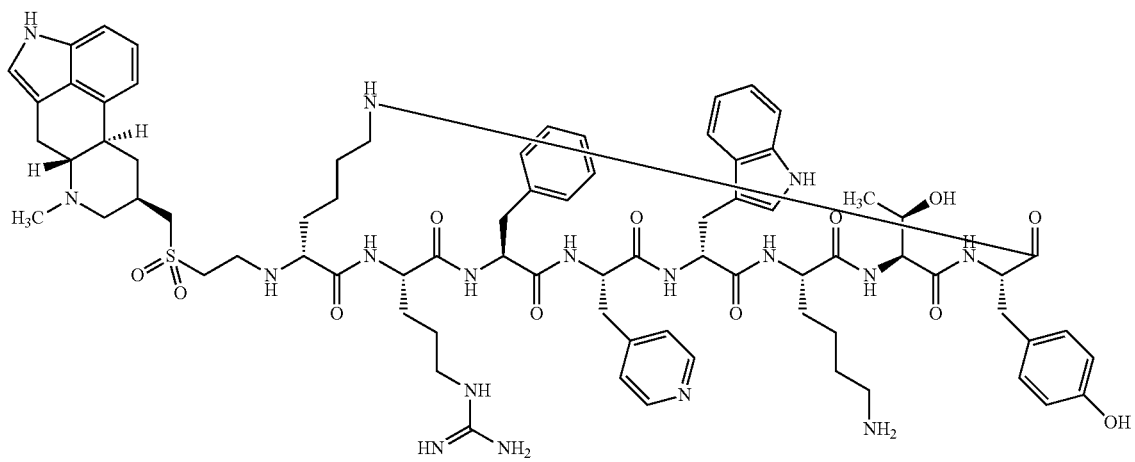
| | |
|---|---|
| 21 | Dop1(SO₂)-Tyr-psi(CH₂NH)-cyclo(DLys-Arg-Phe-4Pal-DTrp-Lys-Thr-Phe) (SEQ ID NO: 26); |
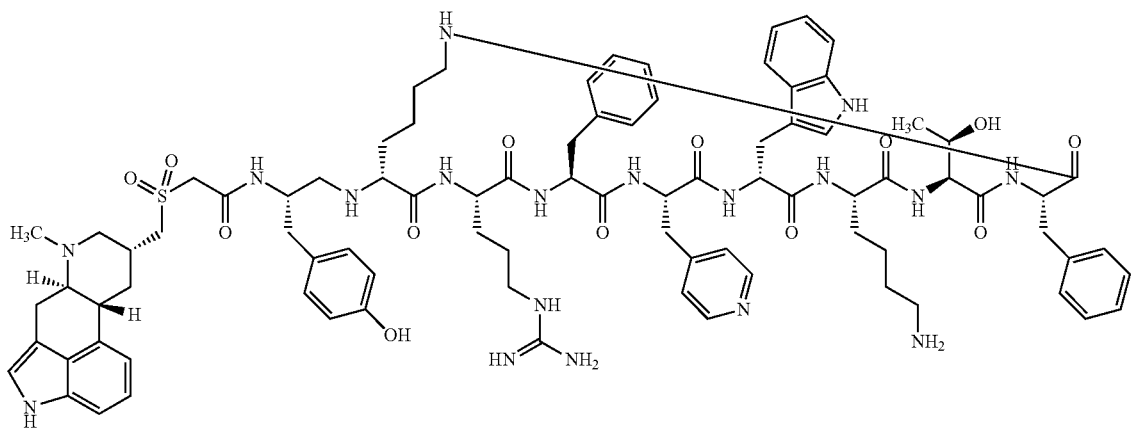
| | |
|---|---|
| 22 | 3-[N-(D-6-methyl-8β-ergolinylmethyl)]-aminopropionyl-psi(CH₂NAc)-cyclo(DLys-Arg-Phe-Phe-DTrp-Lys-Thr-4FPhe) (SEQ ID NO: 27); |
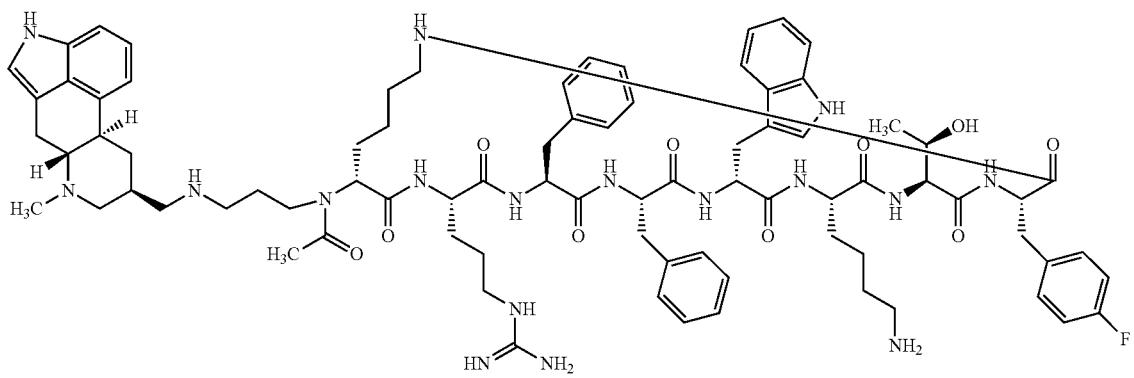

TABLE I-continued
| Compound No. | Chemical Name; Corresponding Structural Representations |
|---|---|
| 23 | Dop1-psi(CH₂NH)-cyclo(DLys-Arg-Phe-4Pal-DTrp-Lys-Thr-Phe) (SEQ ID NO: 28); 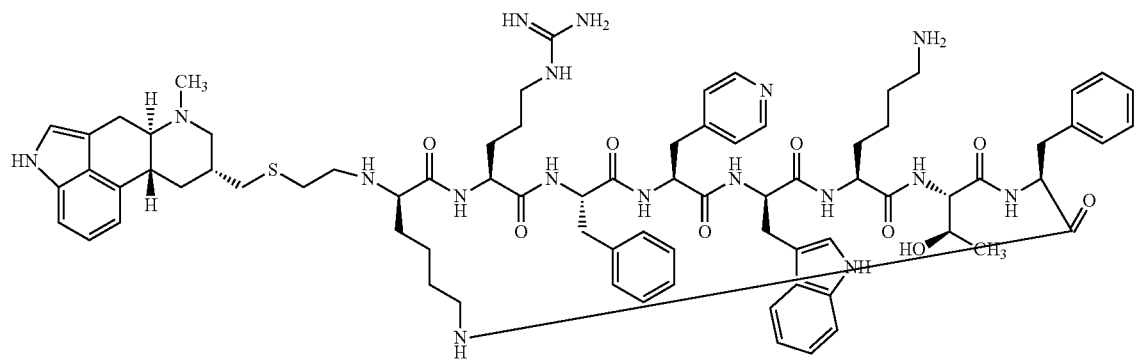 |
| 24 | Dop1-cyclo(DLys-Arg-Phe-4Pal-DTrp-Lys-Thr-Phe) (SEQ ID NO: 29); 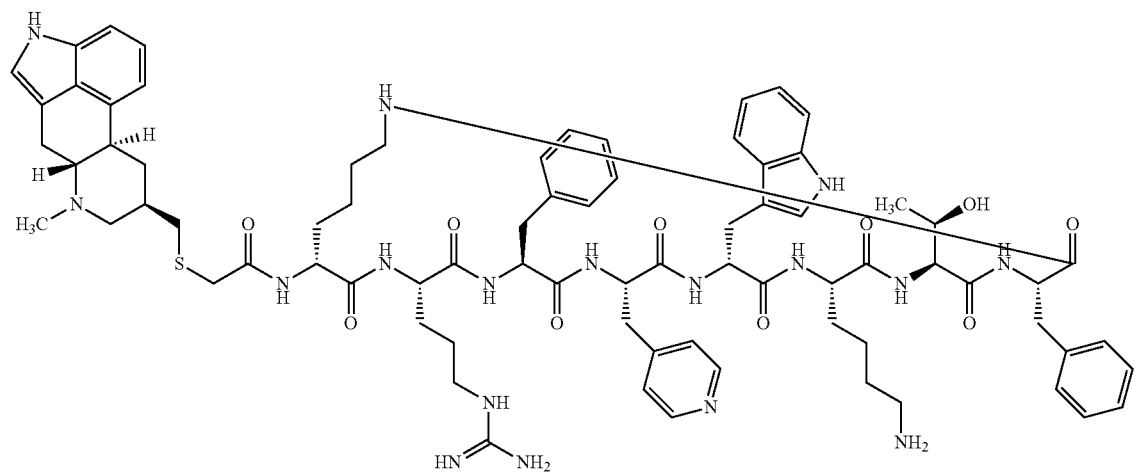 |
| 25 | Dop1-cyclo(DLys-Arg-Phe-4Pal-DTrp-Lys-Thr-Tyr) (SEQ ID NO: 30); 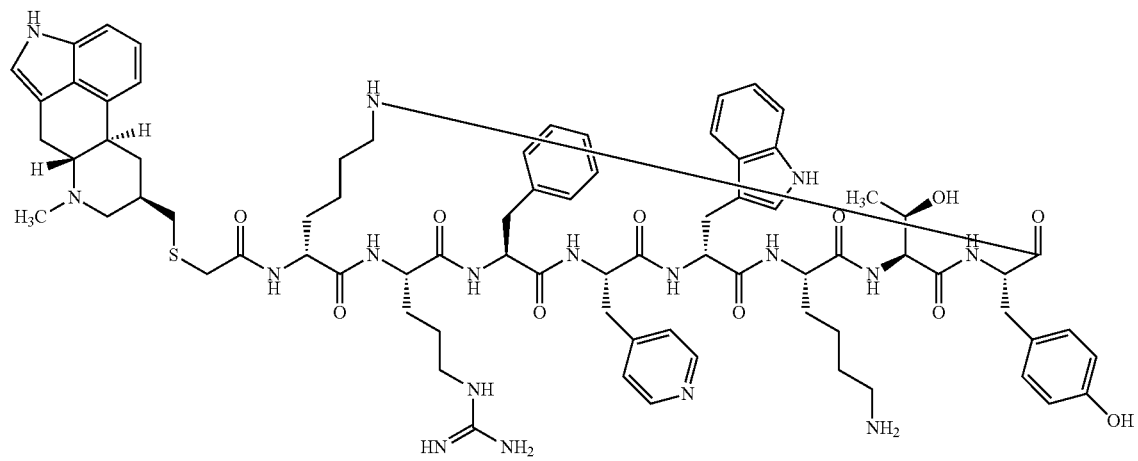 |

TABLE I-continued

| Compound No. | Chemical Name; Corresponding Structural Representations |
|---|---|
| 26 | Dop1-psi(CH₂NH)-cyclo(DLys-Arg-Phe-Phe-DTrp-Lys-Thr-Phe) (SEQ ID NO: 31); |
| 27 | 3-[N-acetyl-N-(D-6-methyl-8β-ergolinylmethyl)]-aminopropionyl-Tyr-psi(CH₂NH)-cyclo(DLys-Arg-Phe-Phe-DTrp-Lys-Thr-4FPhe) (SEQ ID NO: 32); |
| 28 | 3-[N-acetyl-N-(D-6-methyl-8β-ergolinylmethyl)]-aminopropionyl-psi(CH₂NAc)-cyclo(DLys-Arg-Phe-Phe-DTrp-Lys-Thr-4FPhe) (SEQ ID NO: 33); |

| Compound No. | Chemical Name; Corresponding Structural Representations |
|---|---|
| 28A | 3-[N-acetyl-N-(D-6-methyl-8β-ergolinylmethyl)]-aminopropionyl-psi(CH₂NH)-Tyr-psi(CH₂NH)-cyclo(DLys-Arg-Phe-Phe-DTrp-Lys-Thr-4FPhe) (SEQ ID NO: 34); |

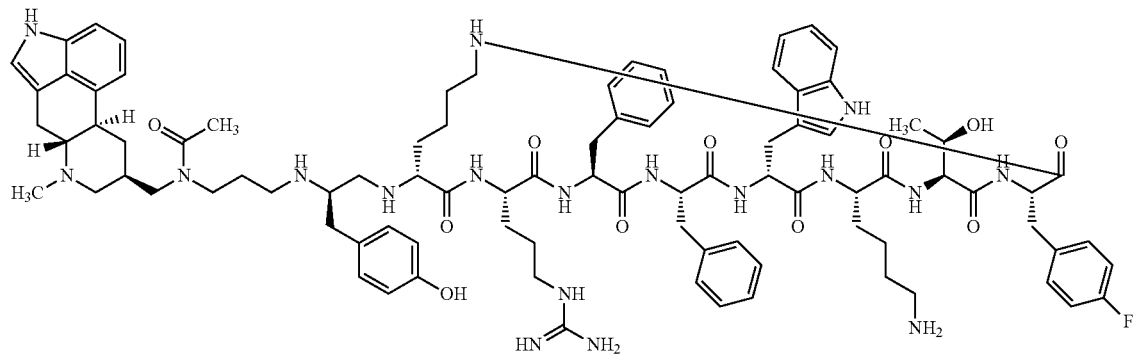

| | |
|---|---|
| 29 | bis[Dop1-psi(CH₂N)]-cyclo(DLys-Arg-Phe-4Pal-DTrp-Lys-Thr-Phe) (SEQ ID NO: 35); |

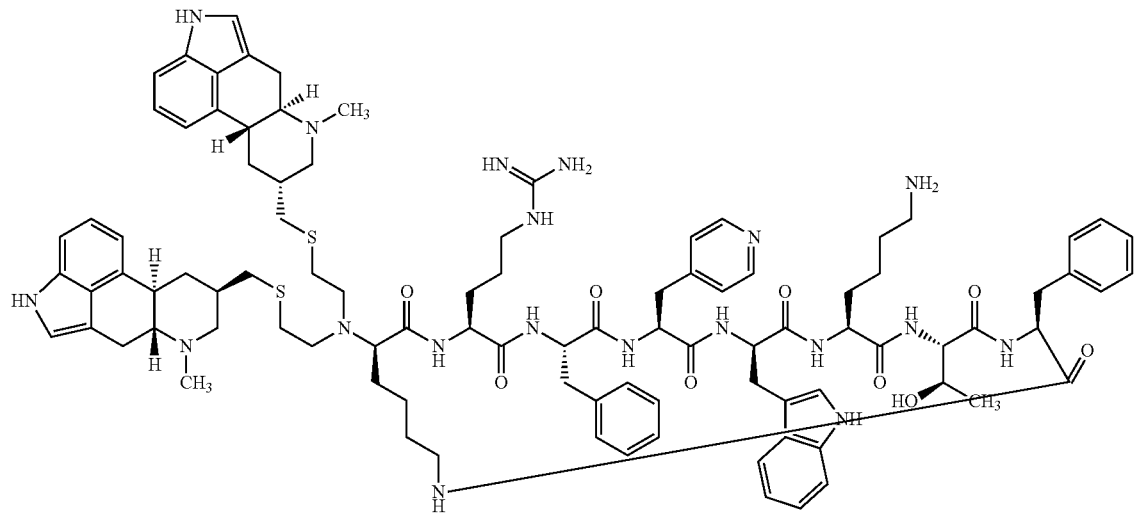

| | |
|---|---|
| 29A | 3-[N-acetyl-(D-6-methyl-8β-ergolinylmethyl)]-aminopropionyl-psi(CH₂NH)-cyclo(DLys-Arg-Phe-Phe-DTrp-Lys-Thr-4FPhe) (SEQ ID NO: 36); |

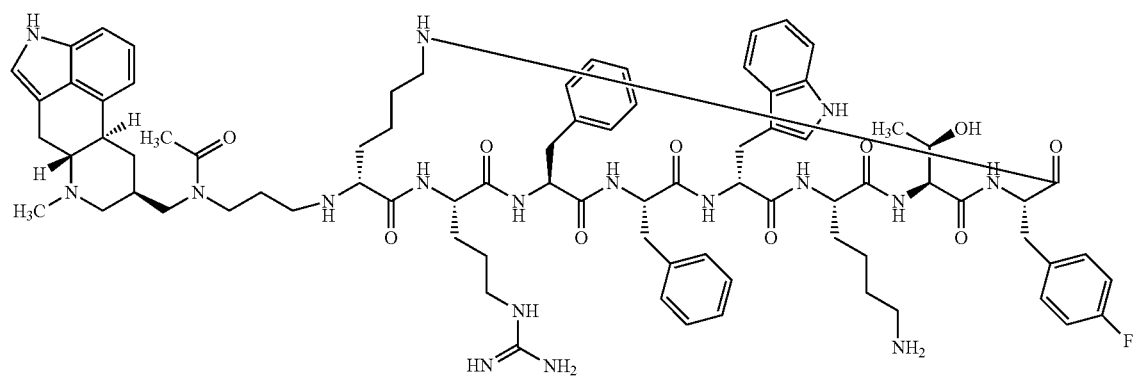

TABLE I-continued
| Compound No. | Chemical Name; Corresponding Structural Representations |
|---|---|
| 30 | Dop1-Tyr-psi(CH₂NH)-cyclo(DOrn-Arg-Phe-Phe-DTrp-Lys-Thr-Phe) (SEQ ID NO: 37); |
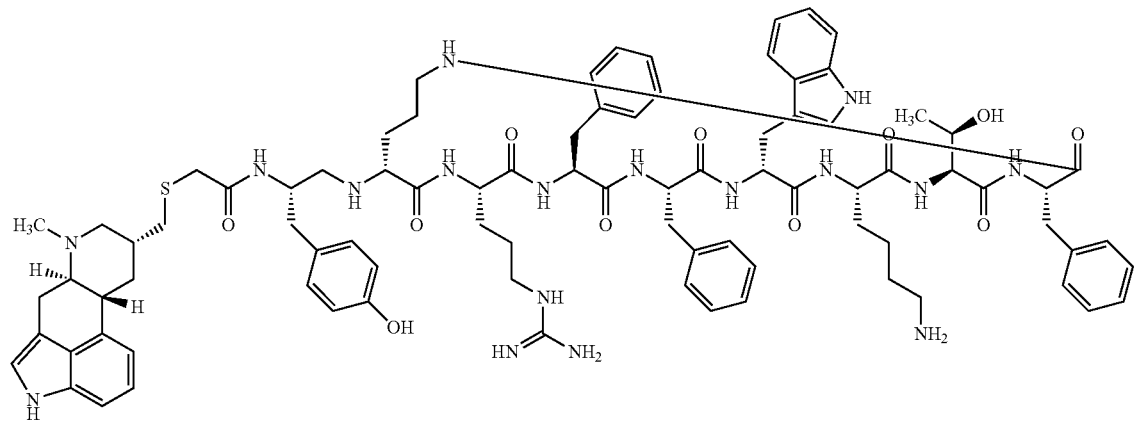
| 31 | Dop1-Tyr-psi(CH₂NH)-cyclo(Lys-Arg-Phe-Phe-DTrp-Lys-Thr-Phe) (SEQ ID NO: 38); |
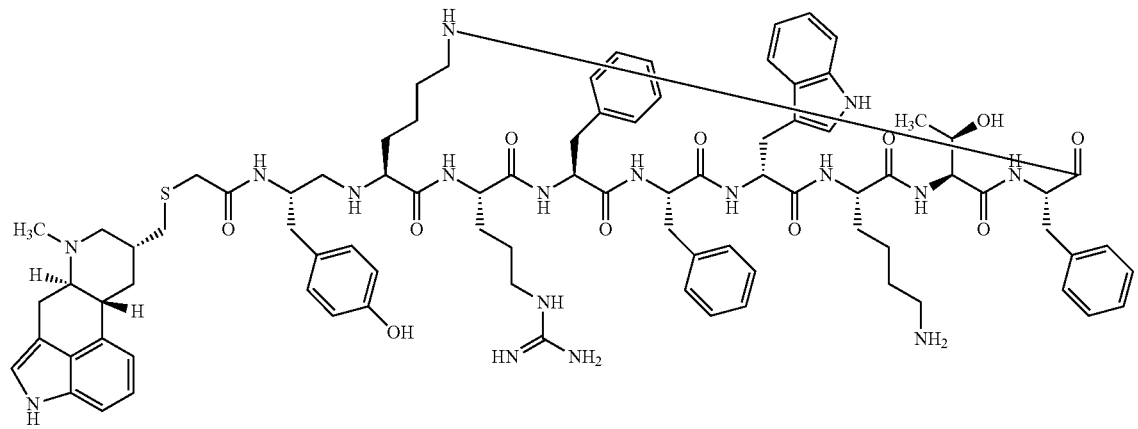
| 32 | Dop1-Tyr-psi(CH₂NH)-cyclo(DLys-Arg-Phe-Phe-DTrp-Lys-Thr-Phe) (SEQ ID NO: 39); |
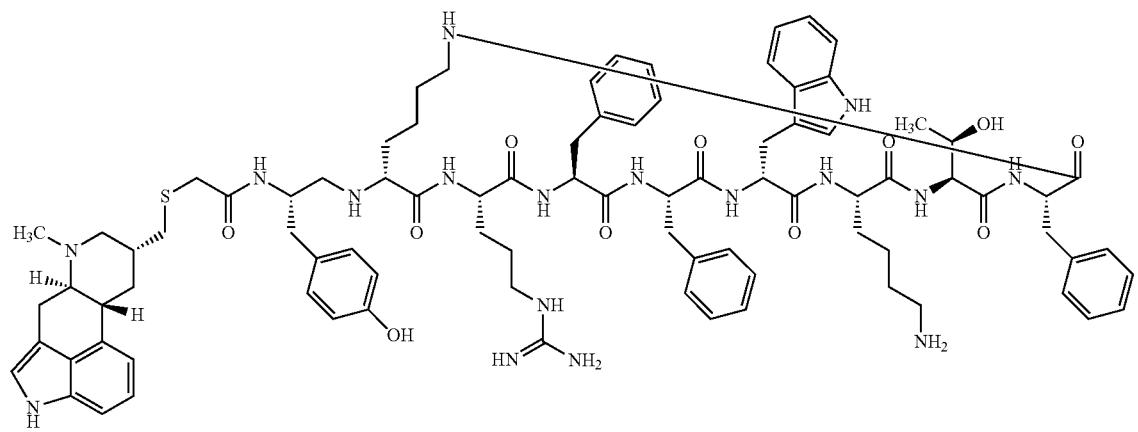

TABLE I-continued

| Compound No. | Chemical Name; Corresponding Structural Representations |
|---|---|
| 33 | Dop1-Tyr-psi(CH₂NH)-cyclo(DLys-Arg-Phe-Phe-DTrp-Lys-Thr-Tyr) (SEQ ID NO: 40); |
| 34 | Dop1-cyclo(DLys-Arg-Phe-Phe-DTrp-Lys-Thr-4FPhe) (SEQ ID NO: 41); |
| 35 | bis[Dop1-psi(CH₂N)]-cyclo(DLys-Arg-Phe-4Pal-DTrp-Lys-Thr-Tyr) (SEQ ID NO: 42); |

| Compound No. | Chemical Name; Corresponding Structural Representations |
|---|---|
| 37 | Dop1-DTyr-cyclo(DLys-Arg-Phe-Phe-DTrp-Lys-Thr-Phe) (SEQ ID NO: 43); |
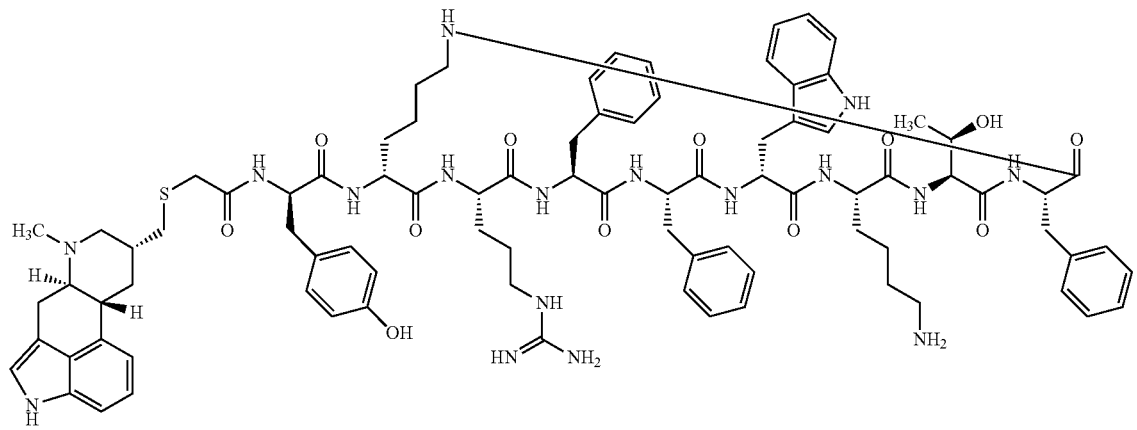
| | |
|---|---|
| 38 | Dop1-Tyr-psi(CH$_2$NH)-cyclo(DLys-Arg-Phe-3Pal-DTrp-Lys-Thr-Phe) (SEQ ID NO: 44); |
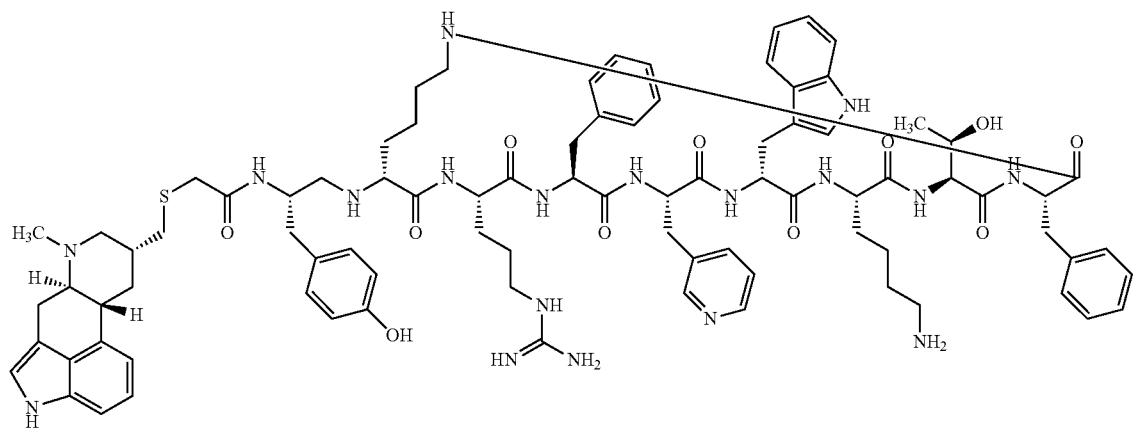
| | |
|---|---|
| 39 | bis[Dop1-psi(CH$_2$N)]-cyclo(DLys-Arg-Phe-Phe-DTrp-Lys-Thr-4FPhe) (SEQ ID NO: 45); |
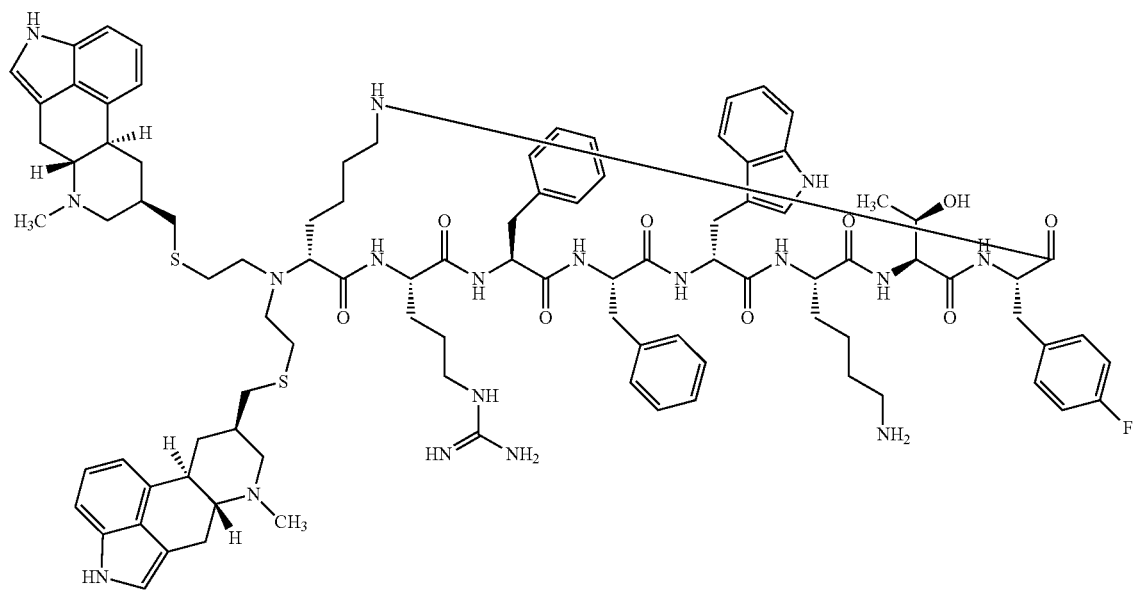

TABLE I-continued
| Compound No. | Chemical Name; Corresponding Structural Representations |
|---|---|
| 40 | bis[Dop1-psi(CH₂N)]-cyclo(DLys-Arg-Phe-Phe-DTrp-Lys-Thr-Phe) (SEQ ID NO: 46); 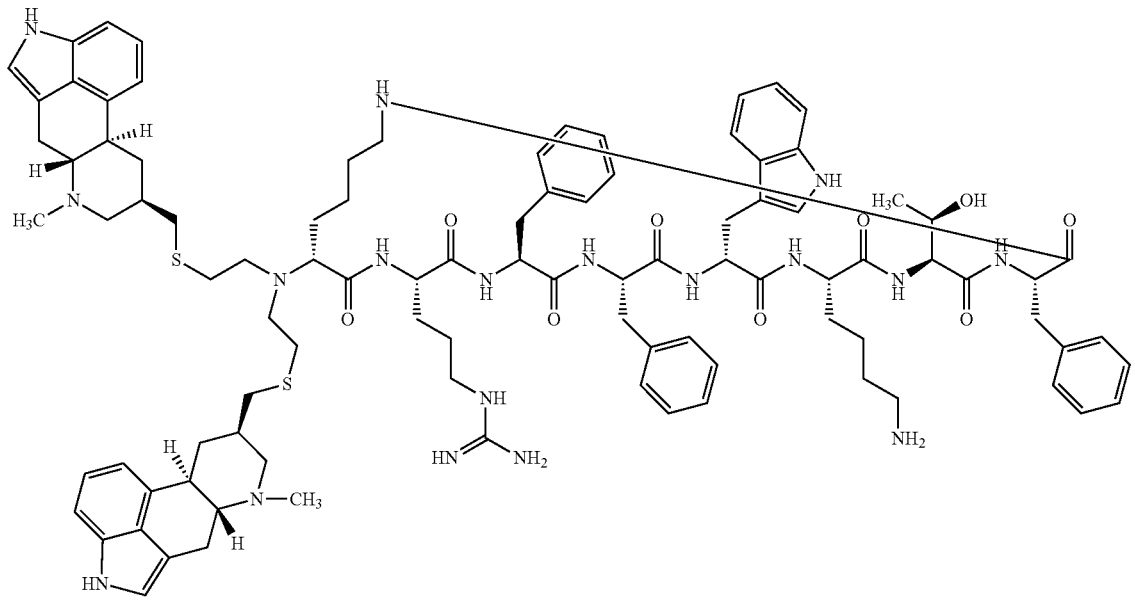 |
| 41 | Dop1-DTyr-psi(CH₂NH)-cyclo(DLys-Arg-Phe-Phe-DTrp-Lys-Thr-Phe) (SEQ ID NO: 47); 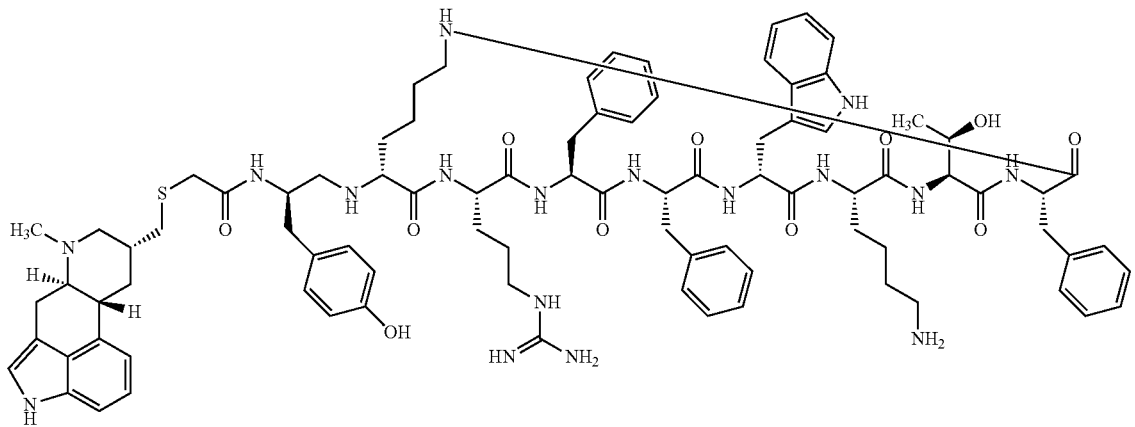 |

TABLE I-continued
| Compound No. | Chemical Name; Corresponding Structural Representations |
|---|---|
| 42 | [N-(D-6-methyl-8β-ergolinylmethyl)]-N-(methylsulfonyl)]-aminopropionyl-Tyr-psi(CH₂NH)-cyclo(DLys-Arg-Phe-Phe-DTrp-Lys-Thr-4FPhe) (SEQ ID NO: 48); |
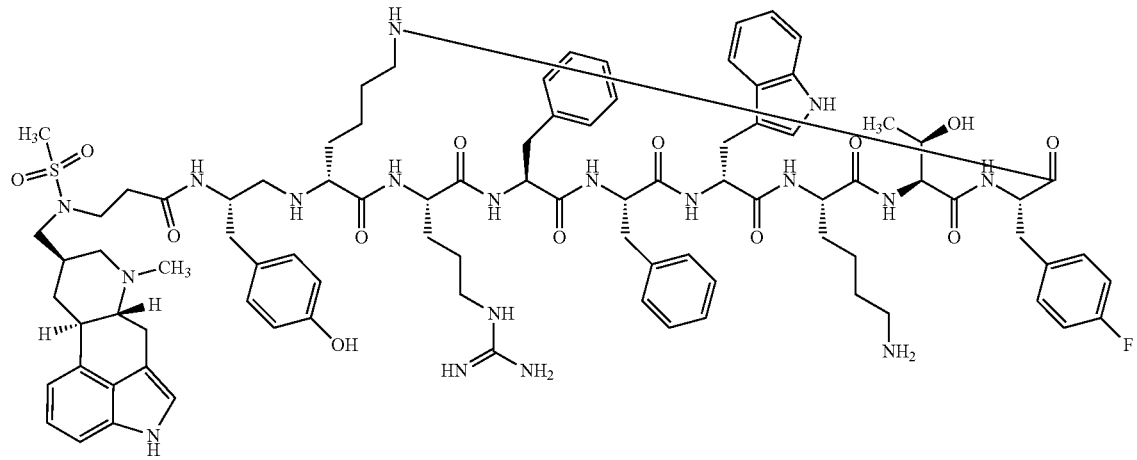
| | |
|---|---|
| 43 | Dop1-Tyr-psi(CH₂NH)-cyclo(Orn-Arg-Phe-Phe-DTrp-Lys-Thr-Phe) (SEQ ID NO: 49); |
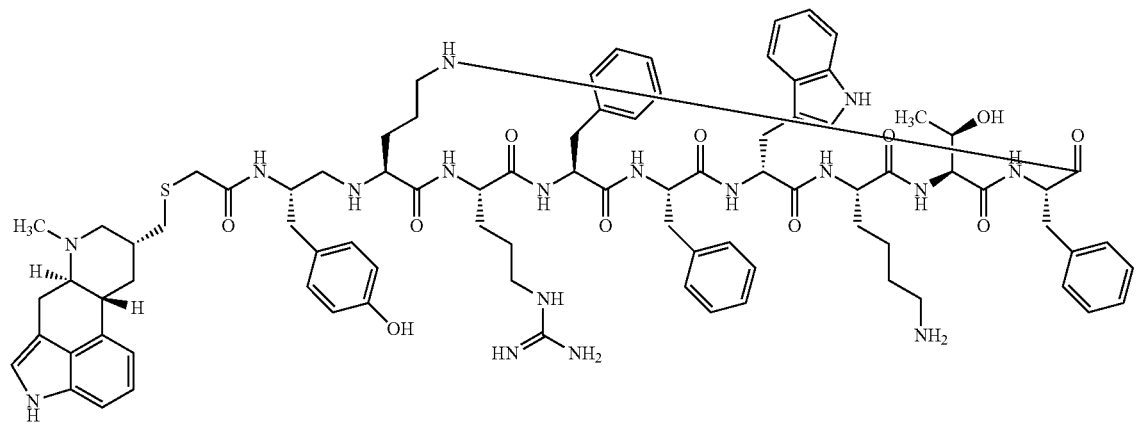
| | |
|---|---|
| 44 | Dop1-cyclo(DLys-Arg-Phe-Phe-DTrp-Lys-Thr-Phe) (SEQ ID NO: 50); |
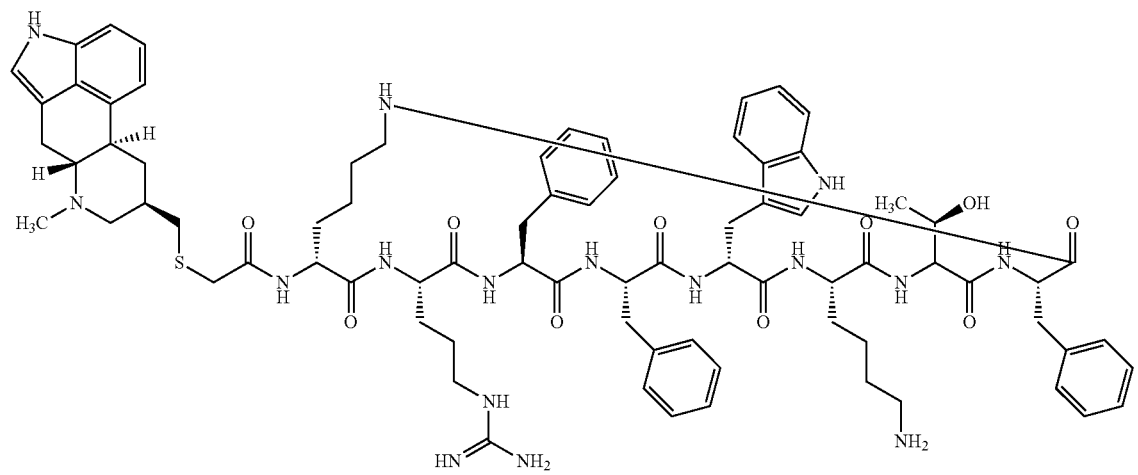

TABLE I-continued
| Compound No. | Chemical Name; Corresponding Structural Representations |
|---|---|
| 46 | Dop1-DTyr-psi(CH$_2$NH)-cyclo(DLys-Arg-4Pal-Tyr-DTrp-Lys-Thr-Phe) (SEQ ID NO: 51); |
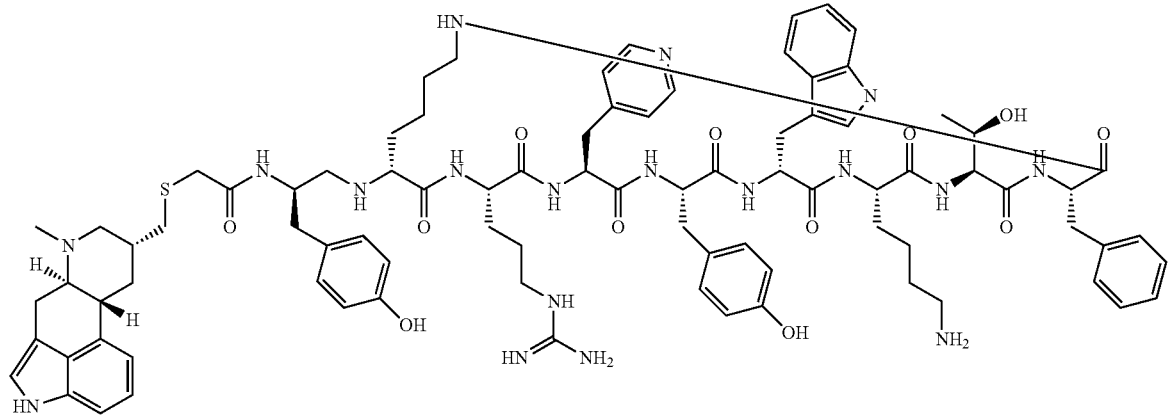
| 47 | Dop1-Lys(Dpo1)-psi(CH$_2$NH)-cyclo(DLys-Arg-Phe-Phe-DTrp-Lys-Thr-4FPhe) (SEQ ID NO: 52); |
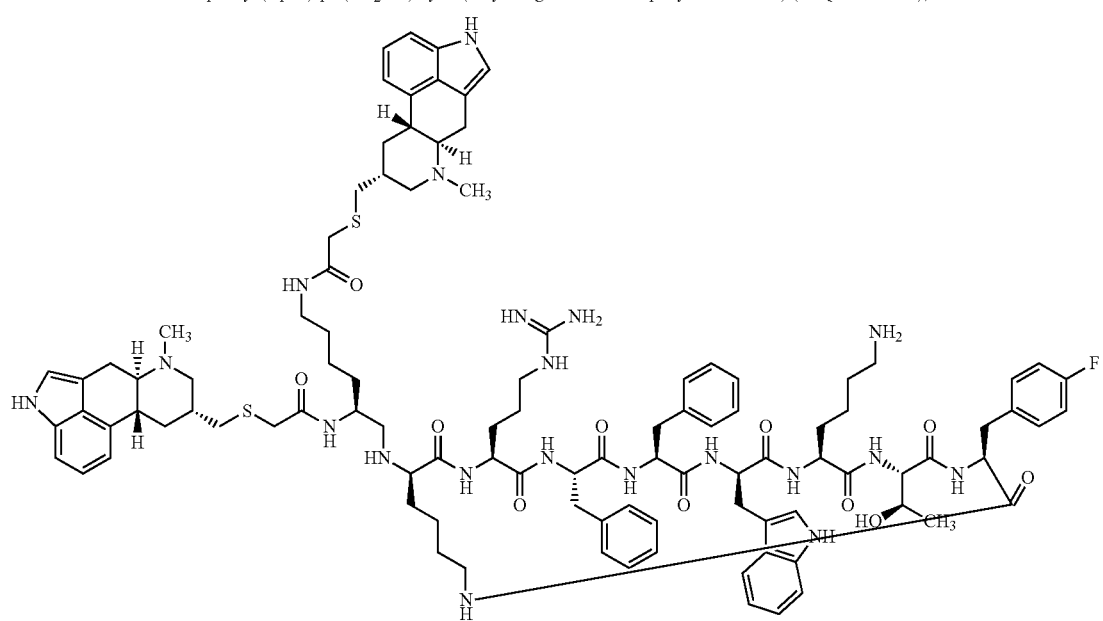

TABLE I-continued

| Compound No. | Chemical Name; Corresponding Structural Representations |
|---|---|
| 48 | (D-6-methyl-8β-ergolinylmethyl)-sulfonylpropyl-cyclo(DLys-Arg-Phe-Phe-DTrp-Lys-Thr-4FPhe) (SEQ ID NO: 53); |

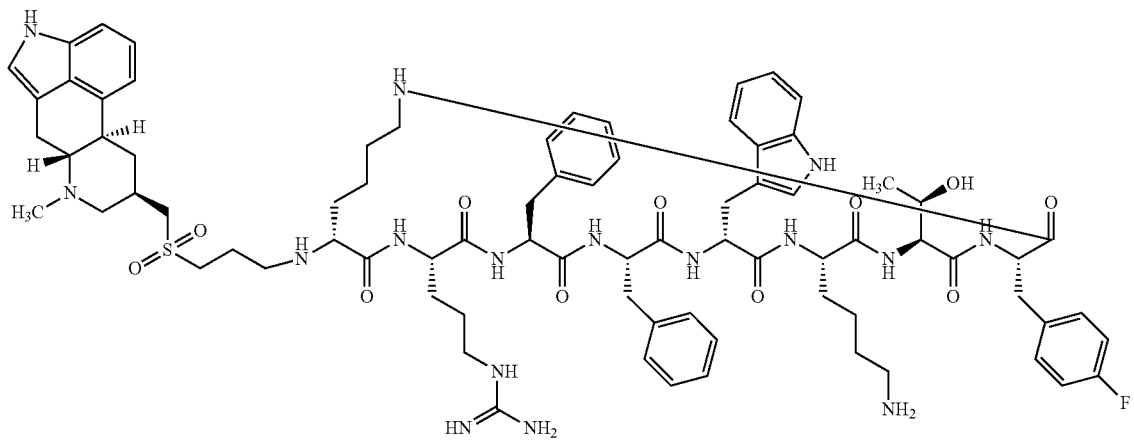

In another embodiment of the present invention, the somatostatin-dopamine chimeric analog comprises any of the compounds listed in Table I.

In a preferred embodiment of the present invention, the somatostatin-dopamine chimeric analog comprises a compound selected from the following list:

```
                                     (SEQ ID NO: 4)
Dop1-Tyr-psi(CH2NH)-cyclo(DLys-Arg-Phe-4Pal-DTrp- Lys-Thr-Phe);

(SEQ ID NO: 5)
Dop1-Tyr-psi(CH2NH)-cyclo(DLys-Arg-Phe-Phe-DTrp-

Lys-Thr-4FPhe);

(SEQ ID NO: 6)
Dop1-psi(CH2NH)-cyclo(DLys-Arg-Phe-Phe-DTrp-Lys-

Thr-4FPhe);

(SEQ ID NO: 12)
Dop1-psi(CH2NH)-cyclo(DLys-Arg-Phe-4Pal-DTrp-Lys-

Thr-Tyr);

(SEQ ID NO: 13)
Dop1-Lys(Dop1)-psi(CH2NH)-cyclo(DLys-Arg-Phe-4Pal-

DTrp-Lys-Thr-Tyr);

(SEQ ID NO: 14)
Dop1-Lys(Dop1)-psi(CH2NH)-cyclo(DLys-Arg-Phe-4Pal-

DTrp-Lys-Thr-Phe);

(SEQ ID NO: 28)
Dop1-psi(CH2NH)-cyclo(DLys-Arg-Phe-4Pal-DTrp-Lys-

Thr-Phe);

(SEQ ID NO: 29)
Dop1-cyclo(DLys-Arg-Phe-4Pal-DTrp-Lys-Thr-Phe);

(SEQ ID NO: 30)
Dop1-cyclo(DLys-Arg-Phe-4Pal-DTrp-Lys-Thr-Tyr);
```

```
-continued
                                    (SEQ ID NO: 35)
bis[Dop1-psi(CH2N)]cyclo(DLys-Arg-Phe-4Pal-DTrp- Lys-Thr-Phe);

(SEQ ID NO: 39)
Dop1-Tyr-psi(CH2NH)-cyclo(DLys-Arg-Phe-Phe-DTrp-

Lys-Thr-Phe);

(SEQ ID NO: 40)
Dop1-Tyr-psi(CH2NH)-cyclo(DLys-Arg-The-Phe-DTrp-

Lys-Thr-Tyr);
and (SEQ ID NO: 18)
Dop1(SO)-ps1(CH2NH)-cyclo(DLys-Arg-Phe-4Pal-DTrp- Lys-Thr-Tyr).
```

In another preferred embodiment of the present invention, the somatostatin-dopamine chimeric analog comprises a compound selected from the following list:

```
                                     (SEQ ID NO: 6)
Dop1-psi(CH2NH)-cyclo(DLys-Arg-Phe-Phe-DTrp-Lys- Thr-4FPhe);

(SEQ ID NO: 12)
Dop1-psi(CH2NH)-cyclo(DLys-Arg-Phe-4Pal-DTrp-Lys-

Thr-Tyr);

(SEQ ID NO: 28)
Dop1-psi(CH2NH)-cyclo(DLys-Arg-Phe-4Pal-DTrp-Lys-

Thr-Phe);

(SEQ ID NO: 29)
Dop1-cyclo(DLys-Arg-The-4Pal-DTrp-Lys-Thr-Phe);

(SEQ ID NO: 30)
Dop1-cyclo(DLys-Arg-Phe-4Pal-DTrp-Lys-Thr-Tyr);
```

```
                                                    (SEQ ID NO: 35)
bis[Dop1-psi(CH₂N)]-cyclo(DLys-Arg-Phe-4Pal-DTrp- Lys-Thr-Phe);

(SEQ ID NO: 45)
bis[Dop1-psi(CH₂N)]-cyclo(DLys-Arg-Phe-Phe-DTrp-

Lys-Thr-4FPhe);
and (SEQ ID NO: 50)
Dop1-cyclo(DLys-Arg-Phe-Phe-DTrp-Lys-Thr-Phe).
```

In another preferred embodiment of the present invention, the somatostatin-dopamine chimeric analog comprises a compound selected from the following list:

```
                                                    (SEQ ID NO: 4)
Dop1-Tyr-psi(CH₂NH)-cyclo(DLys-Arg-Phe-4Pal-DTrp- Lys-Thr-Phe);

(SEQ ID NO: 5)
Dop1-Tyr-psi(CH₂NH)-cyclo(DLys-Arg-Phe-Phe-DTrp-

Lys-Thr-4FPhe);

(SEQ ID NO: 39)
Dop1-Tyr-psi(CH₂NH)-cyclo(DLys-Arg-The-Phe-DTrp-

Lys-Thr-Phe);
and (SEQ ID NO: 40)
Dop1-Tyr-psi(CH₂NH)-cyclo(DLys-Arg-Phe-DTrp-Lys- Thr-Tyr).
```

In another preferred embodiment of the present invention, the somatostatin-dopamine chimeric analog comprises a compound selected from the following list:

```
                                                    (SEQ ID NO: 13)
Dop1-Lys(Dop1)-psi(CH₂NH)-cyclo(DLys-Arg-Phe-4Pal- DTrp-Lys-Thr-Tyr);

(SEQ ID NO: 14)
Dop1-Lys(Dop1)-psi(CH₂NH)-cyclo(DLys-Arg-Phe-4Pal-

DTrp-Lys-Thr-Phe);
and (SEQ ID NO: 52)
Dop1-Lys(Dop1)-psi(CH₂NH)-cyclo(DLys-Arg-Phe-Phe- DTrp-Lys-Thr-4FPhe).
```

Additionally, the present invention provides a method of treating a disease or condition in a subject, said method comprising administering to said subject a therapeutically effective amount of a somatostatin-dopamine chimeric analog described herein, or a pharmaceutically acceptable salt thereof, wherein said disease or disorder is selected from the list consisting of: a neuroendocrine tumor; a vascular disease; a connective tissue disease; an immune disease; a disorder of the gastrointestinal tract, pancreas, kidney, or liver; a metabolic disease; a cachexia; cancer or a tumor of the lung, breast, prostate, liver, thyroid, or blood; a musculoskeletal disorder; a panic disorder; and opioid overdose; and wherein said therapeutically effective amount is the amount effective to treat said disease or disorder in said subject.

In some embodiments, the neuroendocrine tumor is a neuroendocrine tumor of the pituitary. In a first preferred embodiment, the neuroendocrine tumor of the pituitary is an ACTH-producing tumor. Preferably, the ACTH-producing tumor is Cushing's disease. In a second preferred embodiment, the neuroendocrine tumor of the pituitary is a growth hormone producing tumor. Preferably, the growth hormone producing tumor is acromegaly. In a third preferred embodiment, the neuroendocrine tumor of the pituitary is a prolactin-producing tumor. Preferably, the prolactin-producing tumor is a prolactinoma. In a fourth preferred embodiment, the neuroendocrine tumor of the pituitary is hyperprolactinemia or prolactinemia. In a fifth preferred embodiment, the neuroendocrine tumor of the pituitary is thyroid stimulating hormone (TSH) secreting tumor. In a sixth preferred embodiment, the neuroendocrine tumor of the pituitary is "nonfunctioning" pituitary adenoma. In a seventh preferred embodiment, the neuroendocrine tumor of the pituitary is gonadotropinoma.

In some embodiments, the neuroendocrine tumor is carcinoid tumor. In a preferred embodiment, the carcinoid tumor causes carcinoid syndrome. In some embodiments, the neuroendocrine tumor is glucagonoma. In some embodiments, the neuroendocrine tumor is small cell lung carcinoma. In some embodiments, the neuroendocrine tumor is thyroid medullary carcinoma. In some embodiments, the neuroendocrine tumor is VIPoma. In some embodiments, the neuroendocrine tumor is insulinoma. In some embodiments, the neuroendocrine tumor is a functioning or non-functioning gastroenteropancreatic neuroendocrine tumor (GEP-NET). In some embodiments, the disorder of said vascular disease is inappropriate angiogenesis. In some embodiments, the disorder of said vascular disease is restenosis. In some embodiments, the disorder of said vascular disease is retinopathy. In a preferred embodiment, the retinopathy is diabetic retinopathy or proliferative retinopathy. In another preferred embodiment, the retinopathy is macular degeneration, preferably, age-related macular degeneration.

In some embodiments, the connective tissue disease is scleroderma. In some embodiments, the immune disease is rheumatoid arthritis. In some embodiments, the immune disease is inflammation. In some embodiments, the immune disease is fibrosis. In some embodiments, the immune disease is Graves' opthalmopathy. In some embodiments, the immune disease is allograft rejection. In some embodiments, the disorder of the gastrointestinal tract comprises gastric acid secretion, peptic ulcers, inflammatory bowel disease (IBD), or diarrhea. In a preferred embodiment, the IBD is irritable bowel syndrome or Crohn's disease. In another preferred embodiment, the diarrhea is AIDS related or chemotherapy related or watery diarrhea syndrome. In yet another preferred embodiment, the disorder of the gastrointestinal tract is small bowel syndrome, small bowel obstruction, gastroesophageal reflux, duodenogastric reflux, *H. pylori* proliferation, or gastrointestinal bleeding.

In some embodiments, the metabolic disease comprises hyperlipidemia, insulin resistance, Syndrome X, obesity, diabetes, or a diabetes-related disease. In a preferred embodiment, the diabetes-related disease comprises diabetic nephropathy, diabetic neuropathy, diabetic retinopathy, or gastroparesis.

In some embodiments, the cachexia is cardiac cachexia, cancer cachexia, or geriatric cachexia.

In some embodiments, the disease or disorder comprises glioma, anorexia, hypothyroidism, Graves' disease, hyperaldeosteronism, systemic sclerosis, pancreatitis, external and internal pancreatic pseudocysts and ascites, pancreaticocutaneous fistula, nesidoblastosis, hyperinsulinism, gastrinoma, Zollinger-Ellison Syndrome, gastrointestinal hormone secreting tumor, dawn phenomenon, dumping syndrome, hyperparathyroidism, Paget's disease, polycystic ovary disease, orthostatic hypotension, postprandial hypotension, portal hypertension, angiopathy, or graft vessel bleeding.

It is contemplated that the somatostatin-dopamine chimeric compounds of the present invention will be routinely combined with other active ingredients and/or therapies such as anticancer agents, growth hormone antagonists, radiotherapeutic agents, chemotherapeutic agents, antibiotics, antibodies, antiviral agents, analgesics (e.g., a nonsteroidal anti-inflammatory drug (NSAID), acetaminophen, opioids, COX-2 inhibitors), immunostimulatory agents (e.g., cytokines or a synthetic immunostimulatory organic molecules), hormones (natural, synthetic, or semisynthetic), central nervous system (CNS) stimulants, antiemetic agents, antihistamines, erythropoietin, agents that activate complement, sedatives, muscle relaxants, anesthetic agents, anticonvulsive agents, antidepressants, antipsychotic agents, and combinations thereof.

The compounds of the instant invention generally can be provided in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, D-tartaric, L-tartaric, malonic, methane sulfonic and the like. In addition, certain compounds containing an acidic function such as a carboxy can be isolated in the form of their inorganic salt in which the counter-ion can be selected from sodium, potassium, lithium, calcium, magnesium and the like, as well as from organic bases.

The pharmaceutically acceptable salts can be formed by taking about 1 equivalent of a compound of the invention and contacting it with about 1 equivalent or more of the appropriate corresponding acid of the salt which is desired. Work-up and isolation of the resulting salt is well-known to those of ordinary skill in the art.

The compounds of this invention can be administered by oral, parenteral (e.g., intramuscular, intraperitoneal, intravenous or subcutaneous injection, or implant), nasal, vaginal, rectal, sublingual or topical routes of administration and can be formulated with pharmaceutically acceptable carriers to provide dosage forms appropriate for each route of administration. Accordingly, the present invention features pharmaceutical compositions comprising, as an active ingredient, at least one compound of the invention in association with a pharmaceutically acceptable carrier.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as coca butter or a suppository wax.

Compositions for nasal or sublingual administration are also prepared with standard excipients well known in the art.

In general, an effective dose of an active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment, all of which are within the realm of knowledge of one of ordinary skill in the art. Generally, dosage levels of between 0.0001 to 100 mg/kg of body weight daily are administered to humans and other animals, e.g., mammals.

Preferred dosage ranges are from 0.01 to 10.0 mg/kg of body weight. Such dosages may be administered, for example, daily as a single dose or divided into multiple doses.

Synthesis of Somatostatin Agonists

The methods for synthesizing peptide somatostatin agonists are well documented and are within the ability of a person of ordinary skill in the art. For example, peptides may be synthesized on Rink amide MBHA resin (4-(2'4'-dimethoxyphenyl-Fmoc-aminomethyl)-phenoxyacetamido-norleucyl-MBHA resin) using a standard solid phase protocol of Fmoc chemistry. The peptide-resin with a free amino functional group at the N-terminus is then treated with the corresponding compound containing dopamine moiety. The final product is cleaved off from resin with TFA water/TIS mixture.

The synthesis of somatostatin agonists with a substituted N-terminus can be achieved, for example, by following the protocol set forth in PCT publication No. WO 94/04752. Synthesis of somatostatin agonists with a lactam bridge is described in PCT publication No. WO 03/014158.

Synthesis of Dopamine Agonists

The methods for synthesizing many dopamine agonists are also well documented and are within the ability of a person of ordinary skill in the art. Synthetic schemes for the dopamine agonists useful in the somatotstatin-dopamine chimeric compounds disclosed herein can be found in PCT publication Nos. WO 2004/091490 and WO 2002/100888.

Further synthetic procedures are provided in the following reaction schemes and examples.

Examples

Synthesis of Somatostatin-Dopamine Chimers

Somatostatin-dopamine chimers may be synthesized according to the following reaction schemes and examples. Starting material and intermediates for such compounds are commercially available or are prepared using standard methods (see, e.g., *Pharmazie* 39:537 (1984) and U.S. Pat. No. 5,097,031). The following examples are provided to illustrate the invention. They are not meant to limit the invention in any way.

Preparation of D-6-methyl-8β-mesyloxymethyl-ergoline

To a solution of dihydrolysergol (240 mg) in 10 mL of pyridine was added 250 µL of methanesulfonyl chloride. After stirring at room temperature for 2 hours, the reaction mixture was poured into 100 mL of water and extracted with chloroform (2×20 mL). The organic layer was washed with water, dried over MgSO$_4$, and concentrated in vacuo to give 140 mg of a pale brown solid. Further extraction from the aqueous layer after basification with NaHCO$_3$ gave another 100 mg of product. ESI-MS analysis gave the molecular weight of 334.5.

Preparation of D-6-methyl-8β-ergolinylmethylthioacetyl acid

To a solution of the above D-6-methyl-8β-mesyloxymethyl-ergoline (140 ng) in 3 mL of dimethylformide was added powdered K$_2$CO$_3$ (150 mg) followed by 150 µL of ethyl-2-mercaptoacetate and the mixture was heated at 40° C. for 2 hours under nitrogen atmosphere. Solvent was removed in vacuo to dryness, and the residue was partitioned between chloroform and water. The organic layer was then dried (MgSO$_4$), and after evaporation of the solvent, the residue was subjected to preparative silica gel thin layer chromatography using chloroform/methanol (9:1) as developing solvents. The appropriate portion was isolated, extracted with chloroform-methanol and solvents were removed in vacuo to dryness to afford 100 mg of a pale brown solid. ESI-MS analysis gave the molecular weight of 359.2. This ester was hydrolyzed with 1N LiOH and monitored by HPLC. After hydrolysis was completed, it was acidified by dilute HCl to pH 3 to generated D-6-methyl-8β-ergolinylmethylthioacetyl acid. ESI-MS analysis gave the molecular weight of 331.5 which is in agreement of theoretical amount of 330.5.

Preparation of D-6-methyl-8β-ergolinylmethylthioethanal

The following additional dopamine moieties were prepared in accordance with the synthetic scheme shown below:

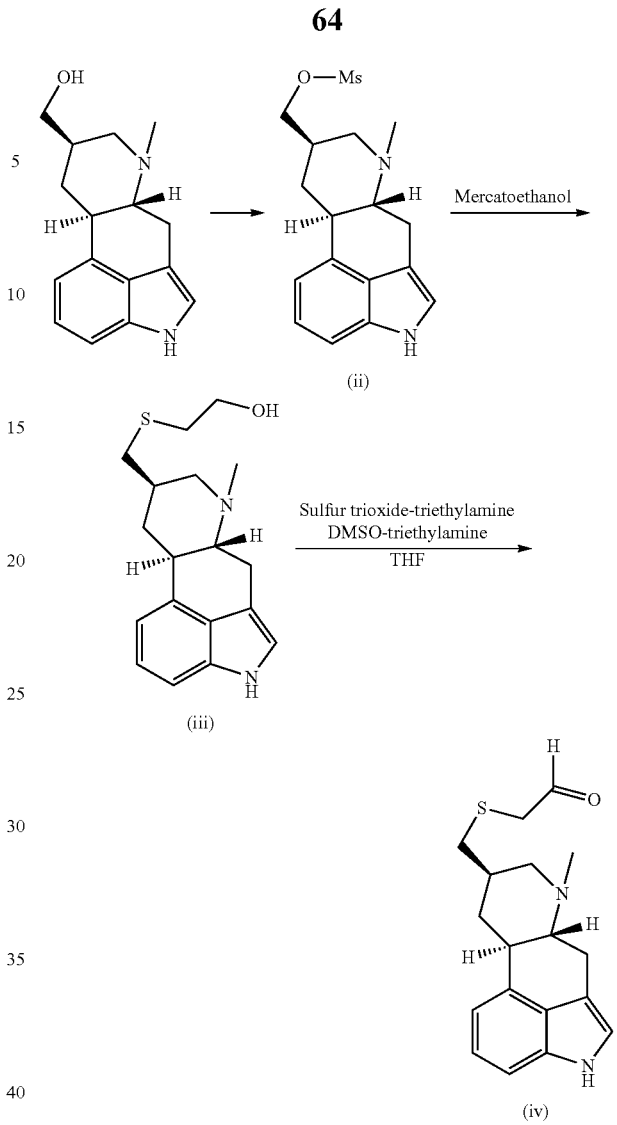

Step 1: Preparation of D-6-methyl-8β-mesyloxymethyl-ergoline (ii)

To an ice-cooled suspension of D-6-methyl-8β-hydroxymethyl-ergoline (2.8 g) in 50 mL of pyridine was added dropwise 2.5 mL of methanesulfonylchloride (2.5 eq.) and the mixture was allowed to warm to room temperature and stirred overnight. The mixture was poured into an ice-NaHCO$_3$ mixture and the alkaline aqueous mixture was extracted with chloroform several times (3×50 mL). Volatile substances were evaporated in vacuo to dryness and trace of pyridine was further removed by co-evaporation with toluene. ESI-MS analysis gave the molecular weight of 335.4.

Step 2: Preparation of (D-6-methyl-8β-ergolinylmethyl)thioethanol (iii)

To a mixture of D-6-methyl-8β-mesyloxymethyl-ergoline (5 g), powdered K$_2$CO$_3$ (7.7 g) in 60 mL of DMF was added 3.5 mL of 2-mercaptoethanol and the mixture was heated at 50° C. to 60° C. (bath) overnight under nitrogen atmosphere. The mixture was diluted with chloroform (100 mL), filtered and the filter cake was washed with chloroform-methanol.

The filtrate was evaporated in vacuo to dryness and it was partitioned between chloroform/methanol and water. The organic layer was then dried over MgSO₄, and after evaporation of the solvents, the residue was triturated with methanol. Pale yellow solid was collected by filtration (1.9 g). The mother liquor was evaporated in vacuo to dryness. The residue was chromatographed on silica gel (30 g) using chloroform/methanol (19:1) as eluents. Appropriate fractions were pooled and the solvents were removed in vacuo to dryness to afford 1.0 g of a pale brown solid. ESI-MS analysis gave the molecular weight of 317.3.

Step 3: Preparation of
D-6-methyl-8β-ergolinylmethylthioethanal (iv)

To an ice cooled mixture of D-6-methyl-8β-ergolinylmethylthioethanal (480 mg) in DMSO/triethylamine (2:1, 4.5 mL) diluted with 5 mL of THF was added a solution of sulfur trioxide-triethylamine complex (770 mg, 2.8 eq.) in 5 mL of DMSO with stirring. The reaction mixture was stirred at 0-5° C. for 30 minutes and 1 hour at room temperature. 30 mL of 10% aqueous acetic acid was added and the mixture was stirred for 1 hour. 5N—NaOH was slowly added to adjust pH to 8-9. A pale pink solid was collected by filtration, washed with water, and then dried. ESI-MS analysis gave the molecular weights of 315.5, 629.4, 943.1, and 472.6.

Synthetic Procedure for Dop1-Tyr-psi(CH₂NH)-cyclo(DLys-Arg-Phe-4Pal-DTrp-Lys-Thr-Phe)
(Compound 4; SEQ ID NO:4)

The peptide moiety of Compound 4 was automatically synthesized on an Applied Biosystems (Foster City, Calif., USA) model 433A peptide synthesizer based on Fmoc chemistry. Pre-loaded Fmoc-Phe-2ClTrt resin with substitution of 0.58 mmol/g was used and synthesis was carried out on a 0.2 mmol scale. The Fmoc amino acid cartridges were obtained from AnaSpec (San Jose, Calif., USA). The Fmoc amino acids with the side chain protections were as follows: Fmoc-Thr(tBu)-OH, Fmoc-Lys(Boc)-OH, Fmoc-DTrp(Boc)-OH, Fmoc-Arg(Pbf)-OH, Fmoc-DLys(Mtt)-OH, and Fmoc-4Pal (Chem-Impex Inc.; Wood Dale, Ill., USA). The synthesis was carried out on a 0.25 mmol scale. The ABI 433A peptide synthesizer was programmed to perform the following reaction cycle: washing with NMP; removing Fmoc protecting group with 20% piperidine in NMP for 10 minutes; washing with NMP; and coupling with pre-activated amino acid for 1 hour. The resin was double coupled successively according to the sequence until peptide chain assembly was finished. During washing and removing of Fmoc cycles, the Fmoc amino acid (4 eq., 1 mmol) was first pre-activated with 2 mL of a solution of 0.45M HBTU/HOBt in DMF. This activated amino acid ester, 1 mL of 2M DIEA and 2.5 mL of NMP were added to the resin. Before aminoalkylation, the resin was treated with 25% piperidine in DMF for 40 minutes and washed with DMF, MeOH and DCM.

5 mmol of Fmoc-Tyr(tBu)-OH in DCM was reacted with 5.1 mmol of N,O-dimethylhydroxylamine hydrochloride, PyBOP and DIEA to convert to a Weinreb amide. Then 1 mmol of it was dissolved in 10 mL of anhydrous THF and cooled down in a salt-ice bath (−5° C.) for 15 minutes, to which 1 mmol of LAH (1 mL) was slowly dropped in 20 minutes. The reaction was kept cold in an ice bath (0° C.) and stirred for additional 1 hour. The reaction was quenched by addition of 10 mL of 10% KHSO₄ and diluted with 50 mL of DCM. The aqueous solution was further extracted with DCM (50 mL, 30 mL, and 20 mL). All organic layers were washed with 10% KHSO₄ (20 mL×3) and brine (20 mL×3). After drying over Na₂SO₄, it was evaporated to dryness. HPLC showed a broad peak. This crude aldehyde (Fmoc-Tyr(tBu)-CHO) was dissolved in 2.5 mL of DMF and mixed with the N-terminal free resin in a solution of 10 mL of DMF and 125 µL of AcOH, to which 2.1 mmol (136.8 mg) of NaBH₃CN was added in 5 portions in half hour increments. The reaction was shaken overnight. An aliquot of resin was cleaved, and the reaction was confirmed to be complete.

After washing, the resin was treated with MeOH for 2 hours, and then mixed with 25% piperidine/DMF overnight and the resin was washed successively with DMF, MeOH and DCM, and then coupled with D-6-methyl-8β-ergolinylmethylthioacetyl acid (3 eq.). PyAOP (5 eq.) and DIEA (10 eq.) overnight. The cleavage of an aliquot showed the coupling was complete.

After washing with DCM, the resin was treated with 32 mL of a solution (for 0.159 mmol scale resin) containing TFA/DCM (1:99) for 30 minutes, then filtered into 0.583 mL of TEA and evaporated to dryness. This process was repeated three more times. The crude linear product was dissolved in 77.5 mL of DCM, to which 2 eq. of PyAOP, 2.5 eq. of HOBt and 16 eq. of DIEA were added. The lactam formation was monitored by HPLC.

The cyclized protected crude product was treated with a solution of TFA/TIS/H₂O/DTT (20 mL, 1.26 mL, 1.34 mL, 1.25 g) for 6 hours and filtered in 150 mL of cold ether. After centrifugation, the precipitate was ready for purification.

The crude product was dissolved in 50% AcOH in water, diluted with 10 folds of 0.1% TFA in water. Acetonitrile was added dropwise to make a clear solution. Purification was carried out on a reverse-phase preparative Waters® HPLC/MS using a Luna C18 column from Phenomenex (100×21.2 mm, 100 Å, 5 µm). The peptide was eluted from the column with a gradient from 30-60% B in 35 minutes, where A was 0.1% TFA in water and B was 0.1% TFA in acetonitrile. The fractions were checked on an ACQUITY UPLC™ (Waters Corporation; Milford, Mass., USA) and fractions containing pure product were combined and lyophilized to dryness.

Synthetic Procedure for Dop1-Tyr-psi(CH₂NH)-cyclo(DLys-Arg-Phe-Phe-DTrp-Lys-Thr-4FPhe)
(Compound 5; SEQ ID NO:5)

Compound 5 was synthesized substantially according to the synthetic procedure for Compound 4, except that Fmoc-4FPhe-2ClTrt resin was used and Phe was replaced with 4Pal in the peptide sequence.

Synthetic Procedure for Dop1-psi(CH₂NH)-cyclo
(DLys-Arg-Phe-Phe-DTrp-Lys-Thr-4FPhe) (Compound 6; SEQ ID NO:6)

Compound 6 was synthesized substantially according to the synthetic procedure for Compound 5, except that Dop1-CHO was used instead of Fmoc-Tyr(tBu)-CHO.

Synthetic Procedure for Dop1-psi(CH₂NH)-cyclo
(DLys-Arg-Phe-4Pal-DTrp-Lys-Thr-Tyr) (Compound 7; SEQ ID NO: 12)

Compound 7 was synthesized substantially according to the synthetic procedure for Compound 6, except that Phe was replaced with 4Pal in the peptide sequence and the C-terminus was Tyr instead of 4FPhe.

Alternative Synthetic Procedure for Dop1-psi (CH$_2$NH)-cyclo(DLys-Arg-Phe-4Pal-DTrp-Lys-Thr-Tyr) (Compound 7; SEQ ID NO:12)

Fmoc-Tyr(tBu)-OH (12 mmole, 5.51 g) was dissolved in solution of 40 mL of DCM and 20 mL of DMF. To this solution, 2-chlorotrityl resin with substitution of 1.5 mmol/g (12.135 mmole, 8.09 g) and diisopropylethylamine (36 mmol, 6.27 mL) were added. After 3 hours, the resin was filtered and washed 3 times with DMF and then DCM. The resin was then treated for 1.5 hours with 10% DIEA in MeOH. The resin was sequentially washed with DMF, DCM and MeOH and dried overnight. Substitution of the resin was determined as 0.58 mmoles/g according to 1,8-diazabicyclo[5.4.0]undec-7-ene procedure in M. Gude, et al., *Lett. Pep. Sci.* 9, 203. (2003).

The titled peptide was prepared using Symphony® synthesizer (Protein Technologies, Inc., Tucson, Ariz., USA) based on Fmoc chemistry. 0.345 g of pre-loaded Fmoc-Tyr(tBu)-2-ClTrt resin with substitution of 0.58 mmol/g was used and synthesis was carried out on a 0.2 mmol scale. The Fmoc amino acids utilized with side chain protecting groups were as follows: Fmoc-Thr(tBu)-OH, Fmoc-Lys(ivDde)-OH, Fmoc-DTrp(Boc)-OH, Fmoc-Phe-OH, Fmoc-4Pal-OH, and Fmoc-Arg(Pbf)-OH (CBL Biopharma, Boulder, Colo., USA) and Fmoc-DLys (Mtt)-OH (Chem-Impex Int'l Inc., Wood Dale, Ill., USA). The synthesizer was programmed to perform the following reaction cycles: washing with DMF; removing Fmoc protecting group with 20% piperidine in DMF for 15 minutes for the first 3 amino acids and 30 minutes for the Fmoc-DTrp(Boc)-OH through the end of the peptide; washing with DMF; and coupling with 0.9 eq. of HCTU. The resin was double coupled successively according to the sequence until peptide chain assembly was finished. The synthesis was programmed to carry out a final deprotection to remove Fmoc. The resin was mixed with 12 eq. excess of (Boc)$_2$O and 6 eq. of DIEA in 4 mL of DMF for 2 hours, which was repeated once. An aliquot of global cleavage showed MS of 1383, which was in agreement with the calculated molecular weight of 1382.6. UPLC (5% to 80% B in 5 min, where A was 0.1% TFA in water and B was 0.1% TFA in acetonitrile) showed product of R$_t$=2.82.

The above Boc-DLys(Mtt)-Arg(Pbf)-Phe-4Pal-DTrp(Boc)-Lys(ivDde)-Thr(tBu)-Tyr(tBu)-2-ClTrt resin was treated with 25 mL of cold TFA/TIS/DCM (Jan. 5, 1994) for 30 minutes to afford selective cleavage. The filtrate DCM cleavage solution was neutralized by addition of 0.47 mL of TEA while in an ice bath. This was repeated twice, then three neutralized filtrates were combined and cyclization was immediately carried out using 5 eq. of PyBOP, 8 eq. of DIEA and a catalytic amount of DMF overnight. The UPLC analysis showed the retention time was shifted from 2.83 to 3.946 (gradient was 50% to 100% Buffer B in 5 minutes). MS showed 1929 (linear is 1947). The mixture was evaporated to dryness and taken into 20 mL of water and triturated to obtain an oily precipitate. The residue was mixed with 12 mL of TFA solution containing 0.8 mL of TIS, 0.8 mL of water and 0.65 g of DTT for 4 hr. The mixture was poured into 80 mL of ether and centrifuged to get precipitate. The crude cyclized peptide was dissolved in 5 mL of 50% AcOH in water and diluted 10 fold with 0.1% TFA in water. A small amount of ACN was added to make the solution clear if needed. It was loaded onto a reversed-phase preparative Luna C18 column from Phenomenex (100×21.2 mm, 100 Å, 5 μm). The peptide was eluted with a gradient from 20-50% B in 50 minutes, where A was 0.1% TFA in water and B was 0.1% TFA in acetonitrile. The fractions were checked on an Acquity UPLC (Waters) and fractions containing pure product were combined and lyophilized to dryness. ESI-MS analysis showed the correct product with 1365.2, in agreement with the calculated molecular weight of 1365. It generated 96 mg with 95% purity. The average yield was 29.8% based on the starting resin.

To a solution of D-6-methyl-8β-ergolinylmethylthioethanol (1.5 g, 4.7 mmol) in TEA/DMSO/THF (6 mL/12 mL/30 mL), sulfur trioxide-triethylamine complex (3.44 g, 19 mmol) in DMSO (10 mL) was added dropwise at 0-10° C. After the addition, the mixture was stirred at room temperature for 2 hours. HPLC showed the reaction was completed. The pH was adjusted to 2-3 with 5% HCl below 10° C. The solution was stirred at room temperature for 1 hour, then the pH was adjusted to 8-9 with 5M NaOH, the mixture was extracted with EtOAc, the combined organic layers were washed with brine, dried with Na$_2$SO$_4$ and concentrated to give Dop1-CHO D-6-methyl-8β-ergolinylmethylthioethanal (1.5 g, average 80-90% of purity). ESI-MS analysis gave the molecular weight at 315.28 (in agreement with the calculated molecular weight of 314.15). It was used for the next reaction without further purification.

The freshly made Dop1-CHO was dissolved in MeOH to make a concentration of stock solution be 0.0527 mmol. A stock solution of NaBH$_3$CN of 30 mg/ml MeOH (0.477 mmol/mL) was prepared. 215.6 mg of NH$_2$-[DLys-Arg-Phe-4Pal-DTrp-Lys(ivDde)-Thr-Tyr] (0.158 mmol) was dissolved in 20 mL of MeOH. To which 1.4 eq. of Dop1-CHO (0.22 mmol, 4.2 mL of the stock solution) was added, following by NaBH$_3$CN (1.5 eq., 0.237 mmol) was added over the period of 1 hour in three portions (3×0.55 mL). The reaction was followed by UPLC and infusion MS. After 2.5 hours, the starting peptide was consumed and the reaction was concentrated under vacuum to give a crude product.

To the crude peptide Dop1-psi(CH$_2$NH)-cyclo[DLys-Arg-Phe-4Pal-DTrp-Lys(ivDde)-Thr-Tyr], 5% hydrazine in DMF (12 mL) was added. The resulting mixture was stirred at room temperature for 1 hour. The reaction mixture was monitored by HPLC and ESI, which indicated the starting material was consumed. The reaction mixture was acidified to pH 4 using TFA and concentrated under vacuum. The crude product was purified by HPLC. A reversed-phase preparative Luna C18 column from Phenomenex (250×21.2 mm, 100 Å, 5 μm) was used. The peptide was eluted with a gradient from 10-30% B in 40 minutes, where A was 0.1% TFA in water and B was 0.1% TFA in acetonitrile. It gave 94 mg of final product with 94% purity. It gave 41% yield based on peptide; 29% yield based on Dop1-OH. ESI-MS analysis gave the molecular weight of 1456.8 in agreement with the calculated molecular weight of 1456.8.

Synthetic Procedure for Dop1-Lys(Dop1)-psi (CH$_2$NH)-cyclo(DLys-Arg-Phe-4Pal-DTrp-Lys-Thr-Tyr) (Compound 8; SEQ ID NO:13)

Compound 8 was synthesized substantially according to the synthetic procedure for Compound 7, except that Fmoc-Lys(Fmoc)-CHO was used for aminoalkylation. The resin was then treated with 25% piperidine/DMF to remove the Fmoc protecting groups on Lys, and the free amino groups were coupled with D-6-methyl-8β-ergolinylmethylthioethanal.

Synthetic Procedure for Dop1-Lys(Dop1)-psi(CH₂NH)-cyclo(DLys-Arg-Phe-4Pal-DTrp-Lys-Thr-Phe) (Compound 9; SEQ ID NO: 14)

Compound 9 was synthesized substantially according to the synthetic procedure for Compound 8, except that the C-terminal amino acid was Phe instead of Tyr.

Synthetic Procedure for Dop1(SO₂)-psi(CH₂NH)-cyclo(DLys-Arg-Phe-4Pal-DTrp-Lys-Thr-Tyr) (Compound 20; SEQ ID NO:25), Dop1[(R)SO]-psi(CH₂NH)-cyclo(DLys-Arg-Phe-4Pal-DTrp-Lys-Thr-Tyr) (Compound 11; SEQ ID NO: 16), and Dop1[(S)SO]-psi(CH₂NH)-cyclo(DLys-Arg-Phe-4Pal-DTrp-Lys-Thr-Tyr) (Compound 12; SEQ ID NO: 17)

Compounds 20, 11 and 12 were obtained from oxidation of Compound 7. The purified powder of Compound 7 was dissolved in water to make a solution of 3.433 mM. 1.1 fold of sodium periodate was dissolved in Dulbecco's PBS (20 mM PBS, 137 mM NaCl) to make concentration of 3.84 mM. The solution was mixed and stirred at room temperature. After 0.5 hour, ESI-MS analysis gave the molecular weights of the oxidized products of 1472.1 (M+16) and 1486 (M+32). UPLC showed three major peaks. 50 fold excess of ethylene glycol was used to quench the reaction. It was purified by HPLC on VyDac 218TP10510 using gradient: 0-10% B in 5 minutes, 10-35% B in 55 minutes, monitored at UV 285 nm (A: 100% water with 0.1% TFA; B: 100% acetonitrile with 0.1% TFA). All fractions were pulled based on Infusion MS and HPLC. Those fractions with MS 1486.5 and purity of 99.6% were Compound 20. Those fractions with MS 1472.7 showed that they are a mixture in HPLC, which was further purification by the same gradient as those described above. Compound 11 was characterized as retention time at 21.032, and Compound 12 was characterized as retention time at 20.7 under condition of slower gradient (0-20% B in 10 minutes, then to 35% in 30 minutes).

The physical data of select compounds according to the present invention are compiled in Table II.

TABLE II

| Compound No. | Molecular weight (calculated) | Molecular weight (ESI-MS) | Purity (%; HPLC) |
|---|---|---|---|
| 1 | 1425.8 | 1426.2 | 97.4 |
| 2 | 1439.8 | 1439.6 | 98.8 |
| 3 | 1453.8 | 1454.1 | 96.6 |
| 4 | 1604.0 | 1603.5 | 97.1 |
| 5 | 1621.0 | 1620.6 | 95.6 |
| 6 | 1457.8 | 1457.7 | 97.6 |
| 6A | 1475.8 | 1475.6 | 95.0 |
| 6B | 1475.8 | 1475.6 | 96.4 |
| 6C | 1457.8 | 1457.6 | 95.8 |
| 6D | 1457.8 | 1457.6 | 97.3 |
| 6E | 1529.8 | 1529.7 | 90.7 |
| 7 | 1456.8 | 1456.9 | 97.7 |
| 8 | 1897.4 | 1897.5 | 99.2 |
| 9 | 1881.4 | 1881.7 | 96.8 |
| 10 | 1489.8 | 1489.6 | 86.7 |
| 11 | 1472.8 | 1472.6 | 98.2 |
| 12 | 1472.8 | 1472.7 | 98.9 |
| 13 | 1637.0 | 1636.8 | 91.6 |
| 14 | 1473.8 | 1473.7 | 96.4 |
| 15 | 1620.0 | 1619.9 | 95.1 |
| 16 | 1929.4 | 1929.5 | 95.4 |
| 17 | 1913.4 | 1913.5 | 82.2 |
| 19 | 1653.0 | 1652.7 | 99.2 |
| 20 | 1488.8 | 1486.7 | 99.6 |
| 21 | 1636 | 1635.8 | 87.2 |
| 22 | 1496.8 | 1496.9 | 98.4 |
| 23 | 1440.8 | 1440.8 | 95.3 |
| 24 | 1454.8 | 1454.6 | 99.3 |
| 25 | 1470.8 | 1470.6 | 99.8 |
| 26 | 1439.8 | 1439.8 | 96.3 |
| 27 | 1660.0 | 1660.0 | 92.1 |
| 28 | 1538.9 | 1538.7 | 95.9 |
| 28A | 1646.0 | 1646.5 | 98.3 |
| 29 | 1739.3 | 1739.4 | 90.6 |
| 29A | 1496.8 | 1497.0 | 99.0 |
| 30 | 1589.0 | 1588.4 | 98.9 |
| 31 | 1603.0 | 1602.5 | 95.3 |
| 32 | 1603.0 | 1602.4 | 99.6 |
| 33 | 1619.0 | 1618.7 | 98.3 |
| 34 | 1471.8 | 1472.2 | 98.3 |
| 35 | 1755.3 | 1755.3 | 97.7 |
| 37 | 1617.0 | 1616.7 | 99.2 |
| 38 | 1604.0 | 1603.5 | 95.5 |
| 39 | 1756.3 | 1756.3 | 97.2 |
| 40 | 1738.3 | 1738.4 | 94.5 |
| 41 | 1603.0 | 1602.4 | 98.1 |
| 42 | 1696.1 | 1696 | 98.8 |
| 43 | 1589.0 | 1588.6 | 99.7 |
| 44 | 1453.8 | 1453.1 | 97.3 |
| 46 | 1620.0 | 1619.6 | 95.5 |
| 47 | 1898.4 | 1898.5 | 97.0 |
| 48 | 1503.8 | 1503.7 | 95.8 |

Somatostatin Receptor Radioligand Binding Assays

The affinities of a test compound for the human somatostatin receptors were determined by radioligand binding assays in CHO—K1 cells stably transfected with each of the human somatostatin receptor subtypes, hSSTR1-5. The cDNA coding sequences of hSSTR1 (GenBank accession No. NM_001049.1), hSSTR2 (GenBank accession No. XM_012697.1), hSSTR3 (GenBank accession No. XM_009963.1), hSSTR4 (GenBank accession No. NM_001052.1), and hSSTR5 (GenBank accession No. XM_012565.1) were subcloned into the mammalian expression vector pcDNA3.1 (Life Technologies). Clonal cell lines stably expressing each of the somatostatin receptors were obtained by transfection into CHO—K1 cells (ATCC) and subsequently selected with culture media containing 0.8 mg/mL of G418 (Life Technologies).

Membranes for in vitro receptor binding assays were obtained by the following procedures. CHO—K1 cells expressing one of the somatostatin receptors were homogenized in ice-cold buffer with 10 mM Tris-HCl, 5 mM EDTA, 3 mM EGTA, 1 mM phenylmethylsuphonyl fluoride, pH 7.6, using Polytron PT10-35GT (Kinematica) at 18,000 rpm for 30 seconds and centrifuged at 500×g for 10 minutes. The supernatant containing the plasma membranes was centrifuged at 100,000×g for 30 minutes and the pellet was resuspended in buffer containing 20 mM glycine-glycine, 1 mM MgCl₂, 250 mM sucrose, pH 7.2, for storage at −80° C.

For the SSTR1, 2 and 5 assays, membranes and various concentrations of test compounds were incubated in 96-well plates for 60 minutes at 25° C. with 0.05 nM [$^{125}$I-Tyr$^{11}$]-SRIF-14 (for hSSTR1; PerkinElmer Life Science), 0.05 nM [$^{125}$I-Tyr]-seglitide (for hSSTR2; PerkinElmer Life Science) or 0.05 nM [$^{125}$I-Tyr]-[DPhe-cyclo(Cys-Tyr-DTrp-Lys-Val-Cys)-Thr-NH₂](for hSSTR5; PerkinElmer Life Science) in 50 mM HEPES, 0.2% BSA, 0.1 mM MgCl₂, pH 7.5.

For the hSSTR3 and 4 assays, membranes and various concentrations of test compounds were incubated in 96-well plates for 60 minutes at 25° C. with 0.05 nM [$^{125}$I-Tyr$^{11}$]-

SRIF-14 (PerkinElmer Life Science) in 50 mM HEPES, 0.2% BSA, 5 mM MgCl$_2$, 200 KIU/mL trasylol, 0.02 mg/mL bacitracin, and 0.02 mg/mL phenylmethylsuphonyl fluoride, pH 7.5.

The incubations were terminated by rapid filtration through GF/C glass microfiber filter plates (pre-wet with 0.3% polyethyleneimine and 0.1% BSA) using a 96-well cell harvester (Brandel). Plates were washed six times with 1 mL/well aliquots of ice-cold buffer containing 50 mM Tris buffer, pH 7.7. Specific binding was defined as the total radioligand bound minus the bound in the presence of 1000 nM SRIF-14.

The results of the somatostatin receptor radioligand binding assays as described hereinabove are provided in Table III for select compounds according to the present invention.

TABLE III

| Compound No. | hSSTR1 Ki (nM) ± SEM | hSSTR2 Ki (nM) ± SEM | hSSTR3 Ki (nM) ± SEM | hSSTR4 Ki (nM) ± SEM | hSSTR5 Ki (nM) ± SEM | hDRD2 Ki (nM) ± SEM |
|---|---|---|---|---|---|---|
| 1 | | 0.04 ± 0.02 | | | | 10.8 ± 1.4 |
| 2 | | 0.79 ± 0.06 | | | | 6.9 ± 0.4 |
| 3 | | 0.72 ± 0.17 | | | | 45.2 ± 4.9 |
| 4 | 38.1 ± 12.5 | 0.12 ± 0.01 | 10.6 ± 0.5 | 93.5 ± 47.7 | 0.92 ± 0.1 | 182.5 ± 1.7 |
| 5 | 9.0 ± 0.3 | 0.34 ± 0.09 | 1.5 ± 0.3 | 25.2 ± 9.0 | 1.65 ± 0.8 | 28.5 ± 12.8 |
| 6 | 32.2 ± 8.1 | 0.30 ± 0.06 | 2.1 ± 0.9 | 61.9 ± 25.0 | 0.52 ± 0.1 | 100.9 ± 17.9 |
| 6A | | 0.35 ± 0.00 | | | | 16.9 ± 0.2 |
| 6B | | 0.25 ± 0.03 | | | | 25.4 ± 7.9 |
| 6C | | 0.15 ± 0.04 | | | | 30.3 ± 3.7 |
| 6D | | 0.54 ± 0.17 | | | | 31.8 ± 11.8 |
| 6E | | 5.48 ± 3.38 | | | | 40.4 ± 13.2 |
| 7 | 100.3 ± 18.5 | 0.08 ± 0.02 | 13.1 ± 2.8 | 10.8 ± 2.8 | 0.51 ± 0.1 | 34.3 ± 16.8 |
| 8 | 106.5 ± 7.9 | 0.21 ± 0.08 | 7.5 ± 0.3 | 60.7 ± 15.7 | 1.49 ± 0.3 | 112.8 ± 35.0 |
| 9 | 41.9 ± 21.1 | 0.13 ± 0.06 | 4.0 ± 0.5 | 24.0 ± 3.6 | 1.54 ± 0.3 | 39.2 ± 8.3 |
| 10 | 6.6 | 0.17 ± 0.05 | 27.9 | 20.6 | 0.16 ± 0.1 | 56.4 ± 11.2 |
| 11 | 159.6 ± 22.5 | 0.05 ± 0.00 | 30.9 ± 11.7 | 2.1 ± 0.4 | 0.09 ± 0.0 | 79.7 ± 21.4 |
| 12 | 98.9 ± 2.3 | 0.06 ± 0.01 | 143.3 ± 65.2 | 3.2 ± 0.7 | 0.74 ± 0.4 | 255.1 ± 223.8 |
| 13 | 8.6 | 0.04 ± 0.02 | | | 0.23 | 32.5 ± 8.9 |
| 14 | 6.0 | 0.05 ± 0.01 | | | 0.36 | 76.5 ± 13.9 |
| 15 | 64.4 | 0.02 ± 0.01 | | | 0.08 | 149.3 ± 11.3 |
| 16 | | 0.04 ± 0.03 | | | | 22.5 ± 1.9 |
| 17 | 91.4 | 0.08 ± 0.05 | | | 0.86 | 67.6 ± 18.4 |
| 19 | | 0.16 ± 0.17 | | | | >1000 |
| 20 | 689.3 | 0.02 ± 0.01 | | | 0.33 | 114.6 ± 41.3 |
| 21 | | 0.02 ± 0.01 | | | | >1000 |
| 22 | | 0.35 ± 0.18 | | | | 199.5 ± 65.0 |
| 23 | | 0.09 ± 0.00 | | | | 328.3 ± 19.3 |
| 24 | 47.7 ± 30.7 | 0.08 ± 0.01 | | | 2.39 | 175.3 ± 25.6 |
| 25 | 41.9 ± 17.6 | 0.05 ± 0.01 | | | 0.95 ± 0.1 | 272.4 ± 119.0 |
| 26 | 59.0 | 2.23 ± 0.97 | | | | 309.0 ± 56.6 |
| 27 | 24.4 ± 12.0 | 0.32 ± 0.04 | 0.9 ± 0.1 | 7.3 ± 1.3 | 0.53 ± 0.1 | 276.8 ± 55.5 |
| 28 | | 0.75 ± 0.27 | | | | 39.9 ± 10.4 |
| 28A | | 0.04 ± 0.02 | | | | 14.0 ± 3.4 |
| 29 | 26.7 | 0.14 ± 0.02 | | | 2.37 | 135.2 ± 66.1 |
| 29A | | 0.13 ± 0.00 | | | | 46.8 ± 7.4 |
| 30 | | 0.40 ± 0.06 | | | | 24.2 ± 2.0 |
| 31 | | 0.51 ± 0.10 | | | | 38.6 ± 28.6 |
| 32 | 5.3 ± 2.9 | 0.28 ± 0.07 | | | 1.58 | 44.0 ± 1.0 |
| 33 | 10.4 ± 3.2 | 0.24 ± 0.10 | | | 0.82 ± 0.4 | 15.0 ± 2.6 |
| 34 | | 4.55 ± 1.15 | | | | 298.9 |
| 35 | 99.7 | 0.17 ± 0.06 | | | | 345.2 ± 7.45 |
| 37 | | 1.38 ± 0.36 | | | 2.45 | 25.3 ± 2.4 |
| 38 | | 0.76 ± 0.23 | | | | 179.4 ± 113.3 |
| 39 | | 3.72 ± 2.01 | | | | 329.7 ± 59.5 |
| 40 | | 3.17 ± 1.41 | | | | 444.9 ± 142.7 |
| 41 | | 0.37 ± 0.00 | | | | 8.5 ± 3.6 |
| 42 | | 0.69 | | | | 285.3 |
| 43 | | 1.07 ± 0.39 | | | | |
| 44 | | 1.37 ± 0.23 | | | 1.38 ± 0.3 | 199.6 ± 25.8 |
| 46 | | 0.52 ± 0.06 | | | | 31.6 ± 6.6 |
| 47 | 29.0 | 0.58 ± 0.27 | | | | 84.2 ± 7.5 |
| 48 | | 0.25 ± 0.10 | | | | 19.4 ± 2.8 |

Dopamine Receptor Radioligand Binding Assay

The affinity of a test compound for the human dopamine receptor subtype hDRD2 was determined by radioligand binding assays in CHO—K1 cells stably transfected with hDRD2 receptor, as follows. The cDNA coding sequence of hDRD2 (GenBank accession No. X51362) was subcloned into the mammalian expression vector pcDNA3.1/GS (Life Technologies). Clonal cell lines stably expressing hDRD2 were obtained by transfection into CHO—K1 cells and subsequently selected with culture medium containing 0.3 mg/mL of zeocin (Life Technologies).

Membranes for in vitro receptor binding assays were obtained by the following procedures. CHO—K1 cells expressing hDRD2 were homogenized in ice-cold buffer with 10 mM Tris-HCl, 5 mM EDTA, 3 mM EGTA, 1 mM phenylmethylsuphonyl fluoride, pH 7.6 using Polytron PT10-35GT (Kinematica) at 18,000 rpm for 30 seconds and centrifuged at 500×g for 10 minutes. The supernatant containing the plasma membranes was centrifuged at 100,000×g for 30 minutes and the pellet was resuspended in buffer containing 20 mM glycine-glycine, 1 mM $MgCl_2$, 250 mM sucrose, pH 7.2 for storage at −80° C.

For assay, membranes and various concentrations of test compounds were incubated in 96-well plates for 60 minutes at 25° C. with 0.25 nM [$^3$H]-spiperone (PerkinElmer Life Science) in 50 mM Tris HCl, 120 mM NaCl, 5 mM KCl, 2 mM $CaCl_2$, and 1 mM $MgCl_2$. The incubations were terminated by rapid filtration through GF/C glass microfiber filter plates (pre-wet with 0.3% polyethyleneimine and 0.1% BSA) using a 96-well cell harvester (Brandel). Plates were washed six times with 1 mL/well aliquots of ice-cold buffer containing 50 mM Tris buffer, pH 7.7. Specific binding was defined as the total radioligand bound minus the bound in the presence of 1000 nM (+) butaclamol.

The results of the dopamine receptor radioligand binding assay as described hereinabove are provided in Table III for select compounds according to the present invention.

Intracellular Calcium Mobilization Assays

The ability of select compounds according to the present invention to activate hSSTR2 and hDRD2 was determined by the intracellular calcium mobilization assay using FLIPR Calcium 4 assay kit (Molecular Devices).

Cells expressing hSSTR2 or hDRD2 were plated in 384-well microplates in tissue culture media and incubated for 16-24 hours at 37° C. in a humidified atmosphere with 5% $CO_2$. Medium was replaced by loading buffer containing Hank's buffered saline, 20 mM HEPES, 2.5 mM probenecid and Calcium 4 dye, and the plates were incubated at 37° C. for 60 minutes. Various concentrations of the test compounds were applied to the cells during the fluorescence measurement with excitation at 485 nm and emission at 525 nm using the Flexstation III microplate reader (Molecular Devices).

The half maximal effective concentrations ($EC_{50}$) were calculated by fitting data to sigmoid dose-response curves using GraphPad Prism version 5.03 (GraphPad Software, San Diego, Calif., USA). % $E_{max}$ values represent the maximal effect of the test compound in percentage of the maximal effect of SRIF-14.

The results of the intracellular calcium mobilization assays as described hereinabove are provided in Table IV for select compounds according to the present invention.

TABLE IV

| Compound No. | hSSTR2 $EC_{50}$ (nM) ± SEM | % $E_{max}$ ± SEM | hDRD2 $EC_{50}$ (nM) ± SEM | % $E_{max}$ ± SEM |
|---|---|---|---|---|
| 1 | 3.1 | 98.7 | 22.5 ± 0.5 | 102.1 ± 0.4 |
| 2 | 21.1 ± 6.7 | 100.4 ± 1.7 | 55.7 ± 12.4 | 84.0 ± 7.6 |
| 3 | 137.3 ± 63.8 | 98.8 ± 19.2 | 212.5 ± 85.6 | 84.1 ± 12.2 |
| 4 | 7.6 ± 1.5 | 100.3 ± 2.9 | 20.1 ± 2.6 | 105.7 ± 2.4 |
| 5 | 14.6 ± 1.9 | 97.0 ± 3.6 | 30.1 ± 5.3 | 98.7 ± 2.3 |
| 6 | 12.7 ± 3.6 | 99.1 ± 0.6 | 33.6 ± 3.7 | 88.3 ± 5.1 |
| 6A | 15.7 ± 4.3 | 99.5 ± 2.6 | 62.1 ± 16.4 | 91.5 ± 3.0 |
| 6B | 17.0 ± 6.5 | 95.2 ± 6.8 | 111.6 ± 27.8 | 85.1 ± 9.6 |
| 6C | 16.2 ± 5.9 | 97.7 ± 6.9 | 60.0 ± 21.7 | 94.4 ± 5.1 |
| 6D | 25.0 ± 7.7 | 96.9 ± 8.7 | 64.5 ± 20.5 | 101.1 ± 2.7 |
| 6E | 223.1 ± 13.7 | 90.4 ± 6.8 | 479.7 ± 124.9 | 54.1 ± 20.6 |
| 7 | 2.2 ± 0.5 | 96.9 ± 2.5 | 5.0 ± 0.7 | 101.6 ± 5.0 |
| 8 | 29.8 ± 10.5 | 98.8 ± 2.6 | 18.0 ± 4.1 | 94.7 ± 0.8 |
| 9 | 22.2 ± 5.5 | 98.4 ± 1.6 | 15.5 ± 3.7 | 92.8 ± 3.8 |
| 10 | 19.4 ± 2.0 | 84.8 ± 13.0 | 24.0 ± 4.5 | 92.8 ± 4.0 |
| 11 | 2.4 ± 0.4 | 92.3 ± 4.6 | 6.4 ± 0.9 | 105.8 ± 3.5 |
| 12 | 4.1 ± 1.4 | 90.9 ± 12.9 | 76.3 ± 28.2 | 99.8 ± 6.0 |
| 13 | 1.6 ± 0.1 | 100.0 ± 0.7 | 9.2 ± 2.7 | 93.9 ± 4.5 |
| 14 | 1.3 ± 0.1 | 102.2 ± 2.2 | 8.7 ± 1.7 | 103.1 ± 2.3 |
| 15 | 1.6 ± 0.3 | 99.9 ± 1.9 | 7.4 ± 0.4 | 94.6 ± 0.8 |
| 16 | 6.0 ± 0.8 | 102.6 ± 2.3 | 4.7 ± 0.5 | 95.2 ± 1.7 |
| 17 | 10.3 ± 2.0 | 104.6 ± 4.2 | 10.2 ± 2.2 | 96.9 ± 1.2 |
| 19 | 4.3 ± 1.2 | 99.5 ± 1.8 | 701.4 ± 219.9 | 90.7 ± 5.7 |
| 20 | 0.7 ± 0.1 | 100.2 ± 0.9 | 7.4 ± 1.5 | 101.5 ± 0.6 |
| 21 | 0.9 ± 0.1 | 100.1 ± 1.8 | 208.0 ± 26.8 | 92.1 ± 0.2 |
| 22 | 27.5 ± 6.7 | 99.1 ± 12.6 | 513.2 ± 129.5 | 38.7 ± 8.8 |
| 23 | 2.4 ± 0.1 | 95.4 ± 3.3 | 34.2 ± 13.7 | 96.4 ± 5.3 |
| 24 | 3.1 ± 0.2 | 91.7 ± 7.6 | 37.3 ± 6.4 | 87.8 ± 4.0 |
| 25 | 3.4 ± 1.0 | 93.9 ± 6.7 | 27.0 ± 3.3 | 82.5 ± 7.6 |
| 26 | 9.8 ± 1.4 | 90.2 ± 12.6 | 34.1 ± 6.8 | 93.7 ± 7.2 |
| 27 | 11.4 ± 2.0 | 95.9 ± 2.4 | 50.7 ± 6.8 | 86.3 ± 8.0 |
| 28 | 11.8 ± 7.6 | 98.7 ± 2.0 | 265.0 ± 104.2 | 56.0 ± 9.1 |
| 28A | 14.9 ± 6.3 | 108.7 ± 20.0 | 65.5 ± 3.6 | 79.7 ± 11.4 |
| 29 | 12.1 ± 0.7 | 97.0 ± 4.9 | 254.2 ± 111.2 | 89.0 ± 4.5 |
| 29A | 8.2 ± 0.7 | 100.0 ± 23.2 | 62.7 ± 14.8 | 82.8 ± 6.7 |
| 30 | 13.1 ± 4.2 | 79.1 ± 0.9 | 29.2 ± 5.6 | 87.4 ± 10.6 |

TABLE IV-continued

| Compound No. | hSSTR2 EC$_{50}$ (nM) ± SEM | % E$_{max}$ ± SEM | hDRD2 EC$_{50}$ (nM) ± SEM | % E$_{max}$ ± SEM |
|---|---|---|---|---|
| 31 | 13.3 ± 0.9 | 85.1 ± 4.7 | 37.7 ± 4.6 | 94.8 ± 9.7 |
| 32 | 13.6 ± 3.4 | 87.5 ± 4.3 | 35.6 ± 2.4 | 101.7 ± 12.8 |
| 33 | 13.8 ± 5.0 | 95.7 ± 5.1 | 51.8 ± 20.6 | 102.4 ± 12.5 |
| 34 | 14.6 ± 5.7 | 95.1 ± 7.1 | 72.7 | 77.9 |
| 35 | 19.4 ± 6.2 | 91.2 ± 11.0 | 97.4 ± 21.1 | 102.8 ± 1.4 |
| 37 | 23.1 ± 4.3 | 85.5 ± 6.7 | 33.4 ± 14.4 | 93.7 ± 4.3 |
| 38 | 24.9 ± 7.7 | 83.5 ± 4.4 | 7.5 ± 0.1 | 97.5 ± 0.3 |
| 39 | 25.9 ± 6.9 | 87.1 ± 4.7 | 114.4 ± 24.4 | 95.7 ± 2.4 |
| 40 | 27.0 ± 6.5 | 95.0 ± 6.1 | 122.9 ± 6.5 | 91.5 ± 0.0 |
| 41 | 29.6 | 104.5 | 62.6 | 91.2 |
| 42 | 30.7 ± 15.0 | 78.6 ± 2.3 | 65.2 ± 13.7 | 94.5 ± 0.3 |
| 43 | 31.6 ± 4.3 | 92.8 ± 9.4 | | |
| 44 | 39.3 ± 16.7 | 97.1 ± 5.9 | 232.2 ± 33.1 | 59.9 ± 0.5 |
| 46 | 60.0 | 84.0 | 30.9 | 105.3 |
| 47 | 77.5 ± 19.0 | 96.2 ± 5.9 | 46.6 ± 12.2 | 92.5 ± 0.8 |
| 48 | 23.6 ± 7.9 | 95.5 ± 11.9 | 78.3 ± 15.2 | 76.5 ± 2.8 |

Reference Compound Nos. A, B, and C, whose chemical names and their corresponding structures are provided in Table V, were synthesized and their ability to activated hSSTR2 and hDRD2 was determined by the same intracellular calcium mobilization assays using FLIPR Calcium 4 assay kit (Molecular Devices) and under the same experimental conditions for test compounds, as described hereinabove, and the results thereof are provided in Table VI.

TABLE V

| Reference Compound No. | Chemical Name; Corresponding Structure |
|---|---|
| A | Dop1-cyclo(DDab-Arg-Phe-Phe-DTrp-Lys-Thr-Phe) (SEQ ID NO: 55); |

TABLE V-continued

| Reference Compound No. | Chemical Name; Corresponding Structure |
|---|---|
| B | Dop1-Tyr-cyclo(DDab-Arg-Phe-Phe-DTrp-Lys-Thr-Phe) (SEQ ID NO: 56); |

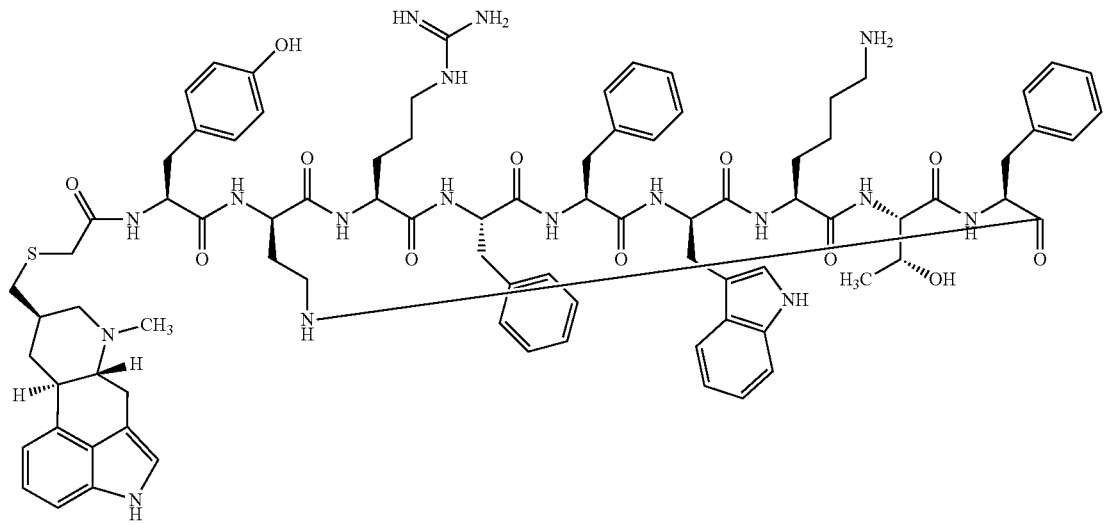

| | |
|---|---|
| C | Dop1-Lys(Dop1)-cyclo(DDab-Arg-Phe-Phe-DTrp-Lys-Thr-Phe) (SEQ ID NO: 57); |

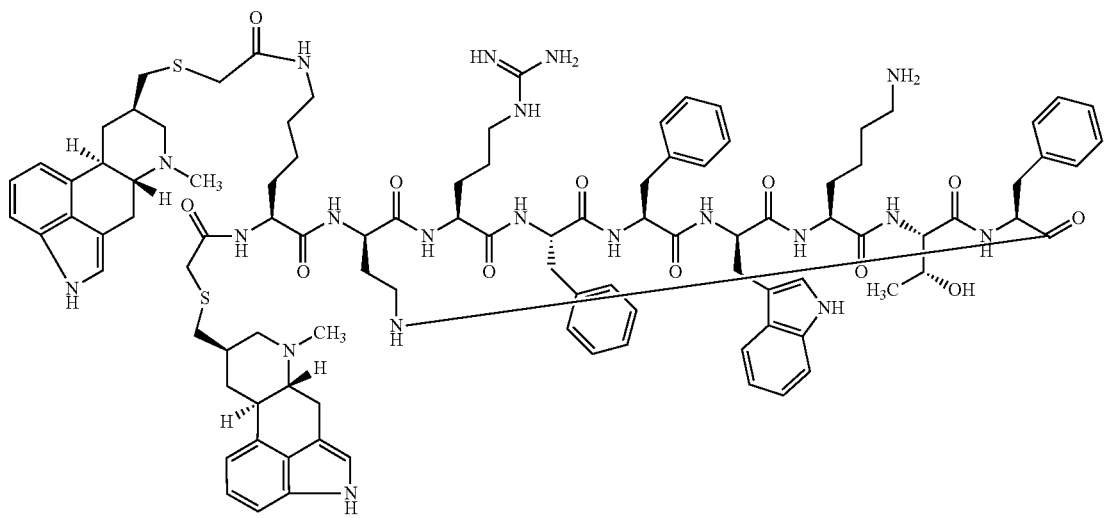

TABLE VI

| Reference Compound | hSSTR2 | | hDRD2 | |
|---|---|---|---|---|
| No. | $EC_{50}$ (nM) ± SEM | % $E_{max}$ ± SEM | $EC_{50}$ (nM) ± SEM | % $E_{max}$ ± SEM |
| A | 26.5 ± 2.3 | 86.2 ± 7.0 | 401.2 ± 141.2 | 59.7 ± 7.0 |
| B | 18.8 ± 4.8 | 66.7 ± 5.8 | 62.8 ± 9.8 | 92.8 ± 6.6 |
| C | 68.7 ± 40.8 | 60.6 ± 3.2 | 111.8 ± 39.2 | 101.0 ± 0.8 |

In the chemical names as listed in Table V, the term "Dab" is an abbreviation for an amino acid residue 2,4-diaminobutyric acid.

Referring to Tables IV and VI, surprisingly, Compounds 24, 25, 6, 7, 23, and 29 showed statistically significant improvement in $EC_{50}$ over Reference Compound A, with the p value (Student's t-test, one-tailed) being <0.05. For instance, Compound 24 structurally differs from Reference Compound A only with respect to the presence of DLys, instead of DDab, at the first amino acid residue position of the cyclic peptide moiety, and the presence of 4Pal, instead of Phe, at the fourth amino acid residue position of the cyclic peptide moiety, and it would have been unexpected and surprising for a person having ordinary skill in the art to which the present invention pertains to find that, based on the data presented in Tables IV and V in the present application, that the $EC_{50}$ value for Compound 24 is about 9-fold lower than that for Reference Compound A.

Likewise, referring to Tables IV and V, surprisingly, Compound 4, 5, 32, and 33 showed statistically significant improvement in $EC_{50}$ and/or % $E_{max}$ over Reference Compound B.

Likewise, referring to Tables IV and V, surprisingly, Compound 8, 9, and 47 showed statistically significant improvement in % $E_{max}$ over Reference Compound C.

Human Pituitary Adenoma Cell Growth Hormone Release Assay

Acromegalic patients presenting with macroadenoma underwent transsphenoidal surgery and a portion of each tumor obtained at surgery was dissociated by enzymatic and mechanical methods. The cells were cultured in DMEM medium supplemented with 10% FBS and antibiotics for 3 days. The cells were then plated in multi-well tissue culture dishes coated with extracellular matrix from bovine endothelial corneal cells at a density of $3-5 \times 10^4$ cells/well in DMEM supplemented with 10% FBS and antibiotics. After 2-3 days of culture, the medium was changed to DMEM supplemented with 1% FBS, antibiotics and 1% ITS (insulin, transferrin and selenium).

Figure 5:
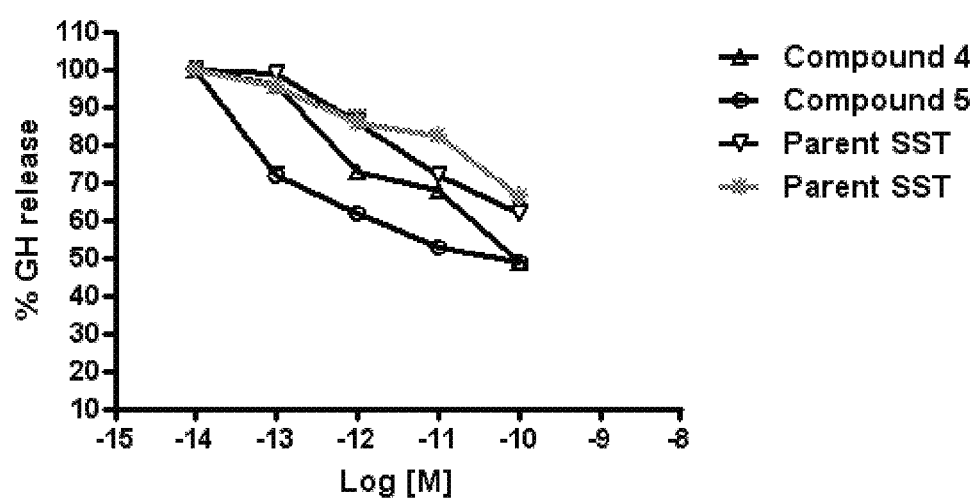
FIG. 5 is a graph showing the enhanced Growth hormone suppressing activity of Compounds 4 and 5 (see Table I hereinbelow for their chemical name and their corresponding structural representation) compared to the parent somatostatin analogs (i.e., the somatostatin moiety of Compounds 4 and 5) on pituitary tumor cells of acromegalic patients presenting with macroadenoma. Various concentrations of Compounds 4 and 5 were added to the medium and the cells were incubated for 18 hours before measurement of Growth hormone levels in the medium using the AlphaLISA Growth Hormone Immunoassay Research kit (PerkinElmer).

As shown in FIGS. 1-4, the somatostatin-dopamine chimeric analogs of the present invention have significant Growth hormone suppressing activity on pituitary tumor cells of acromegalic patients presenting with macroadenoma in a dose-response manner; and as shown in FIG. 5, such Growth hormone suppressing activity of the somatostatin-dopamine chimeric analogs of the present invention is significantly better than their parent somatostatin analogs.

All publications, patent applications, patents, and other documents cited herein are incorporated by reference in their entirety. In case of conflict, the present specification, including definitions, will control. In addition, the materials, methods, and examples are illustrative only and not intended to be limiting.

Obvious variations to the disclosed compounds and alternative embodiments of the invention will be apparent to those skilled in the art in view of the foregoing disclosure. All such obvious variants and alternatives are considered to be within the scope of the invention as described herein.

The invention claimed is:

1. A method of treating a neuroendocrine tumor in a subject, wherein said neuroendocrine tumor is selected from the group consisting of a neuroendocrine tumor of the pituitary, an ACTH-producing tumor, a growth hormone producing tumor, a prolactin-producing tumor, thyroid stimulating hormone secreting tumor, a nonfunctioning pituitary adenoma, gonadotropinoma, a carcinoid tumor, glucagonoma, VIPoma and insulinoma, said method comprising administering to said subject a therapeutically effective amount of a compound, wherein the compound is:

(SEQ ID NO: 4)
Dop1-Tyr-psi(CH$_2$NH)-cyclo(DLys-Arg-Phe-4Pal-DTrp-Lys-Thr-Phe);

(SEQ ID NO: 5)
Dop1-Tyr-psi(CH$_2$NH)-cyclo(DLys-Arg-Phe-Phe-DTrp-Lys-Thr-4FPhe);

(SEQ ID NO: 6)
Dop1-psi(CH$_2$NH)-cyclo(DLys-Arg-Phe-Phe-DTrp-Lys-Thr-4FPhe);

(SEQ ID NO: 12)
Dop1-psi(CH$_2$NH)-cyclo(DLys-Arg-Phe-4Pal-DTrp-Lys-Thr-Tyr);

(SEQ ID NO: 13)
Dop1-Lys(Dop1)-psi(CH$_2$NH)-cyclo(DLys-Arg-Phe-4Pal-DTrp-Lys-Thr-Tyr);

```
                                                     (SEQ ID NO: 14)
Dop1-Lys(Dop1)-psi(CH₂NH)-cyclo(DLys-Arg-Phe-
4Pal-DTrp-Lys-Thr-Phe);

(SEQ ID NO: 15)
Dop1(SO₂)-psi(CH₂NH)-cyclo(DLys-Arg-Phe-Phe-DTrp-
Lys-Thr-4FPhe);

(SEQ ID NO: 18)
Dop1(SO)-psi(CH₂NH)-cyclo(DLys-Arg-Phe-4Pal-DTrp-
Lys-Thr-Tyr);

(SEQ ID NO: 19)
Dop1(SO)-Tyr-psi(CH₂NH)-cyclo(DLys-Arg-Phe-Phe-
DTrp-Lys-Thr-4FPhe);

(SEQ ID NO: 20)
Dop1(SO)-psi(CH₂NH)-cyclo(DLys-Arg-Phe-Phe-DTrp-
Lys-Thr-4FPhe);

(SEQ ID NO: 21)
Dop1(SO)-Tyr-psi(CH₂NH)-cyclo(DLys-Arg-Phe-4Pal-
DTrp-Lys-Thr-Phe);

(SEQ ID NO: 22)
Dop1(SO)-Lys[Dop1(SO)]-psi(CH₂NH)-cyclo(DLys-Arg-
Phe-4Pal-DTrp-Lys-Thr-Tyr);

(SEQ ID NO: 23)
Dop1(SO)-Lys[Dop1(SO)]-psi(CH₂NH)-cyclo(DLys-Arg-
Phe-4Pal-DTrp-Lys-Thr-Phe);

(SEQ ID NO: 24)
Dop1(SO₂)-Tyr-psi(CH₂NH)-cyclo(DLys-Arg-Phe-Phe-
DTrp-Lys-Thr-4FPhe);

(SEQ ID NO: 25)
Dop1(SO₂)-psi(CH₂NH)-cyclo(DLys-Arg-Phe-4Pal-
DTrp-Lys-Thr-Tyr);

(SEQ ID NO: 26)
Dop1(SO₂)-Tyr-psi(CH₂NH)-cyclo(DLys-Arg-Phe-
4Pal-DTrp-Lys-Thr-Phe);

(SEQ ID NO: 28)
Dop1-psi(CH₂NH)-cyclo(DLys-Arg-Phe-4Pal-DTrp-Lys-
Thr-Phe);

(SEQ ID NO: 29)
Dop1-cyclo(DLys-Arg-Phe-4Pal-DTrp-Lys-Thr-Phe);

(SEQ ID NO: 30)
Dop1-cyclo(DLys-Arg-Phe-4Pal-DTrp-Lys-Thr-Tyr);

(SEQ ID NO: 31)
Dop1-psi(CH₂NH)-cyclo(DLys-Arg-Phe-Phe-DTrp-Lys-
Thr-Phe);

(SEQ ID NO: 35)
bis[Dop1-psi(CH₂N)]-cyclo(DLys-Arg-Phe-4Pal-DTrp-
Lys-Thr-Phe);

(SEQ ID NO: 39)
Dop1-Tyr-psi(CH₂NH)-cyclo(DLys-Arg-Phe-DTrp-
Lys-Thr-Phe);

(SEQ ID NO: 40)
Dop1-Tyr-psi(CH₂NH)-cyclo(DLys-Arg-Phe-Phe-DTrp-
Lys-Thr-Tyr);

(SEQ ID NO: 41)
Dop1-cyclo(DLys-Arg-Phe-Phe-DTrp-Lys-Thr-4FPhe);

(SEQ ID NO: 42)
bis[Dop1-psi(CH₂N)]-cyclo(DLys-Arg-Phe-4Pal-DTrp-
Lys-Thr-Tyr);

(SEQ ID NO: 43)
Dop1-DTyr-cyclo(DLys-Arg-Phe-Phe-DTrp-Lys-Thr-
Phe);

(SEQ ID NO: 44)
Dop1-Tyr-psi(CH₂NH)-cyclo(DLys-Arg-Phe-3Pal-DTrp-
Lys-Thr-Phe);

(SEQ ID NO: 45)
bis[Dop1-psi(CH₂N)]-cyclo(DLys-Arg-Phe-Phe-DTrp-
Lys-Thr-4FPhe);

(SEQ ID NO: 46)
bis[Dop1-psi(CH₂N)]-cyclo(DLys-Arg-Phe-Phe-DTrp-
Lys-Thr-Phe);

(SEQ ID NO: 47)
Dop1-DTyr-psi(CH₂NH)-cyclo(DLys-Arg-Phe-Phe-DTrp-
Lys-Thr-Phe);

(SEQ ID NO: 50)
Dop1-cyclo(DLys-Arg-Phe-Phe-DTrp-Lys-Thr-Phe);

(SEQ ID NO: 51)
Dop1-DTyr-psi(CH₂NH)-cyclo(DLys-Arg-4Pal-Tyr-
DTrp-Lys-Thr-Phe);
or
                                                     (SEQ ID NO: 52)
Dop1-Lys(Dop1)-psi(CH₂NH)-cyclo(DLys-Arg-Phe-Phe-
DTrp-Lys-Thr-4FPhe);
``` or a pharmaceutically acceptable salt thereof, and wherein said therapeutically effective amount is the amount effective to treat said neuroendocrine tumor in said subject.

2. The method according claim 1, wherein said compound is:

```
                                                     (SEQ ID NO: 4)
Dop1-Tyr-psi(CH₂NH)-cyclo(DLys-Arg-Phe-4Pal-DTrp-
Lys-Thr-Phe);

(SEQ ID NO: 5)
Dop1-Tyr-psi(CH₂NH)-cyclo(DLys-Arg-Phe-Phe-DTrp-
Lys-Thr-4FPhe);

(SEQ ID NO: 6)
Dop1-psi(CH₂NH)-cyclo(DLys-Arg-Phe-Phe-DTrp-Lys-
Thr-4FPhe);
```

-continued

```
                                              (SEQ ID NO: 12)
Dop1-psi(CH2NH)-cyclo(DLys-Arg-Phe-4Pal-DTrp-Lys- Thr-Tyr);

(SEQ ID NO: 13)
Dop1-Lys(Dop1)-psi(CH2NH)-cyclo(DLys-Arg-Phe-4Pal-

DTrp-Lys-Thr-Tyr);

(SEQ ID NO: 14)
Dop1-Lys(Dop1)-psi(CH2NH)-cyclo(DLys-Arg-Phe-4Pal-

DTrp-Lys-Thr-Phe);
or (SEQ ID NO: 15)
Dop1(SO2)-psi(CH2NH)-cyclo(DLys-Arg-Phe-Phe-DTrp- Lys-Thr-4FPhe);
``` or a pharmaceutically acceptable salt thereof.

3. The method of claim 1, wherein said neuroendocrine tumor is a neuroendocrine tumor of the pituitary.

4. The method of claim 3, wherein said neuroendocrine tumor of the pituitary is an ACTH-producing tumor.

5. The method of claim 4, wherein said ACTH-producing tumor causes Cushing's disease.

6. The method of claim 3, wherein said neuroendocrine tumor of the pituitary is a growth hormone producing tumor.

7. The method of claim 6, wherein said growth hormone producing tumor causes acromegaly.

8. The method of claim 3, wherein said neuroendocrine tumor of the pituitary is a prolactin-producing tumor.

9. The method of claim 8, wherein said prolactin-producing tumor causes prolactinoma.

10. The method of claim 3, wherein said neuroendocrine tumor of the pituitary causes hyperprolactinemia.

11. The method of claim 3, wherein said neuroendocrine tumor of the pituitary is thyroid stimulating hormone secreting tumor.

12. The method of claim 3, wherein said neuroendocrine tumor of the pituitary is nonfunctioning pituitary adenoma.

13. The method of claim 3, wherein said neuroendocrine tumor of the pituitary is gonadotropinoma.

14. The method of claim 1, wherein the neuroendocrine tumor is a carcinoid tumor.

15. The method of claim 14, wherein said carcinoid tumor causes carcinoid syndrome.

16. The method of claim 1, wherein said neuroendocrine tumor is glucagonoma.

17. The method of claim 1, wherein said neuroendocrine tumor is VIPoma.

18. The method of claim 1, wherein said neuroendocrine tumor is insulinoma.

* * * * *